United States Patent
Cragg et al.

(10) Patent No.: US 11,623,005 B2
(45) Date of Patent: **\*Apr. 11, 2023**

(54) COMBINED USE OF FCγRIIB (CD32B) AND CD20 SPECIFIC ANTIBODIES

(71) Applicant: UNIVERSITY OF SOUTHAMPTON, Southampton (GB)

(72) Inventors: Mark Cragg, Southampton (GB); Martin Glennie, Southampton (GB); Ali Roghanian, Southampton (GB); Stephen Beers, Southampton (GB); Peter Johnson, Southampton (GB); Sean Lim, Southampton (GB); Bjorn Frendeus, Landskrona (SE); Ingrid Teige, Lund (SE)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 543 days.

This patent is subject to a terminal disclaimer.

(21) Appl. No.: 16/684,450

(22) Filed: Nov. 14, 2019

(65) Prior Publication Data

US 2020/0069798 A1   Mar. 5, 2020

Related U.S. Application Data

(63) Continuation of application No. 13/817,744, filed as application No. PCT/GB2011/051572 on Aug. 19, 2011, now Pat. No. 10,525,129.

(30) Foreign Application Priority Data

Aug. 20, 2010   (GB) .................................... 1013989

(51) Int. Cl.
  *C07K 16/00*    (2006.01)
  *C12P 21/08*    (2006.01)
  *A61K 39/395*   (2006.01)
  *C07K 16/28*    (2006.01)
  *G01N 33/68*    (2006.01)
  *C07K 1/00*     (2006.01)
  *A61K 39/00*    (2006.01)

(52) U.S. Cl.
  CPC ...... *A61K 39/39558* (2013.01); *C07K 16/283* (2013.01); *C07K 16/2803* (2013.01); *C07K 16/2887* (2013.01); *G01N 33/6893* (2013.01); *A61K 2039/507* (2013.01)

(58) Field of Classification Search
  None
  See application file for complete search history.

(56) References Cited

U.S. PATENT DOCUMENTS

| 4,485,045 | A | 11/1984 | Regen |
| 4,544,545 | A | 10/1985 | Ryan et al. |
| 4,880,078 | A | 11/1989 | Inoue et al. |
| 5,290,540 | A | 3/1994 | Prince et al. |
| 5,855,913 | A | 1/1999 | Hanes et al. |
| 5,874,064 | A | 2/1999 | Edwards et al. |
| 5,934,272 | A | 8/1999 | Lloyd et al. |
| 5,985,309 | A | 11/1999 | Edwards et al. |
| 6,019,968 | A | 2/2000 | Platz et al. |
| 10,525,129 | B2 * | 1/2020 | Cragg .................... A61P 43/00 |
| 2004/0185045 | A1 | 9/2004 | Koenig et al. |
| 2005/0215767 | A1 | 9/2005 | Koenig et al. |
| 2005/0260213 | A1 | 11/2005 | Koenig et al. |
| 2006/0013810 | A1 | 1/2006 | Johnson et al. |
| 2006/0134709 | A1 | 6/2006 | Stavenhagen et al. |
| 2008/0014141 | A1 | 1/2008 | Huber et al. |
| 2009/0010920 | A1 | 1/2009 | Lazar et al. |

FOREIGN PATENT DOCUMENTS

| GB | 2526139 A | 11/2015 |
| WO | 92/19244 A2 | 11/1992 |
| WO | 97/32572 A2 | 9/1997 |
| WO | 97/44013 A1 | 11/1997 |
| WO | 98/31346 A1 | 7/1998 |
| WO | 99/66903 A2 | 12/1999 |
| WO | 2004/016750 A2 | 2/2004 |
| WO | 2005/018669 A1 | 3/2005 |
| WO | 2006/066078 A2 | 6/2006 |
| WO | 2008/002933 A2 | 1/2008 |
| WO | 2008/140603 A2 | 11/2008 |
| WO | 2009/062083 A2 | 5/2009 |
| WO | 2009/083009 A2 | 7/2009 |
| WO | 2010/080994 A2 | 7/2010 |

(Continued)

OTHER PUBLICATIONS

Chiu et al. Antibodies 2019, 8,55; 1-80. (Year: 2019).*
Sela-Culang et al. Frontiers in Immunology, 2013, vol. 4, Article 302, pp. 1-13. (Year: 2013).*
Janeway et al., Immunology Third Edition, Garland Publishing Inc. 1997, Chapter 3, Structure of the Antibody Molecule and Immunoglobulin Genes, pp. 3:1-3:11. (Year: 1997).*

(Continued)

*Primary Examiner* — Chun W Dahle

(74) *Attorney, Agent, or Firm* — Rodney J. Fuller; Booth Udall Fuller, PLC

(57) ABSTRACT

The invention provides a method of treating a patient having target cells that express FcγRIIb, the method comprising administering (i) an antibody molecule that specifically binds a surface antigen of the target cell, which antibody molecule has an Fc domain capable of binding FcγRIIb; in combination with (ii) an agent that prevents or reduces binding between the Fc domain of the antibody molecule and FcγRIIb; characterized in that the patient is selected on the basis that their target cells express an elevated level of FcγRIIb.

5 Claims, 36 Drawing Sheets

Specification includes a Sequence Listing.

(56) References Cited

FOREIGN PATENT DOCUMENTS

| WO | 2012/022985 A1 | 2/2012 |
|---|---|---|
| WO | 2015/173384 A1 | 11/2015 |

OTHER PUBLICATIONS

Lenz et al., "Immunochemotherapy With Rituximab and Cyclophosphamide, Doxorubicin, Vincristine, and Prednisone Significantly Improves Response and Time to Treatment Failure, But Not Long-Term Outcome in Patients With Previously Untreated Mantle Cell Lymphoma: Results of a Prospective Randomized Trial of the German Low Grade Lymphoma Study Group (GLSG)", J Clin Oncol, 23:1984-1992 (2005).
Li et al., "A Novel Polymorphism in the Fcγ Receptor IIB (CD32B) Transmembrane Region Alters Receptor Signaling", Arthritis Rheum, 48:3242-3252 (2003).
Lim et al., "Fc gamma receptor IIb on target B cells promotes rituximab internalization and reduces clinical efficacy", Blood, 118(9):2530-2540 (2011).
Lim et al. Meeting abstract. 14th International Congress of Immunology, Kobe Japan, Aug. 22-24, 2010(b).
Lim et al. Meeting Abstract. School of Medical Academic Clinical Trainee Conference, Southampton UK, Jul. 5, 2010.
Marcus et al., "CVP chemotherapy plus rituximab compared with CVP as first-line treatment for advanced follicular lymphoma", Blood, 105:1417-1423 (2005).
"Disease", retrieved from https://en.wikipedia.org/wiki/Disease, retrieved on May 2, 2017.
Medical News Today, www.medicalnewstoday.com, Genmab announces HuMax CD32b Pre Clinical Program, Jan. 5, 2008.
Michel et al., "Intracellular Accumulation of the Anti-CD20 Antibody 1F4 in B-Lymphoma Cells", Clin Cancer Res, 8:2701-2713 (2002).
Mitsudomi et al., "Epidermal growth factor receptor in relation to tumor development: EGVR gene and cancer", FEBS J., 277(2):301-308 (2010).
Mockridge et al., "Reversible anergy of sigM-mediated signaling in the two subsets of CLL defined by VH-gene mutational status", Blood, 109:4424-4431 (2007).
Mossner et al., "Increasing the efficacy of CD20 antibody therapy through the engineering of a new type II anti-CD20 antibody with enhanced direct and immune effector cell-mediated B-cell cytotoxicity", Blood, 115(22):4393-4402 (2010).
Neubig et al., "International Union of Pharmacology Committee on Receptor Nomenclature and Drug Classification. XXXVIII. Updated on Terms and Symbols in Quantitative Pharmacology", Pharmacol. Rev. 55:597-606 (2003).
Ni et al., "Cloning and characterization of a human LYPD7, a new member of the Ly-6 superfamily", Mol Biol Rep, 36 (4):697-703 (2009).
Niederfellner et al., "Epitope characterization and crystal structure of GA101 provide insights into the molecular basis for type I/II distinction of CD20 antibodies", Blood, 118:358-367 (2011).
Nimmerjahn et al., "Antibodies, Fc receptors and cancer", Curr Opin Immuno, 19:239-245 (2007).
Nimmerjahn et al., "FCγ receptors as regulators of immune responses", Nat Rev Immunol, 8:34-47 (2008).
Park et al., "Unraveling the Biologic and Clinical Complexities of HER2", Clin Breast Cancer, 8(5):392-401 (2008).
Polyak et al., "CD20 Homo-oligomers Physically Associate with the B Cell Antigen Receptor", J Biol Chem, 283:18545-18552 (2008).
Potter et al., "Structural and Functional Features of the B-Cell Receptor in IgG Positive Chronic Lymphocytic Leukemia", Clin Cancer Res, 12:1672-1679 (2006).
Rankin et al., "CD32B, the human inhibitory Fc-γ receptor IIB, as a target for monoclonal antibody therapy of B-cell lymphoma", Blood, 108:2384-2391 (2006).
Ravetch et al., "IgG Rc Receptors", Annu Rev Immunol, 19:275-290 (2001).
Robak et al., "Rituximab Plus Fludarabine and Cyclophosphamide Prolongs Progression-Free Survival Compared with Fludarabine and Cyclophosphamide Alone in Previously Treated Chronic Lymphocytic Leukemia", J Clin Oncol, 28(10):1756-1765 (2010).
Roghanian et al., "Modulating immune responses by targeting the inhibitory Fcgamma receptor CD32B to improve cancer therapy", Meeting abstract. 14th International Congress of Immunology, Kobe Japan, Aug. 22-24, 2010.
Sehn et al., "Introduction of Combined CHOP Plus Rituximab Therapy Dramatically Improved Outcome of Diffuse Large B-Cell Lymphoma in British Columbia", J Clin Oncol, 23:5027-5033 (2005).
Stolz et al., "Molecular Mechanisms of Resistance to Rituximab and pharmacologic strategies for its circumvention", Leuk Lymphoma, 50:873-885 (2009).
Teeling et al., "Characterization of new human CD20 monoclonal antibodies with potent cytolytic activity against non-Hodgkin lymphomas", Blood, 104:1793-1800 (2004).
Ternynck et al., "Comparison of Normal and CLL Lymphocyte Surface Ig Determinants Using Peroxidase-Labeled Antibodies. I. Detection and Quantitation of Light Chain Determinants", Blood, 43-789-795 (1974).
Treon et al., "Tumor Cell Expression of CD50 is Associated with Resistance to CD20 Serotherapy in Patients with B-Cell Malignancies", J Immunother, 24:263-271 (1991).
Tutt et al., "Monoclonal Antibody Therapy of B Cell Lymphoma: Signaling Activity on Tumor Cells Appears More Important Than Recruitment of Effectors", J Immunol, 161:3176-3185 (1998).
Uchida et al., "The Innate Mononuclear Phagocyte Network Depletes B Lymphocytes through Fc Receptor-dependent Mechanisms during Anti-CD20 Antibody Immunotherapy", J Exp Med, 199:1659-1669 (2004).
Walshe et al., "Induction of Cytosolic Calcium Flux by CD20 is Dependent Upon B Cell Antigen Receptor Signaling", J Biol Chem, 283:16971-16984 (2008).
Weng et al., "Two Immunoglobulin G Fragment C Receptor Polymorphisms Independently Predict Response to Rituximab in Patients with Follicular Lymphoma", J Clin Oncol, 21:3940-3947 (2003).
Weng et al., "Genetic polymorphism of the inhibitory IgG Fc receptor FCγRIIb is not associated with clinical outcome in patients with follicular lymphoma treated with rituximab", Leuk Lymphoma, 50:723-727 (2009).
Wiestner et al., "ZAP-70 expression identifies a chronic lymphocytic leukemia subtype with unmutated immunoglobulin genes, inferior clinical outcome, and distinct gene expression profile", Blood, 101:4944-4951 (2003).
Yang et al., "Down-Regulation of CD40 Gene Expression and Inhibition of Apoptosis with Danshensu in Endothelial Cells", Basic Clin Pharmacol Toxicol, 104(2):87-92 (2009).
Harlow & Lane, Antibodies: A Laboratory Manual, pp. 567-569, 574-576, 583, and 590-612 (1988).
Kabat et al., In "Sequences of Proteins of Immunological Interest" Fifth Edition, NIH Publication No. 91-3242, pp. xv-xvii (1991).
Marcus et al., "Phase III Study of R-CVp Compared with Cyclophosphamide, Vincristine, and Prednisone Alone in Patients with Previously Untreated Advanced Follicular Lymphoma", J Clin Oncol, 26:4579-4586 (2008).
Shim et al., "One target, difference effects: a comparison of distinct therapeutic antibodies against the same targets", Experimental and Molecular Medicine, 43:539-549 (Oct. 2011).
Bournazos et al., "Association of FcγRIIa (CD32a) with Lipid Rafts Regulates Ligand Binding Activity", The Journal of Immunology, 182:8026-8036 (2009).
Smith, "Rituximab (monoclonal anti-CD20 antibody): mechanisms of action and resistance", Oncogene, 22:7359-7368 (2003).
Vervoordeldonk et al., "Fc gamma receptor II (CD32) on malignant B cells influences modulation induced by anti-CD19 monoclonal antibody", Blood, 83:1632-1639 (1994).
Vaughan et al., "Inhibitory FcγRIIb (CD32b) becomes activated by therapeutic mAb in both cis and trans and drives internalization according to antibody specificity", Blood, 123(5):669-677 (2014).

(56) References Cited

OTHER PUBLICATIONS

Tong et al., "Prospects for CD40-directed experimental therapy of human cancer", Cancer Gene Ther., 10(1):1-13 Jan. 2003, Abstract Only.
Pallasch et al., "Sensitizing Protective Tumor Microenvironments to Antibody-Mediated Therapy", Cell, 156:590-602 (Jan. 30, 2014).
Roghanian et al., "Antagonistic Human FcγRIIB (CD32B) Antibodies Have Anti-Tumor Activity and Overcome Resistance to Antibody Therapy In Vivo", Cancer Cell, 27:473-488 (Apr. 13, 2015).
Williams et al., "Overcoming Resistance to Therapeutic Antibodies by Targeting Fc Receptors", Resistance to Immunotherapeutic Antibodies in Cancer, pp. 49-71 (2013).
Aman et al., "FcγRIIB1/SHIP-mediated Inhibitory Signaling in B Cells Involves Lipid Rafts", J Biol Chem, 276:46371-46378 (2001).
Beers et al., "Type II (tositumomab) anti-CD20 monoclonal antibody out performs type I (rituximab-like) reagents in B-cell depletion regardless of complement activation", Blood, 112:4170-4177 (2008).
Beers et al., Antigenic modulation limits the efficacy of anti-CD20 antibodies: implications for antibody selection, Blood, 115(25): 5191-5201 (2010).
Beers et al., "CD20 as a Target for Therapeutic Type I and II Monoclonal Antiboides", Seminars in Hematology. 47(2): 107-114 (Apr. 2010).
Bradley et al., "Rules and regulation of Thy-1, a context-dependent modulator of cell phenotype", Biofactors;35(3):258-65 (2009).
Bricarello et al., "Ganglioside embedded in reconstituted lipoprotein binds cholera toxin with elevated affinity", J Lipid Res., 51(9):2731-2738 (2010).
Busillo et al., "Regulation of CXCR4 Signaling", Biochim Biophys Acta, 1768(4):952-963 (2007).
Callanan et al., The IgG Fc receptor, FcγRIIB, is a target for deregulation by chromosomal translocation in malignant lymphoma, PNAS, 97:309-314 (2000).
Camilleri-Broet et al., "FcγRIIB expression in diffuse large B-cell lymphomas does not alter the response to CHOP + rituximab (R-CHOP)", Leukemia, 18:2038-2040 (2004).
Camilleri-Broet et al., "FcγRIIB is differentially expressed during B cell maturation and in B-cell lymphomas", Br J Haematol 124:55-62(2004).
Chan et al., "CD20-induced Lymphoma Cell Death Is Independent of Both Caspases and Its Redistribution into Triton X-100 Insoluble Membrane Rafts", Cancer Res, 63:5480-5489 (2003).
Cheson et al., "Monoclonal Antibody Therapy for B-Cell Non-Hodgkin's Lymphoma", NEJM, 359(6): 613-626 (2008).
Clynes et al., "Inhibitory Rc receptors modulate in vivo cytoxicity against tumor targets", Nat Med, 6:443-446 (2000).
Cragg, Mark, "CD20 antibodies: doing the time warp", Blood, 118:219-220 (2011).
Cragg et al., "Antibody specificity controls in vivo effector mechanisms of anti-CD20 reagents", Blood, 103:2738-2743 (2004).
Cragg et al., "Complement-mediated lysis by anti-CD20 mAb correlates with segregation into lipid rafts", Blood, 101 (3):1045-1052 (2003).
Crespo et al., "ZAP-70 Expression as a Surrogate for Immunoglobulin-Variable-Region Mutations in Chronic Lymphocytic Leukemia", N Engl J Med, 348:1764-1775 (2003).
Damle et al., "Ig V Gene Mutation Status and CD38 Expression As Novel Prognostic Indicators in Chronic Lymphocytic Leukemia", Blood, 94:1840-1847 (1999).
Davis et al., "Therapy of B-Cell Lymphoma with Anti-CD20 Antibodies Can Result in the Loss of CD20 Antigen Expression", Clin Cancer Res, 5:611-615 (1999).
Deans et al., "Rapid Redistribution of CD20 to a Low Density Detergent-insoluble Membrane Compartment", J. Biol. Chem., 273: 344-348 (1998).
De Rie et al., "Regulatory Role of CD19 Molecules in B-Cell Activation and Differentiation", Cell Immunol., 118(2):368-381 (1989).
Ehrenschwender et al., "The Role of FasL and Fas in Health and Disease", Adv Exp Med Biol, 647:64-93 (2009).
Epstein et al., "Biological activity of liposome-encapsulated murine interferon γ is mediated by a cell membrane receptor", Proc. Natl. Acad. Sci. USA, 82:3688-3692 (Jun. 1985).
Feugier et al., "Long-Term Results of the R-CHOP Study in the Treatment of Elderly Patients With Diffuse Large B-Cell Lymphoma: A Study by the Groupe d'Etude des Lymphomes de l'Adulte", J Clin Oncol, 23:4117-4126 (2005).
Fridman et al., "Soluble Fcγ receptors", J Leukoc Biol, 54:504-512 (1993).
Genmab, "Genmab announces HuMax-CD32B preclinical program", Stock exchange release, (2008).
Glennie et al., "Preparation and Performance of Bispecific F(ab'γ)2 Antibody Containing Thioether-Linked Fab'γ Fragments", J Immunol, 139:2367-2375, (1987).
Golay et al., "CD20 levels determine the in vitro susceptibility to rituximab and complement of B-cell chronic lymphocytic leukemia: further regulation by CD55 and CD59", Blood, 98:3383-3389 (2001).
Greenman et al., "Characterization of a New Monoclonal Anti-FcγRII Antibody, AT10 and Its Incorporation into a bispecific F(ab')2 Derivative for Recruitment of Cytotoxic Effectors", Mol Immunol, 28:1243-1254 (1991).
Hamblin et al., "Unmutated Ig VH Genes Are Associated With a More Aggressive Form of Chronic Lymphocytic Leukemia", Blood, 94:1848-1854 (1999).
Hamblin et al., "CD38 expression and immunoglobulin variable region mutations are independent prognostic variables in chronic lymphocytic leukemia, but CD38 expression may vary during the course of the disease", Blood, 99:1023-1029 (2002).
Hiraga et al., "Down-regulation of CD20 expression in B-cell lymphoma cells after treatment with rituximab-containing combination chemotherapies: its prevalence and clinical significance", Blood, 113:4885-4893 (2009).
Hwang et al., "Hepatic Uptake and Degradation of Unilamellar Sphingomyelin/Cholesterol Liposomes: A Kinetic Study", Proc. Natl. Acad. Sci. USA, 77: 4030-4034 (1980).
Ibrahim et al., "CD38 expression as an important prognostic factor in B-cell chronic lymphocytic leukemia", Blood, 98:181-186 (2001).
Ivanov et al., "Monoclonal Antibodies Directed to CD20 and HLA-DR can elicit homotypic adhesion followed by lysosome-mediated cell death in human lymphoma and leukemia cells", J Clin Invest, 119:2143-2159 (2009).
Jazirehi et al., "Development of Rituximab-Resistant Lymphoma Clones With Altered Cell Signaling and Cross-Resistance to Chemotherapy", Cancer Res, 67:1270-1281 (2007).
Kharfan-Dabaja et al., "Evolving Role of Monoclonal Antibodies in the Treatment of Chronic Lymphocytic Leukemia", Expert Opin Investig Drugs, 16:1799-1815 (2007).
Kimberley et al., "Alternative Roles for CD59", Mol Immunol., 44(1-3)73-81 (2007).
Kono et al., "FcγRIIB Ile232 Thr transmembrane polymorphism associated with human systemic lupus erythematosus decreases affinity to lipid rafts and attenuates inhibitory effects on B cell receptor signaling", Hum Mol Genet, 14:2881-2892 (2005).
Krober et al., "VH mutation status, CD38 expression level, genomic aberrations, and survival in chronic lymphocytic leukemia", Blood, 100:1410-1416 (2002).
Lee et al., "New HLA Nomenclature and Its Clinical Application in Koreans", Korean J Lab Med.;30(3):203 (2010).

\* cited by examiner

Figure 1A
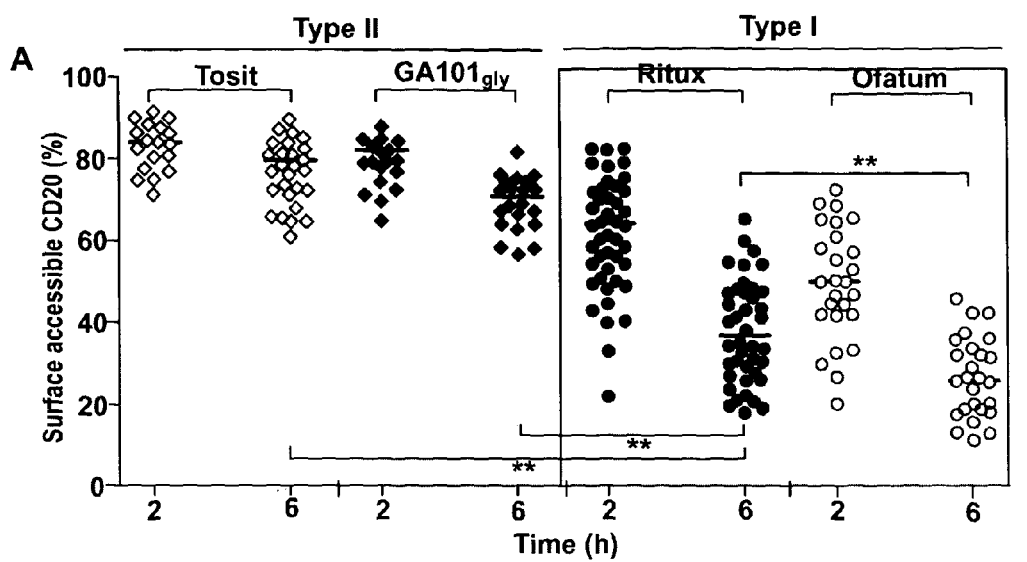
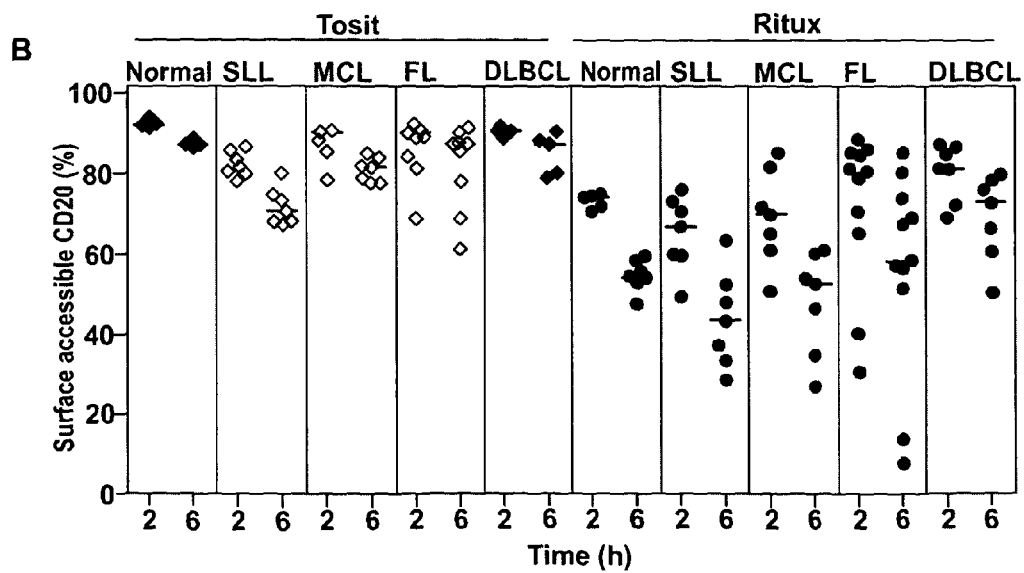
Figure 1B

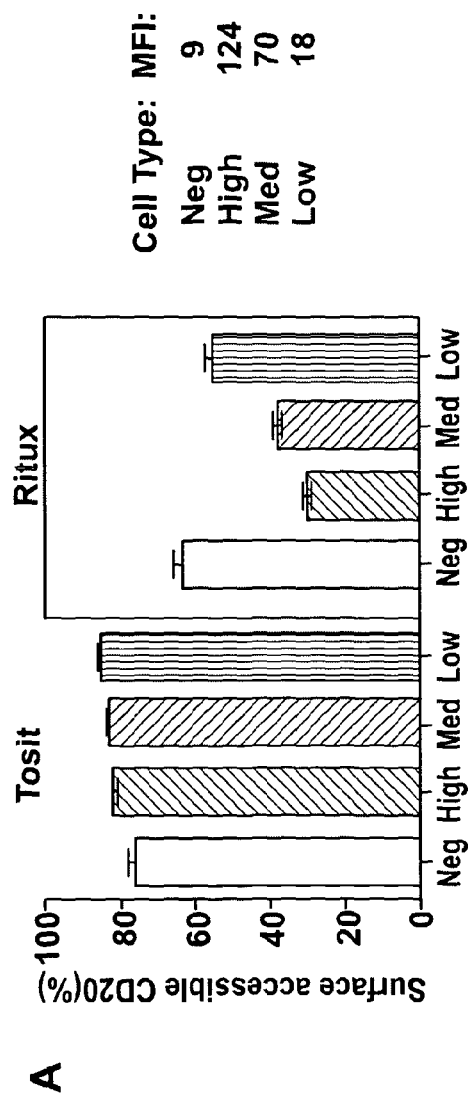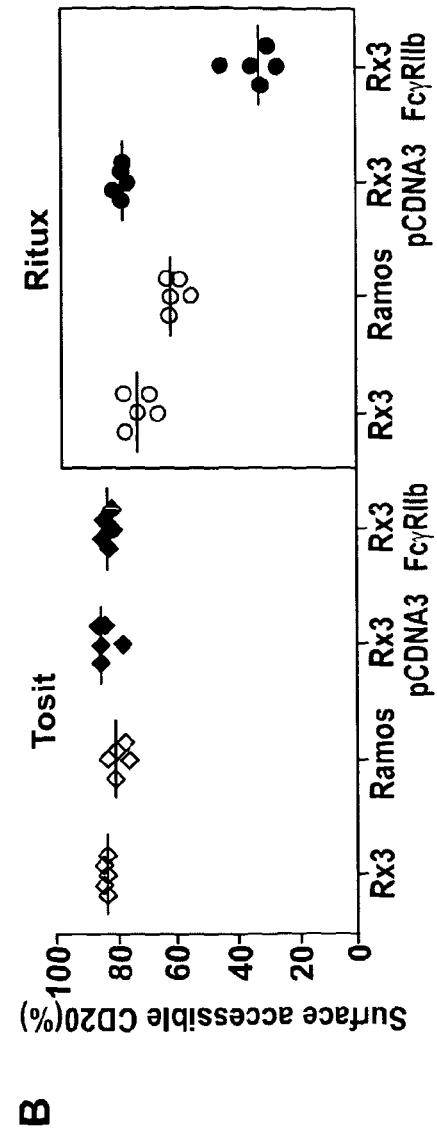
Figure 3A
Figure 3B

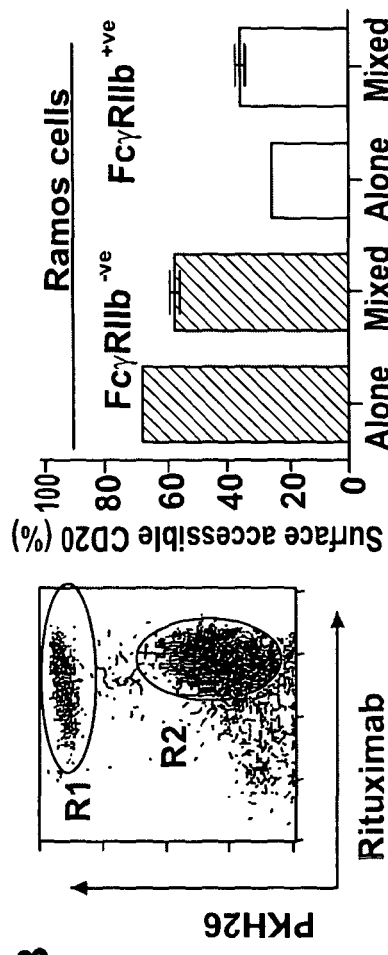
Figure 4A
Figure 4B
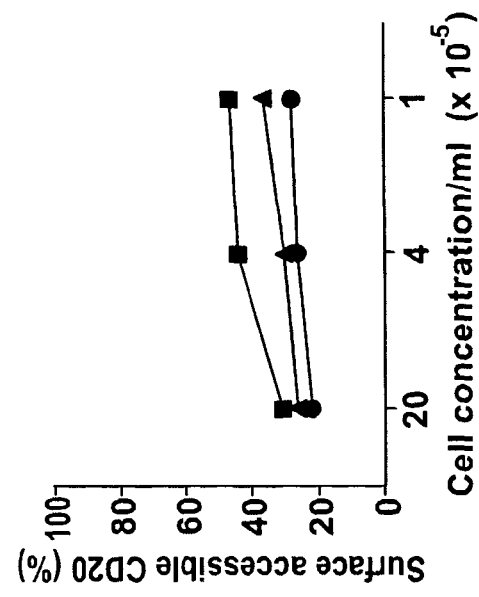
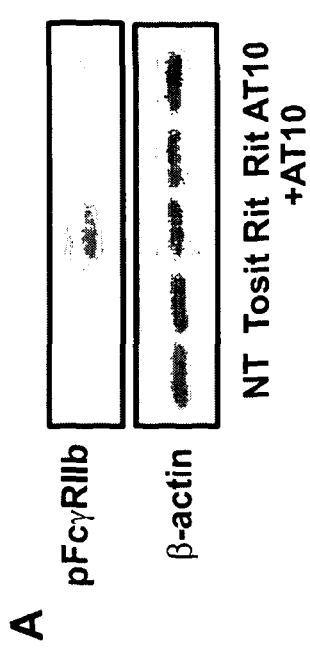
Figure 4C
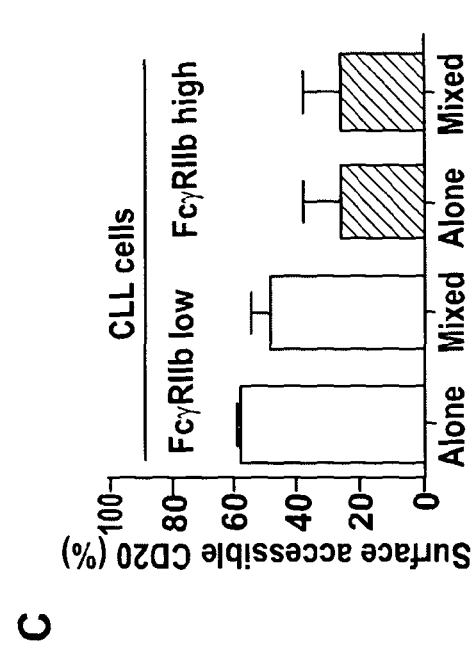
Figure 4D Figure 8
Inhibition of FcgRII with AT10-F(ab')$_2$ increases phagocytic potential of rituximab
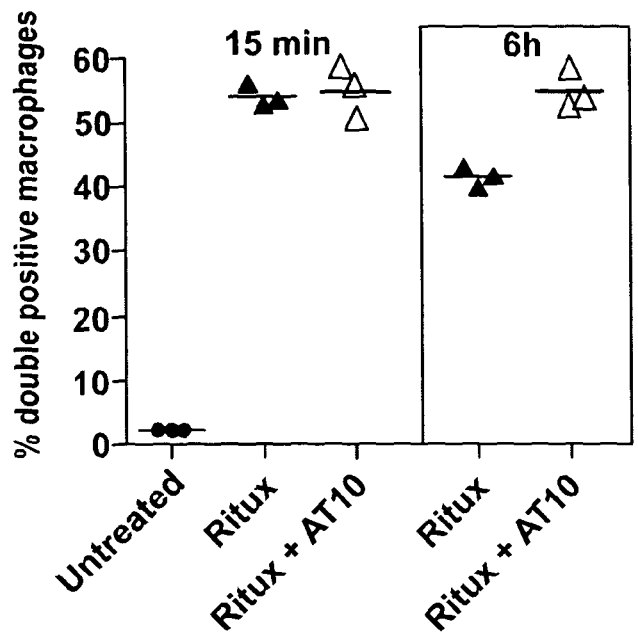
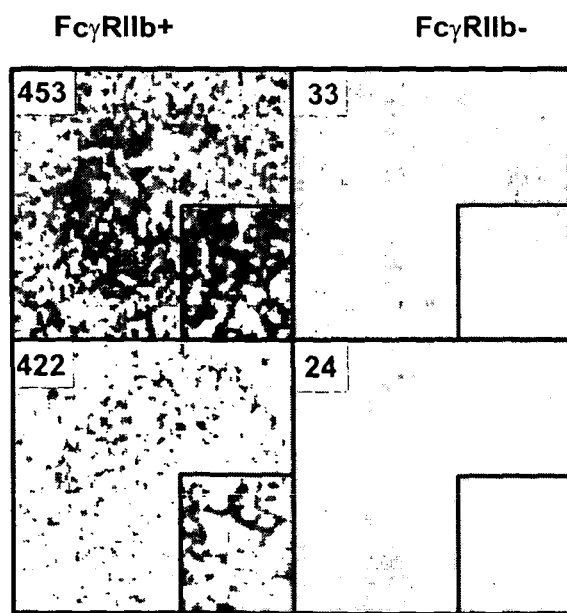
Figure 9

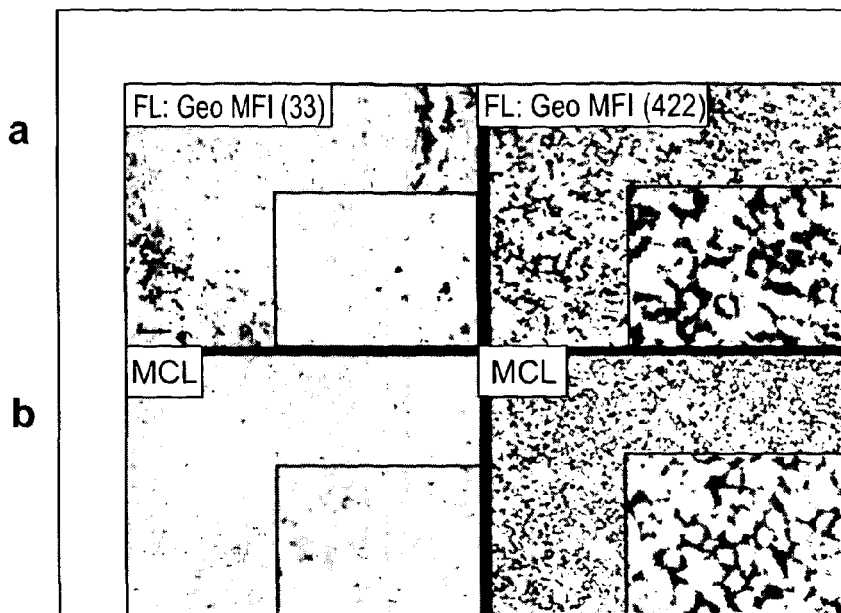
Figure 10A
Figure 10B
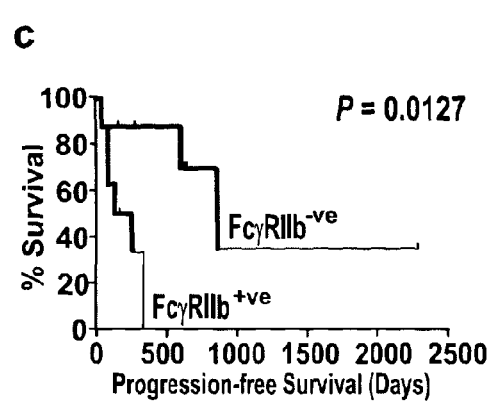
Figure 10C
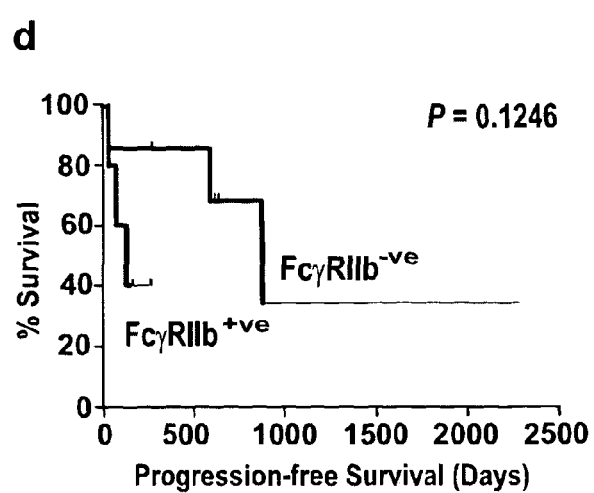
Figure 10D

A

B

Figure 31
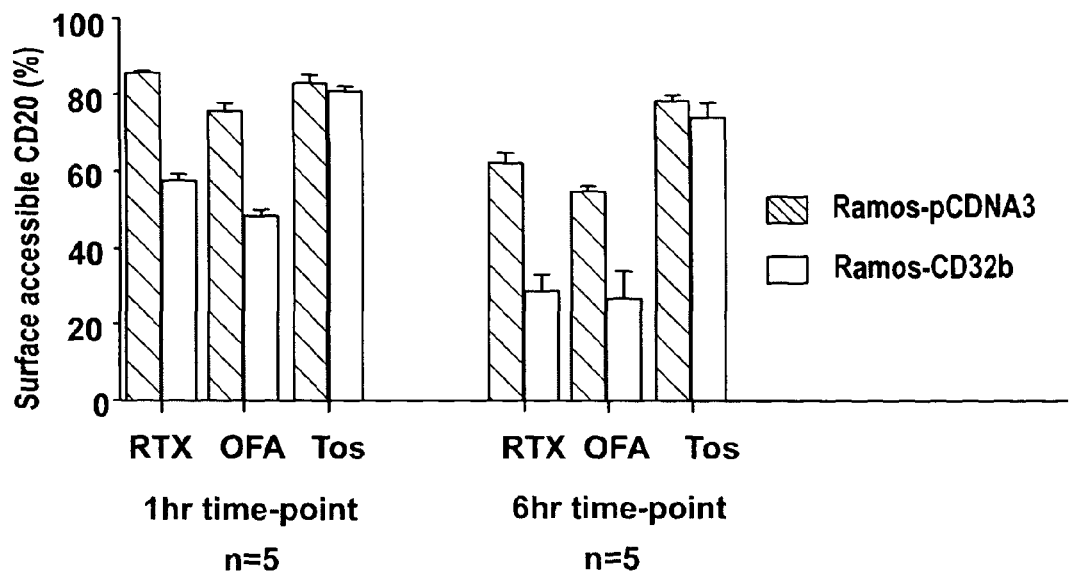
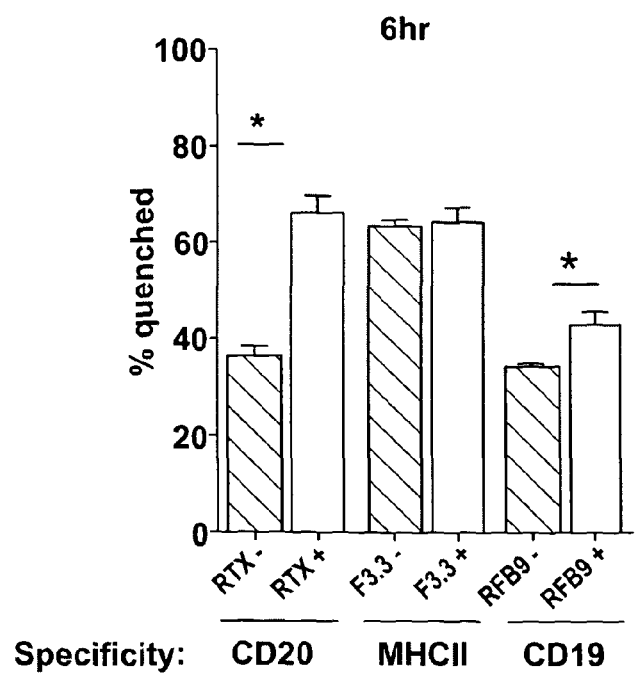
Figure 32

IgG1-CH [SEQ ID NO: 1]
ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAV
EWESNGQPENNYKTTPPVLDSDGSFFLYSKLTVDKSRWQQGNVFSCSVMHE
ALHNHYTQKSLSLSPGK

λ-CL [SEQ ID NO: 2]
QPKAAPSVTLFPPSSEELQANKATLVCLISDFYPGAVTVAWKADSSPVKAGV
ETTTPSKQSNNKYAASSYLSLTPEQWKSHRSYSCQVTHEGSTVEKTVAPTECS

Figure 34

Clone 1

VH [SEQ ID NO: 3]
EVQLLESGGGLVQPGGSLRLSCAASGFTFS NYGMH WVRQAPGKGLEWVA VISYDGSNKYYADSVKG RF
            FrH1                CDRH1         FrH2             CDRH2
TISRDNSKNTLYLQMNSLRAEDTAVYYCAR EWRDAFDI WGQGTLVTVSS
            FrH                CDRH3     FrH4

-VL [SEQ ID NO: 16]
QSVLTQPPSASGTPGQRVTISC TGSSSNIGAGYDVH WYQQLPGTAPKLLIY SDNQRPS GVPDRFSGSKSG
        FrL1            CDRL1          FrL2            CDRL2      FrL3
TSASLAISGLRSEDEADYYC AAWDDSLSGSWV FGGGTKLTVLG
                     CDRL3        FrL4

CDR Regions

CDRH1: NYGMH [SEQ ID NO: 29]
CDRH2: VISYDGSNKYYADSVKG [SEQ ID NO: 30]
CDRH3: EWRDAFDI [SEQ ID NO: 31]

CDRL1: TGSSSNIGAGYDVH [SEQ ID NO: 32]
CDRL2: SDNQRPS [SEQ ID NO: 33]
CDRL3: AAWDDSLSGSWV [SEQ ID NO: 34]

Figure 35

Clone 2

-VH [SEQ ID NO: 4]
EVQLLESGGGLVQPGGSLRLSCAASGFTFS TYGMH WVRQAPGKGLEWVA VIAYDGSKKDYADSVKG RF
TISRDNSKNTLYLQMNSLRAEDTAVYYCAR EYRDAFDI WGQGTLVTVSS

-VL [SEQ ID NO: 17]
QSVLTQPPSASGTPGQRVTISC TGSSSNIGAGYDVH WYQQLPGTAPKLLIY GNSNRPS GVPDRFSGSKSG
TTASLAISGLRSEDEADYYC AAWDDSVSGWM FGGGTKLTVLG

CDR Regions

CDRH1: TYGMH [SEQ ID NO: 35]
CDRH2: VIAYDGSKKDYADSVKG [SEQ ID NO: 36]
CDRH3: EYRDAFDI [SEQ ID NO: 37]

CDRL1: TGSSSNIGAGYDVH [SEQ ID NO: 38]
CDRL2: GNSNRPS [SEQ ID NO: 39]
CDRL3: AAWDDSVSGWM [SEQ ID NO: 40]

Figure 36

Clone 3

-VH [SEQ ID NO: 5]
EVQLLESGGGLVQPGGSLRLSCAASGFTFN NYGMH WVRQAPGKGLEWVA VISYDGSNRYYADSVKG R
FTMSRDNSKNTLYLQMNSLRAEDTAVYYCAR DRWNGMDV WGQGTLVTVSS

-VL [SEQ ID NO: 18]
QSVLTQPPSASGTPGQRVTISC SGSSSNIGAGYDVH WYQQLPGTAPKLLIY ANNQRPS GVPDRFSGSKS
GTSASLAISGLRSEDEADYYC AAWDDSLNGPWV FGGGTKLTVLG

CDR Regions

CDRH1: NYGMH [SEQ ID NO: 41]
CDRH2: VISYDGSNRYYADSVKG [SEQ ID NO: 42]
CDRH3: DRWNGMDV [SEQ ID NO: 43]

CDRL1: SGSSSNIGAGYDVH [SEQ ID NO: 44]
CDRL2: ANNQRPS [SEQ ID NO: 45]
CDRL3: AAWDDSLNGPWV [SEQ ID NO: 46]

Figure 37

Clone 4

-VH [SEQ ID NO: 6]
EVQLLESGGGLVQPGGSLRLSCAASGFTFSSYGMHWVRQAPGKGLEWVAVISYDGSDTAYADSVKGRF
TISRDNSKNTLYLQMNSLRAEDTAVYYCARDHSVIGAFDIWGQGTLVTVSS

-VL [SEQ ID NO: 19]
QSVLTQPPSASGTPGQRVTISCSGSSSNIGSNTVNWYQQLPGTAPKLLIYDNNKRPSGVPDRFSGSKSGT
SASLAISGLRSEDEADYYCSSYAGSNNVVFGGGTKLTVLG

CDR Regions

CDRH1: SYGMH [SEQ ID NO: 47]
CDRH2: VISYDGSDTAYADSVKG [SEQ ID NO: 48]
CDRH3: DHSVIGAFDI [SEQ ID NO: 49]

CDRL1: SGSSSNIGSNTVN [SEQ ID NO: 50]
CDRL2: DNNKRPS [SEQ ID NO: 51]
CDRL3: SSYAGSNNVV [SEQ ID NO: 52]

Figure 38

Clone 5

-VH [SEQ ID NO: 7]
EVQLLESGGGLVQPGGSLRLSCAASGFTFSNYGMHWVRQAPGKGLEWVAVISYDGSNKYYADSVKGRF
TISRDNSKNTLYLQMNSLRAEDTAVYYCARDQLGEAFDIWGQGTLVTVSS

-VL [SEQ ID NO: 20]
QSVLTQPPSASGTPGQRVTISCTGSSSNIGAGYDVHWYQQLPGTAPKLLYDNNKRPSGVPDRFSGSKSG
TSASLAISGLRSEDEADYYCATWDDSLSGPVFGGGTKLTVLG

CDR Regions

CDRH1: NYGMH [SEQ ID NO: 53]
CDRH2: VISYDGSNKYYADSVKG [SEQ ID NO: 54]
CDRH3: DQLGEAFDI [SEQ ID NO: 55]

CDRL1: TGSSSNIGAGYDVH [SEQ ID NO: 56]
CDRL2: DNNKRPS [SEQ ID NO: 57]
CDRL3: ATWDDSLSGPV [SEQ ID NO: 58]

Figure 39

Clone 6

-VH [SEQ ID NO: 8]
EVQLLESGGGLVQPGGSLRLSCAASGFTFD DYGMS WVRQAPGKGLEWVS AISGSGSSTYYADSVKG RF
TISRDNSKNTLYLQMNSLRAEDTAVYYCAG GDIDYFDY WGQGTLVTVSS

-VL [SEQ ID NO: 21]
QSVLTQPPSASGTPGQRVTISC TGSSSNFGAGYDVH WYQQLPGTAPKLLIY ENNKRPS GVPDRFSGSKS
GTSASLAISGLRSEDEADYYC AAWDDSLNGPV FGGGTKLTVLG

CDR Regions

CDRH1: DYGMS [SEQ ID NO: 59]
CDRH2: AISGSGSSTYYADSVKG [SEQ ID NO: 60]
CDRH3: GDIDYFDY [SEQ ID NO: 61]

CDRL1: TGSSSNFGAGYDVH [SEQ ID NO: 62]
CDRL2: ENNKRPS [SEQ ID NO: 63]
CDRL3: AAWDDSLNGPV [SEQ ID NO: 64]

Figure 40

Clone 7

-VH [SEQ ID NO: 9]
EVQLLESGGGLVQPGGSLRLSCAASGFTFS SYGMH WVRQAPGKGLEWVA VISYDGSNKYYADSVKG RF
TISRDNSKNTLYLQMNSLRAEDTAVYYCAR ERRDAFDI WGQGTLVTVSS

-VL [SEQ ID NO: 22]
QSVLTQPPSASGTPGQRVTISC TGSSSNIGAGYDVH WYQQLPGTAPKLLIY SDNQRPS GVPDRFSGSKSG
TSASLAISGLRSEDEADYYC ATWDSDTPV FGGGTKLTVLG

CDR Regions

CDRH1: SYGMH [SEQ ID NO: 65]
CDRH2: VISYDGSNKYYADSVKG [SEQ ID NO: 66]
CDRH3: ERRDAFDI [SEQ ID NO: 67]

CDRL1: TGSSSNIGAGYDVH [SEQ ID NO: 68]
CDRL2: SDNQRPS [SEQ ID NO: 69]
CDRL3: ATWDSDTPV [SEQ ID NO: 70]

Figure 41

Clone 8

-VH [SEQ ID NO: 10]
EVQLLESGGGLVQPGGSLRLSCAASGFTFS SYGMH WVRQAPGKGLEWVA VISYDGSNKYYADSVKG RF
TISRDNSKNTLYLQMNSLRAEDTAMYYCAR DHSAAGYFDY WGQGTLVTVSS

-VL [SEQ ID NO: 23]
QSVLTQPPSASGTPGQRVTISC SGSSSNIGSNTVN WYQQLPGTAPKLLIY GNSIRPS GGPDRFSGSKSGTS
ASLAISGLRSEDEADYYC ASWDDSLSSPV FGGGTKLTVLG

CDR Regions

CDRH1: SYGMH [SEQ ID NO: 71]
CDRH2: VISYDGSNKYYADSVKG [SEQ ID NO: 72]
CDRH3: DHSAAGYFDY [SEQ ID NO: 73]

CDRL1: SGSSSNIGSNTVN [SEQ ID NO: 74]
CDRL2: GNSIRPS [SEQ ID NO: 75]
CDRL3: ASWDDSLSSPV [SEQ ID NO: 76]

Figure 42

Clone 9

-VH [SEQ ID NO: 11]
EVQLLESGGGLVQPGGSLRLSCAASGFTFG SYGMH WVRQAPGKGLEWVS GISWDSAIIDYAGSVKG RF
TISRDNSKNTLYLQMNSLRAEDTAVYYCAK DEAAAGAFDI WGQGTLVTVSS

-VL [SEQ ID NO: 24]
QSVLTQPPSASGTPGQRVTISC TGSSSNIGAGYDVH WYQQLPGTAPKLLIY GNTDRPS GVPDRFSGSKSG
TSASLAISGLRSEDEADYYC AAWDDSLSGPVV FGGGTKLTVLG

CDR Regions

CDRH1: SYGMH [SEQ ID NO: 77]
CDRH2: GISWDSAIIDYAGSVKG [SEQ ID NO: 78]
CDRH3: DEAAAGAFDI [SEQ ID NO: 79]

CDRL1: TGSSSNIGAGYDVH [SEQ ID NO: 80]
CDRL2: GNTDRPS [SEQ ID NO: 81]
CDRL3: AAWDDSLSGPVV [SEQ ID NO: 82]

Figure 43

Clone 10

-VH [SEQ ID NO: 12]
EVQLLESGGGLVQPGGSLRLSCAASGFTFS SYGMH WVRQAPGKGLEWMA VISYDGSNKYYADSVKG R
FTISRDNSKNTLYLQMNSLRAEDTAVYYCAR ELYDAFDI WGQGTLVTVSS

-VL [SEQ ID NO: 25]
QSVLTQPPSASGTPGQRVTISC TGSSSNIGAGYDVH WYQQLPGTAPKLLIY ADDHRPS GVPDRFSGSKSG
TSASLAISGLRSEDEADYYC ASWDDSQRAVI FGGGTKLTVLG

CDR Regions

CDRH1: SYGMH [SEQ ID NO: 83]
CDRH2: VISYDGSNKYYADSVKG [SEQ ID NO: 84]
CDRH3: ELYDAFDI [SEQ ID NO: 85]

CDRL1: TGSSSNIGAGYDVH [SEQ ID NO: 86]
CDRL2: ADDHRPS [SEQ ID NO: 87]
CDRL3: ASWDDSQRAVI [SEQ ID NO: 88]

Figure 44

Clone 11

-VH [SEQ ID NO: 13]
EVQLLESGGGLVQPGGSLRLSCAASGFTFS SYGMH WVRQAPGKGLEWVA VISYDGSNKYYADSVKG RF
TISRDNSQNTLYLQMNSLRAEDTAVYYCAR EFGYIILDY WGQGTLVTVSS

-VL [SEQ ID NO: 26]
QSVLTQPPSASGTPGQRVTISC SGSSSNIGSNTVN WYQQLPGTAPKLLIY RDYERPS GVPDRFSGSKSGTS
ASLAISGLRSEDEADYYC MAWDDSLSGVV FGGGTKLTVLG

CDR Regions

CDRH1: SYGMH [SEQ ID NO: 89]
CDRH2: VISYDGSNKYYADSVKG [SEQ ID NO: 90]
CDRH3: EFGYIILDY [SEQ ID NO: 91]

CDRL1: SGSSSNIGSNTVN [SEQ ID NO: 92]
CDRL2: RDYERPS [SEQ ID NO: 93]
CDRL3: MAWDDSLSGVV [SEQ ID NO: 94]

Figure 45

Clone 12

-VH [SEQ ID NO: 14]
EVQLLESGGGLVQPGGSLRLSCAASGFTFS NHGMH WVRQAPGKGLEWVA VISYDGTNKYYADSVRG R
FTISRDNSKNTLYLQMNSLRAEDTAVYYCAR ETWDAFDV WGQGTLVTVSS

-VL [SEQ ID NO: 27]
QSVLTQPPSASGTPGQRVTISC SGSSSNIGSNNAN WYQQLPGTAPKLLIY DNNKRPS GVPDRFSGSKSGT
SASLAISGLRSEDEADYYC QAWDSSTVV FGGGTKLTVLG

CDR Regions

CDRH1: NHGMH [SEQ ID NO: 95]
CDRH2: VISYDGTNKYYADSVRG [SEQ ID NO: 96]
CDRH3: ETWDAFDV [SEQ ID NO: 97]

CDRL1: SGSSSNIGSNNAN [SEQ ID NO: 98]
CDRL2: DNNKRPS [SEQ ID NO: 99]
CDRL3: QAWDSSTVV [SEQ ID NO: 100]

Figure 46

Clone 13

-VH [SEQ ID NO: 15]
EVQLLESGGGLVQPGGSLRLSCAASGFTLS SYGIS WVRQAPGKGLEWVS GISGSGGNTYYADSVKG RFTI
SRDNSKNTLYLQMNSLRAEDTAVYYCAS SVGAYANDAFDI WGQGTLVTVSS

-VL [SEQ ID NO: 28]
QSVLTQPPSASGTPGQRVTISC TGSSSNIGAGYDVH WYQQLPGTAPKLLIY GDTNRPS GVPDRFSGSKSG
TSASLAISGLRSEDEADYYC AAWDDSLNGPV FGGGTKLTVLG

CDR Regions

CDRH1: SYGIS [SEQ ID NO: 101]
CDRH2: GISGSGGNTYYADSVKG [SEQ ID NO: 102]
CDRH3: SVGAYANDAFDI [SEQ ID NO: 103]

CDRL1: TGSSSNIGAGYDVH [SEQ ID NO: 104]
CDRL2: GDTNRPS [SEQ ID NO: 105]
CDRL3: AAWDDSLNGPV [SEQ ID NO: 106]

Figure 47

SEQUENCE LISTING

<160> NUMBER OF SEQ ID NOS: 106

<210> SEQ ID NO 1
<211> LENGTH: 330
<212> TYPE: PRT
<213> ORGANISM: Artificial Sequence
<220> FEATURE:
<223> OTHER INFORMATION: CH region

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

-continued

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 105
<212> TYPE: PRT
<213> ORGANISM: Artificial Sequence
<220> FEATURE:
<223> OTHER INFORMATION: CL Region

<400> SEQUENCE: 2

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 3
<211> LENGTH: 117
<212> TYPE: PRT
<213> ORGANISM: Artificial Sequence
<220> FEATURE:
<223> OTHER INFORMATION: Clone 1 VH region

<400> SEQUENCE: 3
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Arg Asp Ala Phe Asp Ile Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Clone 2 VH region

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ala Tyr Asp Gly Ser Lys Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Arg Asp Ala Phe Asp Ile Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Clone 3 VH region

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Arg Tyr Tyr Ala Asp Ser Val
```

```
                    50                  55                  60
Lys Gly Arg Phe Thr Met Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asp Arg Trp Asn Gly Met Asp Val Trp Gly Gln Gly Thr Leu
                    100                 105                 110

Val Thr Val Ser Ser
            115

<210> SEQ ID NO 6
<211> LENGTH: 119
<212> TYPE: PRT
<213> ORGANISM: Artificial Sequence
<220> FEATURE:
<223> OTHER INFORMATION: Clone 4 VH region

<400> SEQUENCE: 6

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
                35                  40                  45

Ala Val Ile Ser Tyr Asp Gly Ser Asp Thr Ala Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asp His Ser Val Ile Gly Ala Phe Asp Ile Trp Gly Gln Gly
                    100                 105                 110

Thr Leu Val Thr Val Ser Ser
            115

<210> SEQ ID NO 7
<211> LENGTH: 118
<212> TYPE: PRT
<213> ORGANISM: Artificial Sequence
<220> FEATURE:
<223> OTHER INFORMATION: Clone 5 VH region

<400> SEQUENCE: 7

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Asn Tyr
                    20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asp Gln Leu Gly Glu Ala Phe Asp Ile Trp Gly Gln Gly Thr
                    100                 105                 110
```

```
Leu Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: Clone 6 VH region

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp Ile Asp Tyr Phe Asp Tyr Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: Clone 7 VH region

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Arg Asp Ala Phe Asp Ile Trp Gly Gln Gly Thr Leu
            100                 105                 110

Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Clone 8 VH region
```

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp His Ser Ala Ala Gly Tyr Phe Asp Tyr Trp Gly Gln Gly
            100                 105                 110

Thr Leu Val Thr Val Ser Ser
            115

<210> SEQ ID NO 11
<211> LENGTH: 119
<212> TYPE: PRT
<213> ORGANISM: Artificial Sequence
<220> FEATURE:
<223> OTHER INFORMATION: Clone 9 VH region

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ser Gly Ile Ser Trp Asp Ser Ala Ile Ile Asp Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Ala Ala Ala Gly Ala Phe Asp Ile Trp Gly Gln Gly
            100                 105                 110

Thr Leu Val Thr Val Ser Ser
            115

<210> SEQ ID NO 12
<211> LENGTH: 117
<212> TYPE: PRT
<213> ORGANISM: Artificial Sequence
<220> FEATURE:
<223> OTHER INFORMATION: Clone 10 VH region

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

```
Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Leu Tyr Asp Ala Phe Asp Ile Trp Gly Gln Gly Thr Leu
                100                 105                 110

Val Thr Val Ser Ser
            115

<210> SEQ ID NO 13
<211> LENGTH: 118
<212> TYPE: PRT
<213> ORGANISM: Artificial Sequence
<220> FEATURE:
<223> OTHER INFORMATION: Clone 11 VH region

<400> SEQUENCE: 13

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Gln Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Phe Gly Tyr Ile Ile Leu Asp Tyr Trp Gly Gln Gly Thr
                100                 105                 110

Leu Val Thr Val Ser Ser
            115

<210> SEQ ID NO 14
<211> LENGTH: 117
<212> TYPE: PRT
<213> ORGANISM: Artificial Sequence
<220> FEATURE:
<223> OTHER INFORMATION: Clone 12 VH region

<400> SEQUENCE: 14

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
                20                  25                  30

Gly Met His Trp Val Arg Gln Ala Pro Gly Lys Gly Leu Glu Trp Val
            35                  40                  45

Ala Val Ile Ser Tyr Asp Gly Thr Asn Lys Tyr Tyr Ala Asp Ser Val
            50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Thr Trp Asp Ala Phe Asp Val Trp Gly Gln Gly Thr Leu
                100                 105                 110
```

Val Thr Val Ser Ser
        115

<210> SEQ ID NO 15
<211> LENGTH: 121
<212> TYPE: PRT
<213> ORGANISM: Artificial Sequence
<220> FEATURE:
<223> OTHER INFORMATION: Clone 13 VH region

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Gly Ile Ser Trp Val Arg Gln Ala Pro Gly Lys Gly Leu Glu Trp Val
        35                  40                  45

Ser Gly Ile Ser Gly Ser Gly Gly Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Val Gly Ala Tyr Ala Asn Asp Ala Phe Asp Ile Trp Gly
            100                 105                 110

Gln Gly Thr Leu Val Thr Val Ser Ser
        115                 120

<210> SEQ ID NO 16
<211> LENGTH: 113
<212> TYPE: PRT
<213> ORGANISM: Artificial Sequence
<220> FEATURE:
<223> OTHER INFORMATION: Clone 1 VL region

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ser Asp Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Ser Gly Ser Trp Val Phe Gly Gly Gly Thr Lys Leu Thr Val Leu
            100                 105                 110

Gly

<210> SEQ ID NO 17
<211> LENGTH: 112
<212> TYPE: PRT
<213> ORGANISM: Artificial Sequence
<220> FEATURE:
<223> OTHER INFORMATION: Clone 2 VL region

```
<400> SEQUENCE: 17

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Thr Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Val Ser Gly Trp Met Phe Gly Gly Gly Thr Lys Leu Thr Val Leu Gly
            100                 105                 110

<210> SEQ ID NO 18
<211> LENGTH: 113
<212> TYPE: PRT
<213> ORGANISM: Artificial Sequence
<220> FEATURE:
<223> OTHER INFORMATION: Clone 3 VL region

<400> SEQUENCE: 18

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Ala Asn Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Trp Val Phe Gly Gly Gly Thr Lys Leu Thr Val Leu
            100                 105                 110

Gly

<210> SEQ ID NO 19
<211> LENGTH: 110
<212> TYPE: PRT
<213> ORGANISM: Artificial Sequence
<220> FEATURE:
<223> OTHER INFORMATION: Clone 4 VL region

<400> SEQUENCE: 19

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
```

```
                65                  70                  75                  80
Ser Glu Asp Glu Ala Asp Tyr Tyr Cys Ser Ser Tyr Ala Gly Ser Asn
                    85                  90                  95

Asn Val Val Phe Gly Gly Gly Thr Lys Leu Thr Val Leu Gly
                100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Clone 5 VL region

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Asp Ser
                85                  90                  95

Leu Ser Gly Pro Val Phe Gly Gly Gly Thr Lys Leu Thr Val Leu Gly
                100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Clone 6 VL region

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Phe Gly Ala Gly
                20                  25                  30

Tyr Asp Val His Trp Tyr Gln Gln Leu Pro Gly Thr Ala Pro Lys Leu
            35                  40                  45

Leu Ile Tyr Glu Asn Asn Lys Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Val Phe Gly Gly Gly Thr Lys Leu Thr Val Leu Gly
                100                 105                 110

<210> SEQ ID NO 22
<211> LENGTH: 110
<212> TYPE: PRT
<213> ORGANISM: Artificial Sequence
<220> FEATURE:
<223> OTHER INFORMATION: Clone 7 VL region

<400> SEQUENCE: 22
```

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Ser Asp Asn Gln Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Thr Trp Asp Ser Asp
                85                  90                  95

Thr Pro Val Phe Gly Gly Gly Thr Lys Leu Thr Val Leu Gly
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Clone 8 VL region

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Ser Ile Arg Pro Ser Gly Gly Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ser Pro Val Phe Gly Gly Gly Thr Lys Leu Thr Val Leu Gly
            100                 105                 110

<210> SEQ ID NO 24
<211> LENGTH: 113
<212> TYPE: PRT
<213> ORGANISM: Artificial Sequence
<220> FEATURE:
<223> OTHER INFORMATION: Clone 9 VL region

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Thr Asp Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
```

85                  90                  95

Leu Ser Gly Pro Val Val Phe Gly Gly Gly Thr Lys Leu Thr Val Leu
            100                 105                 110

Gly

<210> SEQ ID NO 25
<211> LENGTH: 112
<212> TYPE: PRT
<213> ORGANISM: Artificial Sequence
<220> FEATURE:
<223> OTHER INFORMATION: Clone 10 VL region

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Asp His Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ser Trp Asp Asp Ser
                85                  90                  95

Gln Arg Ala Val Ile Phe Gly Gly Gly Thr Lys Leu Thr Val Leu Gly
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: Clone 11 VL region

<400> SEQUENCE: 26

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asp Tyr Glu Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Met Ala Trp Asp Asp Ser Leu
                85                  90                  95

Ser Gly Val Val Phe Gly Gly Gly Thr Lys Leu Thr Val Leu Gly
            100                 105                 110

<210> SEQ ID NO 27
<211> LENGTH: 109
<212> TYPE: PRT
<213> ORGANISM: Artificial Sequence
<220> FEATURE:
<223> OTHER INFORMATION: Clone 12 VL region

<400> SEQUENCE: 27

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asn Ala Asn Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ala Trp Asp Ser Ser Thr
                85                  90                  95

Val Val Phe Gly Gly Gly Thr Lys Leu Thr Val Leu Gly
            100                 105
```

<210> SEQ ID NO 28
<211> LENGTH: 112
<212> TYPE: PRT
<213> ORGANISM: Artificial Sequence
<220> FEATURE:
<223> OTHER INFORMATION: Clone 13 VL region

<400> SEQUENCE: 28

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Leu Asn Gly Pro Val Phe Gly Gly Gly Thr Lys Leu Thr Val Leu Gly
            100                 105                 110
```

<210> SEQ ID NO 29
<211> LENGTH: 5
<212> TYPE: PRT
<213> ORGANISM: Artificial Sequence
<220> FEATURE:
<223> OTHER INFORMATION: Clone 1 CDRH1

<400> SEQUENCE: 29

```
Asn Tyr Gly Met His
1               5
```

<210> SEQ ID NO 30
<211> LENGTH: 17
<212> TYPE: PRT
<213> ORGANISM: Artificial Sequence
<220> FEATURE:
<223> OTHER INFORMATION: Clone 1 CDRH2

<400> SEQUENCE: 30

```
Val Ile Ser Tyr Asp Gly Ser Asn Lys Tyr Tyr Ala Asp Ser Val Lys
1               5                   10                  15

Gly
```

<210> SEQ ID NO 31
<211> LENGTH: 8
<212> TYPE: PRT
<213> ORGANISM: Artificial Sequence
<220> FEATURE:
<223> OTHER INFORMATION: Clone 1 CDRH3

<400> SEQUENCE: 31

Glu Trp Arg Asp Ala Phe Asp Ile
1               5

<210> SEQ ID NO 32
<211> LENGTH: 14
<212> TYPE: PRT
<213> ORGANISM: Artificial Sequence
<220> FEATURE:
<223> OTHER INFORMATION: Clone 1 CDRL1

<400> SEQUENCE: 32

Thr Gly Ser Ser Ser Asn Ile Gly Ala Gly Tyr Asp Val His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Clone 1 CDRL2

<400> SEQUENCE: 33

Ser Asp Asn Gln Arg Pro Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Clone 1 CDRL3

<400> SEQUENCE: 34

Ala Ala Trp Asp Asp Ser Leu Ser Gly Ser Trp Val
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Clone 2 CDRH1

<400> SEQUENCE: 35

Thr Tyr Gly Met His
1               5

<210> SEQ ID NO 36
<211> LENGTH: 17
<212> TYPE: PRT
<213> ORGANISM: Artificial Sequence
<220> FEATURE:
<223> OTHER INFORMATION: Clone 2 CDRH2

<400> SEQUENCE: 36

Val Ile Ala Tyr Asp Gly Ser Lys Lys Asp Tyr Ala Asp Ser Val Lys
1               5                   10                  15

Gly

<210> SEQ ID NO 37
<211> LENGTH: 8
<212> TYPE: PRT
<213> ORGANISM: Artificial Sequence
<220> FEATURE:
<223> OTHER INFORMATION: Clone 2 CDRH3

<400> SEQUENCE: 37

Glu Tyr Arg Asp Ala Phe Asp Ile
1               5

<210> SEQ ID NO 38
<211> LENGTH: 14
<212> TYPE: PRT
<213> ORGANISM: Artificial Sequence
<220> FEATURE:
<223> OTHER INFORMATION: Clone 2 CDRL1

<400> SEQUENCE: 38

Thr Gly Ser Ser Ser Asn Ile Gly Ala Gly Tyr Asp Val His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Clone 2 CDRL2

<400> SEQUENCE: 39

Gly Asn Ser Asn Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Clone 2 CDRL3

<400> SEQUENCE: 40

Ala Ala Trp Asp Asp Ser Val Ser Gly Trp Met
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Clone 3 CDRH1

<400> SEQUENCE: 41

Asn Tyr Gly Met His
1               5

<210> SEQ ID NO 42
<211> LENGTH: 17
<212> TYPE: PRT
<213> ORGANISM: Artificial Sequence
<220> FEATURE:
<223> OTHER INFORMATION: Clone 3 CDRH2

<400> SEQUENCE: 42

Val Ile Ser Tyr Asp Gly Ser Asn Arg Tyr Tyr Ala Asp Ser Val Lys
1               5                   10                  15

Gly

<210> SEQ ID NO 43
<211> LENGTH: 8
<212> TYPE: PRT
<213> ORGANISM: Artificial Sequence
<220> FEATURE:
<223> OTHER INFORMATION: Clone 3 CDRH3

<400> SEQUENCE: 43

Asp Arg Trp Asn Gly Met Asp Val
1               5

<210> SEQ ID NO 44
<211> LENGTH: 14
<212> TYPE: PRT
<213> ORGANISM: Artificial Sequence
<220> FEATURE:
<223> OTHER INFORMATION: Clone 3 CDRL1

<400> SEQUENCE: 44

Ser Gly Ser Ser Ser Asn Ile Gly Ala Gly Tyr Asp Val His
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Clone 3 CDRL2

<400> SEQUENCE: 45

Ala Asn Asn Gln Arg Pro Ser
1               5

<210> SEQ ID NO 46
<211> LENGTH: 12
<212> TYPE: PRT
<213> ORGANISM: Artificial Sequence
<220> FEATURE:
<223> OTHER INFORMATION: Clone 3 CDRL3

<400> SEQUENCE: 46

Ala Ala Trp Asp Asp Ser Leu Asn Gly Pro Trp Val
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Clone 4 CDRH1

<400> SEQUENCE: 47

Ser Tyr Gly Met His
1               5

<210> SEQ ID NO 48
<211> LENGTH: 17
<212> TYPE: PRT
<213> ORGANISM: Artificial Sequence
<220> FEATURE:
<223> OTHER INFORMATION: Clone 4 CDRH2

<400> SEQUENCE: 48

Val Ile Ser Tyr Asp Gly Ser Asp Thr Ala Tyr Ala Asp Ser Val Lys

```
1               5                   10                  15

Gly

<210> SEQ ID NO 49
<211> LENGTH: 10
<212> TYPE: PRT
<213> ORGANISM: Artificial Sequence
<220> FEATURE:
<223> OTHER INFORMATION: Clone 4 CDRH3

<400> SEQUENCE: 49

Asp His Ser Val Ile Gly Ala Phe Asp Ile
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Clone 4 CDRL1

<400> SEQUENCE: 50

Ser Gly Ser Ser Ser Asn Ile Gly Ser Asn Thr Val Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Clone 4 CDRL2

<400> SEQUENCE: 51

Asp Asn Asn Lys Arg Pro Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Clone 4 CDRL3

<400> SEQUENCE: 52

Ser Ser Tyr Ala Gly Ser Asn Asn Val Val
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Clone 5 CDRH1

<400> SEQUENCE: 53

Asn Tyr Gly Met His
1               5

<210> SEQ ID NO 54
<211> LENGTH: 17
<212> TYPE: PRT
<213> ORGANISM: Artificial Sequence
<220> FEATURE:
<223> OTHER INFORMATION: Clone 5 CDRH2

<400> SEQUENCE: 54
```

```
Val Ile Ser Tyr Asp Gly Ser Asn Lys Tyr Tyr Ala Asp Ser Val Lys
1               5                   10                  15

Gly

<210> SEQ ID NO 55
<211> LENGTH: 9
<212> TYPE: PRT
<213> ORGANISM: Artificial Sequence
<220> FEATURE:
<223> OTHER INFORMATION: Clone 5 CDRH3

<400> SEQUENCE: 55

Asp Gln Leu Gly Glu Ala Phe Asp Ile
1               5

<210> SEQ ID NO 56
<211> LENGTH: 14
<212> TYPE: PRT
<213> ORGANISM: Artificial Sequence
<220> FEATURE:
<223> OTHER INFORMATION: Clone 5 CDRL1

<400> SEQUENCE: 56

Thr Gly Ser Ser Ser Asn Ile Gly Ala Gly Tyr Asp Val His
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Clone 5 CDRL2

<400> SEQUENCE: 57

Asp Asn Asn Lys Arg Pro Ser
1               5

<210> SEQ ID NO 58
<211> LENGTH: 11
<212> TYPE: PRT
<213> ORGANISM: Artificial Sequence
<220> FEATURE:
<223> OTHER INFORMATION: Clone 5 CDRL3

<400> SEQUENCE: 58

Ala Thr Trp Asp Asp Ser Leu Ser Gly Pro Val
1               5                   10

<210> SEQ ID NO 59
<211> LENGTH: 5
<212> TYPE: PRT
<213> ORGANISM: Artificial Sequence
<220> FEATURE:
<223> OTHER INFORMATION: Clone 6 CDRH1

<400> SEQUENCE: 59

Asp Tyr Gly Met Ser
1               5

<210> SEQ ID NO 60
<211> LENGTH: 17
<212> TYPE: PRT
<213> ORGANISM: Artificial Sequence
<220> FEATURE:
<223> OTHER INFORMATION: Clone 6 CDRH2

<400> SEQUENCE: 60
```

```
Ala Ile Ser Gly Ser Gly Ser Ser Thr Tyr Tyr Ala Asp Ser Val Lys
1               5                   10                  15
Gly

<210> SEQ ID NO 61
<211> LENGTH: 8
<212> TYPE: PRT
<213> ORGANISM: Artificial Sequence
<220> FEATURE:
<223> OTHER INFORMATION: Clone 6 CDRH3

<400> SEQUENCE: 61

Gly Asp Ile Asp Tyr Phe Asp Tyr
1               5

<210> SEQ ID NO 62
<211> LENGTH: 14
<212> TYPE: PRT
<213> ORGANISM: Artificial Sequence
<220> FEATURE:
<223> OTHER INFORMATION: Clone 6 CDRL1

<400> SEQUENCE: 62

Thr Gly Ser Ser Ser Asn Phe Gly Ala Gly Tyr Asp Val His
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Clone 6 CDRL2

<400> SEQUENCE: 63

Glu Asn Asn Lys Arg Pro Ser
1               5

<210> SEQ ID NO 64
<211> LENGTH: 11
<212> TYPE: PRT
<213> ORGANISM: Artificial Sequence
<220> FEATURE:
<223> OTHER INFORMATION: Clone 6 CDRL3

<400> SEQUENCE: 64

Ala Ala Trp Asp Asp Ser Leu Asn Gly Pro Val
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Clone 7 CDRH1

<400> SEQUENCE: 65

Ser Tyr Gly Met His
1               5

<210> SEQ ID NO 66
<211> LENGTH: 17
<212> TYPE: PRT
<213> ORGANISM: Artificial Sequence
<220> FEATURE:
<223> OTHER INFORMATION: Clone 7 CDRH2
```

```
<400> SEQUENCE: 66

Val Ile Ser Tyr Asp Gly Ser Asn Lys Tyr Tyr Ala Asp Ser Val Lys
1               5                   10                  15

Gly

<210> SEQ ID NO 67
<211> LENGTH: 8
<212> TYPE: PRT
<213> ORGANISM: Artificial Sequence
<220> FEATURE:
<223> OTHER INFORMATION: Clone 7 CDRH3

<400> SEQUENCE: 67

Glu Arg Arg Asp Ala Phe Asp Ile
1               5

<210> SEQ ID NO 68
<211> LENGTH: 14
<212> TYPE: PRT
<213> ORGANISM: Artificial Sequence
<220> FEATURE:
<223> OTHER INFORMATION: Clone 7 CDRL1

<400> SEQUENCE: 68

Thr Gly Ser Ser Ser Asn Ile Gly Ala Gly Tyr Asp Val His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Clone 7 CDRL2

<400> SEQUENCE: 69

Ser Asp Asn Gln Arg Pro Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Clone 7 CDRL3

<400> SEQUENCE: 70

Ala Thr Trp Asp Ser Asp Thr Pro Val
1               5

<210> SEQ ID NO 71
<211> LENGTH: 5
<212> TYPE: PRT
<213> ORGANISM: Artificial Sequence
<220> FEATURE:
<223> OTHER INFORMATION: Clone 8 CDRH1

<400> SEQUENCE: 71

Ser Tyr Gly Met His
1               5

<210> SEQ ID NO 72
<211> LENGTH: 17
<212> TYPE: PRT
<213> ORGANISM: Artificial Sequence
<220> FEATURE:
<223> OTHER INFORMATION: Clone 8 CDRH2
```

<400> SEQUENCE: 72

Val Ile Ser Tyr Asp Gly Ser Asn Lys Tyr Tyr Ala Asp Ser Val Lys
1               5                   10                  15
Gly

<210> SEQ ID NO 73
<211> LENGTH: 10
<212> TYPE: PRT
<213> ORGANISM: Artificial Sequence
<220> FEATURE:
<223> OTHER INFORMATION: Clone 8 CDRH3

<400> SEQUENCE: 73

Asp His Ser Ala Ala Gly Tyr Phe Asp Tyr
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Clone 8 CDRL1

<400> SEQUENCE: 74

Ser Gly Ser Ser Ser Asn Ile Gly Ser Asn Thr Val Asn
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Clone 8 CDRL2

<400> SEQUENCE: 75

Gly Asn Ser Ile Arg Pro Ser
1               5

<210> SEQ ID NO 76
<211> LENGTH: 11
<212> TYPE: PRT
<213> ORGANISM: Artificial Sequence
<220> FEATURE:
<223> OTHER INFORMATION: Clone 8 CDRL3

<400> SEQUENCE: 76

Ala Ser Trp Asp Asp Ser Leu Ser Ser Pro Val
1               5                   10

<210> SEQ ID NO 77
<211> LENGTH: 5
<212> TYPE: PRT
<213> ORGANISM: Artificial Sequence
<220> FEATURE:
<223> OTHER INFORMATION: Clone 9 CDRH1

<400> SEQUENCE: 77

Ser Tyr Gly Met His
1               5

<210> SEQ ID NO 78
<211> LENGTH: 17
<212> TYPE: PRT
<213> ORGANISM: Artificial Sequence
<220> FEATURE:

<223> OTHER INFORMATION: Clone 9 CDRH2

<400> SEQUENCE: 78

Gly Ile Ser Trp Asp Ser Ala Ile Ile Asp Tyr Ala Gly Ser Val Lys
1               5                   10                  15

Gly

<210> SEQ ID NO 79
<211> LENGTH: 10
<212> TYPE: PRT
<213> ORGANISM: Artificial Sequence
<220> FEATURE:
<223> OTHER INFORMATION: Clone 9 CDRH3

<400> SEQUENCE: 79

Asp Glu Ala Ala Ala Gly Ala Phe Asp Ile
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Clone 9 CDRL1

<400> SEQUENCE: 80

Thr Gly Ser Ser Ser Asn Ile Gly Ala Gly Tyr Asp Val His
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Clone 9 CDRL2

<400> SEQUENCE: 81

Gly Asn Thr Asp Arg Pro Ser
1               5

<210> SEQ ID NO 82
<211> LENGTH: 12
<212> TYPE: PRT
<213> ORGANISM: Artificial Sequence
<220> FEATURE:
<223> OTHER INFORMATION: Clone 9 CDRL3

<400> SEQUENCE: 82

Ala Ala Trp Asp Asp Ser Leu Ser Gly Pro Val Val
1               5                   10

<210> SEQ ID NO 83
<211> LENGTH: 5
<212> TYPE: PRT
<213> ORGANISM: Artificial Sequence
<220> FEATURE:
<223> OTHER INFORMATION: Clone 10 CDRH1

<400> SEQUENCE: 83

Ser Tyr Gly Met His
1               5

<210> SEQ ID NO 84
<211> LENGTH: 17
<212> TYPE: PRT
<213> ORGANISM: Artificial Sequence

```
<220> FEATURE:
<223> OTHER INFORMATION: Clone 10 CDRH2

<400> SEQUENCE: 84

Val Ile Ser Tyr Asp Gly Ser Asn Lys Tyr Tyr Ala Asp Ser Val Lys
1               5                   10                  15
Gly

<210> SEQ ID NO 85
<211> LENGTH: 8
<212> TYPE: PRT
<213> ORGANISM: Artificial Sequence
<220> FEATURE:
<223> OTHER INFORMATION: Clone 10 CDRH3

<400> SEQUENCE: 85

Glu Leu Tyr Asp Ala Phe Asp Ile
1               5

<210> SEQ ID NO 86
<211> LENGTH: 14
<212> TYPE: PRT
<213> ORGANISM: Artificial Sequence
<220> FEATURE:
<223> OTHER INFORMATION: Clone 10 CDRL1

<400> SEQUENCE: 86

Thr Gly Ser Ser Ser Asn Ile Gly Ala Gly Tyr Asp Val His
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Clone 10 CDRL2

<400> SEQUENCE: 87

Ala Asp Asp His Arg Pro Ser
1               5

<210> SEQ ID NO 88
<211> LENGTH: 11
<212> TYPE: PRT
<213> ORGANISM: Artificial Sequence
<220> FEATURE:
<223> OTHER INFORMATION: Clone 10 CDRL3

<400> SEQUENCE: 88

Ala Ser Trp Asp Asp Ser Gln Arg Ala Val Ile
1               5                   10

<210> SEQ ID NO 89
<211> LENGTH: 5
<212> TYPE: PRT
<213> ORGANISM: Artificial Sequence
<220> FEATURE:
<223> OTHER INFORMATION: Clone 11 CDRH1

<400> SEQUENCE: 89

Ser Tyr Gly Met His
1               5

<210> SEQ ID NO 90
<211> LENGTH: 17
<212> TYPE: PRT
```

```
<213> ORGANISM: Artificial Sequence
<220> FEATURE:
<223> OTHER INFORMATION: Clone 11 CDRH2

<400> SEQUENCE: 90

Val Ile Ser Tyr Asp Gly Ser Asn Lys Tyr Tyr Ala Asp Ser Val Lys
1               5                   10                  15
Gly

<210> SEQ ID NO 91
<211> LENGTH: 9
<212> TYPE: PRT
<213> ORGANISM: Artificial Sequence
<220> FEATURE:
<223> OTHER INFORMATION: Clone 11 CDRH3

<400> SEQUENCE: 91

Glu Phe Gly Tyr Ile Ile Leu Asp Tyr
1               5

<210> SEQ ID NO 92
<211> LENGTH: 13
<212> TYPE: PRT
<213> ORGANISM: Artificial Sequence
<220> FEATURE:
<223> OTHER INFORMATION: Clone 11 CDRL1

<400> SEQUENCE: 92

Ser Gly Ser Ser Ser Asn Ile Gly Ser Asn Thr Val Asn
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Clone 11 CDRL2

<400> SEQUENCE: 93

Arg Asp Tyr Glu Arg Pro Ser
1               5

<210> SEQ ID NO 94
<211> LENGTH: 11
<212> TYPE: PRT
<213> ORGANISM: Artificial Sequence
<220> FEATURE:
<223> OTHER INFORMATION: Clone 11 CDRL3

<400> SEQUENCE: 94

Met Ala Trp Asp Asp Ser Leu Ser Gly Val Val
1               5                   10

<210> SEQ ID NO 95
<211> LENGTH: 5
<212> TYPE: PRT
<213> ORGANISM: Artificial Sequence
<220> FEATURE:
<223> OTHER INFORMATION: Clone 12 CDRH1

<400> SEQUENCE: 95

Asn His Gly Met His
1               5

<210> SEQ ID NO 96
<211> LENGTH: 17
```

```
<212> TYPE: PRT
<213> ORGANISM: Artificial Sequence
<220> FEATURE:
<223> OTHER INFORMATION: Clone 12 CDRH2

<400> SEQUENCE: 96

Val Ile Ser Tyr Asp Gly Thr Asn Lys Tyr Tyr Ala Asp Ser Val Arg
1               5                   10                  15
Gly

<210> SEQ ID NO 97
<211> LENGTH: 8
<212> TYPE: PRT
<213> ORGANISM: Artificial Sequence
<220> FEATURE:
<223> OTHER INFORMATION: Clone 12 CDRH3

<400> SEQUENCE: 97

Glu Thr Trp Asp Ala Phe Asp Val
1               5

<210> SEQ ID NO 98
<211> LENGTH: 13
<212> TYPE: PRT
<213> ORGANISM: Artificial Sequence
<220> FEATURE:
<223> OTHER INFORMATION: Clone 12 CDRL1

<400> SEQUENCE: 98

Ser Gly Ser Ser Ser Asn Ile Gly Ser Asn Asn Ala Asn
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Clone 12 CDRL2

<400> SEQUENCE: 99

Asp Asn Asn Lys Arg Pro Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Clone 12 CDRL3

<400> SEQUENCE: 100

Gln Ala Trp Asp Ser Ser Thr Val Val
1               5

<210> SEQ ID NO 101
<211> LENGTH: 5
<212> TYPE: PRT
<213> ORGANISM: Artificial Sequence
<220> FEATURE:
<223> OTHER INFORMATION: Clone 13 CDRH1

<400> SEQUENCE: 101

Ser Tyr Gly Ile Ser
1               5

<210> SEQ ID NO 102
```

```
<211> LENGTH: 17
<212> TYPE: PRT
<213> ORGANISM: Artificial Sequence
<220> FEATURE:
<223> OTHER INFORMATION: Clone 13 CDRH2

<400> SEQUENCE: 102

Gly Ile Ser Gly Ser Gly Gly Asn Thr Tyr Tyr Ala Asp Ser Val Lys
1               5                   10                  15

Gly

<210> SEQ ID NO 103
<211> LENGTH: 12
<212> TYPE: PRT
<213> ORGANISM: Artificial Sequence
<220> FEATURE:
<223> OTHER INFORMATION: Clone 13 CDRH3

<400> SEQUENCE: 103

Ser Val Gly Ala Tyr Ala Asn Asp Ala Phe Asp Ile
1               5                   10

<210> SEQ ID NO 104
<211> LENGTH: 14
<212> TYPE: PRT
<213> ORGANISM: Artificial Sequence
<220> FEATURE:
<223> OTHER INFORMATION: Clone 13 CDRL1

<400> SEQUENCE: 104

Thr Gly Ser Ser Ser Asn Ile Gly Ala Gly Tyr Asp Val His
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Clone 13 CDRL2

<400> SEQUENCE: 105

Gly Asp Thr Asn Arg Pro Ser
1               5

<210> SEQ ID NO 106
<211> LENGTH: 11
<212> TYPE: PRT
<213> ORGANISM: Artificial Sequence
<220> FEATURE:
<223> OTHER INFORMATION: Clone 13 CDRL3

<400> SEQUENCE: 106

Ala Ala Trp Asp Asp Ser Leu Asn Gly Pro Val
1               5                   10
```

COMBINED USE OF FCγRIIB (CD32B) AND CD20 SPECIFIC ANTIBODIES

RELATED APPLICATION DATA

This application is a continuation of U.S. patent application Ser. No. 13/817,744, filed May 31, 2013 (issued as U.S. Pat. No. 10,525,129) which is the U.S. National Stage of International Application No. PCT/GB2011/051572, filed Aug. 19, 2011, which claims priority to Great Britain Patent Application No. 1013989.7, filed Aug. 20, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 48,038 byte ASCII (text) file named "Seq_List" created on Nov. 14, 2019.

TECHNICAL FIELD

The invention relates to agents that prevent binding between the Fc domain of an antibody and FcγRIIb on a cell surface. The invention also relates to compositions which include those agents for use in treating patients having target cells such as cancer cells that are treated with antibody-based compositions.

Further, the invention relates to methods for predicting the response of target cells to antibody-based treatments, particularly where the antibody ligand is susceptible to FcγRIIb-mediated internalization and, in particular to the use of FcγRIIb expression levels and/or therapeutic antibody-mediated internalization via FcγRIIb as a prognostic marker for the response of the target cells to such treatment.

BACKGROUND

A mechanism by which monoclonal antibodies (mAb) can exert therapeutic effects is by stimulating the removal of cancer and other unwanted cells through recruiting natural effector systems such as cytotoxic cells (e.g. macrophages) and enzymes (e.g. complement) which then target the cell to which the mAb is bound.

For example, Type I anti-CD20 mAb (such as the current market leader rituximab) work by binding to CD20 molecules on the surface of B cells, via the mAb's antigen binding domains, and deleting these target B cells. They do this through recruiting and activating effector cells which interact with the Fc domains of the mAb through FcgammaReceptors (FcγR) expressed on the surface of these effector cells.

The anti-CD20 monoclonal antibody (mAb) rituximab has improved the overall survival (OS) of patients with follicular (FL) and diffuse large B-cell lymphoma (DLBCL) (1-4). In mantle cell lymphoma (MCL), only modest responses are seen (5) whilst in chronic lymphocytic leukemia (CLL), initial single-agent rituximab trials produced less striking responses than in other non-Hodgkin lymphoma (NHL) counterparts (reviewed in (6). A proportion of lymphomas show primary resistance to rituximab or eventually become resistant to rituximab-containing combination therapy (7). The molecular basis behind this treatment resistance and the observed sensitivities of different NHL-subtypes to rituximab treatment is currently unknown, but may include levels of CD20 expression (8-10), high expression of complement defense molecules (CD55 and CD59) (11, 12), development of apoptosis resistance (13) and sub-optimal Fc-gamma-receptor (FcγR) interactions as a result of expression of low affinity alleles (14).

It is highly desirable to increase the effectiveness of such antibodies where treatment is not optimal or resistance is apparent.

SUMMARY

It is generally accepted that Fc:FcγR interactions are crucial to the efficacy of anti-CD20 mAb (15-18). In keeping with this, lymphoma patients bearing the higher affinity 158V allele in FcγRIIIa respond better to rituximab compared with those with the low affinity 158F allotype (14), leading many investigators to focus on augmenting the interaction of mAb with FcγRIIIa, for example via defucosylation (19). In contrast, less attention has been given to the potential effects of the inhibitory FcγRIIb which acts as a negative regulator of stimulatory activity received by ITAM-bearing receptors such as the B-cell receptor for antigen (BCR) and activatory FcγR. In B cells, this interaction serves to limit B-cell proliferation following binding of immune complexes, whereas in macrophages engagement of FcγRIIb results in inhibition of cytotoxic activity (15).

Among B-cell malignancies, FcγRIIb is expressed on CLL/SLL, MCL and FL, the latter particularly during transformation. In DLBCL, FγRIIb expression is weaker, thus explaining why no correlation was demonstrable between its expression and response to rituximab-CHOP (R-CHOP) chemotherapy (20, 21). As with activatory FcγRs, polymorphisms influencing the activity of FcγRIIb have also been found (22, 23) with the 232I allele inhibiting BCR-mediated calcium flux more efficiently than the 232T allele. However, Weng and Levy (24) failed to establish a correlation between these polymorphisms and response to rituximab therapy in FL patients.

An increasing number of anti-CD20 mAb are becoming available for clinical investigation. These various anti-CD20 mAb may be classified as type I (e.g. rituximab, ofatumumab) or type II (e.g. tositumomab (B1), GA101, 11B8) according to their ability to redistribute CD20 in the plasma membrane and their activity in various effector assays (25-27).

We and others have shown that type II mAb are more potent at deleting B-cell targets in a number of model systems (18, 19). For example, in a human CD20 transgenic (Tg) model of normal B-cell depletion, in which the greater capacity of type II mAb to elicit lysosomal cell death is not evident (25, 27), we demonstrated that this potency correlated with their resistance to internalization (28). This is in contrast to type I mAb like rituximab, which internalize rapidly from the cell surface together with CD20 in a process which is energy and temperature dependent and involves actin redistribution (28). The rate of modulation differed markedly on cells from different origins (primary tumor versus cell-lines; CLL versus FL) although the molecular basis of this remained unexplained.

WO 2008/002933 describes Fc gamma RIIB (CD32B) and CD20—specific antibodies and methods of treating B cell-related diseases or disorders using a combination of both antibodies. However, there is no teaching or suggestion to recognize and/or treat a subset of patients, namely those whose target cells express elevated levels of FcγRIIb, or to which type of antibody are suitable for combination treatment with FcγRIIb antibodies.

Unexpectedly, we now show that modulation correlates strongly with FcγRIIb surface expression, regardless of cell subtype, with over-expression being able to convert Ramos cells from slow to rapid modulators. Internalization of FcγRIIb occurred alongside CD20 and was preceded by its activation. Altogether these data provide a clear molecular rationale for the previously observed heterogeneity of modulation rates both within and between different NHL subtypes.

Hence, we now show that, surprisingly, a key factor determining the effectiveness of antibodies to antigens such as CD20 is interaction with the inhibitory FcγRIIb (also known as and including, CD32, CD32B, CD32B1, CD32B2, FcRII, FcγRII or FcRIIB) on the surface of the same cell. This interaction leads to internalisation of the antibodies by the target cell, thus removing their ability to interact with effector cell Fc receptors. We further demonstrate that agents such as anti-CD32 mAb are able to block this internalisation. We also demonstrate that such agents can be used in combination with antibodies (such as rituximab) to target cell surface antigens and improve their activity in vivo to delete normal B cells or tumour cells.

According to the invention there is provided a composition comprising:

(i) an antibody molecule that specifically binds a cell surface antigen of a target cell, which antibody has a Fc domain capable of binding FcγRIIb; in combination with (ii) an agent that prevents or reduces FcγRIIb binding to the Fc domain of the antibody molecule; and characterized in that the composition is for use in the treatment of a patient with target cells having an elevated level of FcγRIIb expression.

According to another aspect, the invention provides use of an agent that prevents or reduces binding between an Fc domain of an antibody molecule and FcγRIIb on a target cell; wherein the antibody molecule specifically binds a target cell surface antigen; and characterized in that the use is in the manufacture of a medicament for use in the treatment of a patient with target cells having an elevated level of expression of FcγRIIb.

According to another aspect, the invention provides a method of treating a patient having target cells that express FcγRIIb, the method comprising administering (i) an antibody molecule that specifically binds a surface antigen of the target cell, which antibody molecule has an Fc domain capable of binding FcγRIIb; in combination with (ii) an agent that prevents or reduces binding between the Fc domain of the antibody molecule and FcγRIIb; characterized in that the patient is selected on the basis that their target cells express an elevated level of FcγRIIb.

In certain embodiments of the composition, uses or methods of the invention, the agent prevents or reduces FcγRIIb present on the target cell from binding to the Fc domain of the antibody molecule.

According to another aspect, the invention provides use of FcγRIIb expression on target cells as a prognostic marker for the response of the target cells to treatment with an antibody molecule that binds specifically to a surface antigen of the target cells, the antibody molecule having an Fc domain capable of binding FcγRIIb; whereby elevated levels of FcγRIIb are indicative of a reduction in or the absence of a response to treatment with the antibody molecules.

In one embodiment, the use of FcγRIIb expression on target cells as a prognostic marker does not require the use of FcγRIIc expression on target cells as a prognostic marker.

According to another aspect, the invention provides a method for predicting the response of target cells of a patient to treatment with an antibody molecule that specifically binds a target cell surface antigen and has an Fc domain capable of binding FcγRIIb; characterized in that the method comprises determining the level of expression of FcγRIIb on the target cells, whereby elevated levels of FcγRIIb is predictive of a reduction in, or the absence of, a response to treatment with the antibody molecule.

In one embodiment, the method for predicting the response of target cells of a patient comprises determining the level of expression of FcγRIIb on the target cells and does not additionally comprise determining the level of expression of FcγRIIc on the target cells.

DETAILED DESCRIPTION

It has been demonstrated that not all antibodies, despite their common Fc-binding antibody constant domain and known Fc gamma receptor binding ability, are internalised in a FcγRIIb-dependent manner, making identification of suitable antibodies critical for therapeutic success with combination therapies comprising FcγRIIb-function modulating reagents and, conversely, for avoiding treatment that will not benefit patients.

In certain embodiments of the composition, use or methods of the invention, the antibody molecule that specifically binds a cell surface antigen of a target cell, which antibody has a Fc domain capable of binding FcγRIIb is also capable of internalizing into the cell in an FcγRIIb-dependent manner.

In certain embodiments of the composition, use or methods of the invention, the agent that prevents or reduces FcγRIIb binding to the Fc domain of the antibody molecule additionally prevents or reduces subsequent internalization of the antibody molecule into the cell.

In certain embodiments of the composition, use or methods of the invention the target cell is a cancer cell. Conveniently the target cell is a B cell.

Advantageously, in accordance with the invention elevated FcγRIIb expression on the target cells is determined relative to a control or reference. Preferably, the control is the normal level of FcγRIIb expression in cells of the same type as the target cells.

'Elevated levels of FcγRIIb expression' is defined below under 'Definitions'. FcγRIIb expression level can be measured as a ratio of the Geometric Mean Fluorescent Intensity (Geo MFI) of FcγRIIb to isotype control. Alternatively, FcγRIIb expression levels can be measured by immunohistochemistry of tumor biopsies. A person skilled in the art would understand that there are multiple techniques and methodologies for determining FcγRIIb expression levels.

The current invention also teaches how to identify antibodies that are suitable for combination treatment with FcγRIIb antibodies, namely those antibodies that are internalized from the target cell surface in an FcγRIIb dependent manner. The current invention further provides means to identify patient subsets that are suitable for combination treatment with FcγRIIb antibodies.

In another aspect the invention provides an assay for identifying agents that reduce or prevent binding between the Fc domain of an antibody to a target cell surface antigen and FcγRIIb on the target cell, comprising determining the extent of binding between the Fc domain and FcγRIIb in the presence and absence of a test agent. Useful agents are identified if the test agent reduces or prevents Fc domain binding to FcγRIIb. Such assays are also useful for identifying which agents (for example antibody molecules) are suitable for combination therapy with anti-FcγRIIb antibodies.

In another preferred embodiment the assay for identifying agents useful in the practice of the uses and methods of the invention involves screening for agents that block stimulation/signaling of FcγRIIb, as indicated by phosphorylation of tyrosine-293 in the intracellular ITIM motif as detected by Western blotting. For example, Raji cells are cultured with an antibody to a cell surface antigen, e.g. the anti-CD20 mAb rituximab, in the presence or absence of the anti-FcγRIIb test agent before immunoblotting for phosphorylated FcγRIIb. The amount of phosphorylated FcγRIIb becomes elevated in cells stimulated by rituximab, and should be inhibited by the addition of the test agents similar to that shown in FIG. 4A using AT10 as the blocking agent. In addition, these agents should preferably also block internalization of rituximab according to the quenching assay indicated in FIG. 1A. FIG. 2B shows a typical example of blocking by an anti-FcγRIIb blocking entity, in this case AT10. Such assays are also useful for identifying which agents (for example antibody molecules) are suitable for combination therapy with anti-FcγRIIb antibodies.

In a preferred embodiment the assay used to identify agents suitable for combination therapy with FcγRIIb antibodies measures the percentage of agent (for example antibody molecule) internalization into FcγRIIb-expressing cells. This assay is characterized in that the method comprises determining the percentage of agent (for example antibody molecules) retained at the cell surface following incubation with agent (for example antibody molecule) target-expressing and FcγRIIb-expressing cells, whereby decreasing percentages of agent (for example antibody molecules) accessible at the cell surface (equivalent of increasing antibody molecule internalization) is predictive of, a response to treatment with the antibody molecule.

Neubig et al (2003) *Pharmacol. Rev.* 55, 597-606, incorporated herein by reference, describes various classes of ligands which may be screened to identify agents that prevent or reduce FcγRIIb binding to an Fc domain of an antibody molecule according to the invention.

The above-mentioned ligands may be small organic or inorganic moieties, but they are preferably peptides or polypeptides. Typically, when the ligand is a small organic or organic moiety, it has a $M_r$ of from 50 to 2000, such as from 100 to 1000, for example from 100 to 500.

Typically, the ligand binds to FcγRIIb with a $K_d$ of from mM to pM, such as in the range of from μM (micromolar) to nM. Generally, the ligands with the lowest Kd are preferred.

The ligand may be a peptidomimetic, a nucleic acid, a peptide nucleic acid (PNA) or an aptamer. It may also be a lipid, or a carbohydrate.

The ligand may be a polypeptide which binds to FcγRIIb. Such polypeptides (by which we include oligopeptides) are typically from $M_r$ 500 to $M_r$ 50,000, but may be larger.

The polypeptide may also be a binding protein based on a modular framework, such as ankyrin repeat proteins, armadillo repeat proteins, leucine rich proteins, tetratriopeptide repeat proteins or Designed Ankyrin Repeat Proteins (DARPins) or proteins based on lipocalin or fibronectin domains or Affilin scaffolds.

Conveniently, the test agent is a library of test compounds and preferably the library is any of a peptide library, a protein library, an antibody library, a recombinant combinatorial antibody library or a scFV or Fab phage display library.

Preferably, in a composition, use, or method according to the invention the agent (ii) is one or more antibody molecules that specifically bind FcγRIIb. Conveniently, the one or more antibody molecules do not include a domain capable of recruiting an effector cell of recruiting an effector cell.

Advantageously, the one or more antibody molecules are one or more monoclonal antibody molecules.

Preferably the agent prevents or reduces FcγRIIb signaling. Even more preferably, the agent prevents or reduces internalization of the antibody molecule by the target cell.

In the following embodiments, the SEQ ID NOs refer to the sequences indicated in clones 1-13 below.

As the skilled person will be aware, three complementarity determining regions (CDRs) are present on the variable domains of both the heavy and light chains of immunoglobulins. The assignment of amino acids to each CDR described herein is in accordance with the definitions according to Kabat E A et al. 1991, In "Sequences of Proteins of Immulogical Interest" Fifth Edition, NIH Publication No. 91-3242, pp xv-xvii).

As the skilled person would be aware, other methods also exist for assigning amino acids to each CDR. For example, the International ImMunoGeneTics information system (IMGT®) (http://www.imgt.org/ and Lefranc and Lefranc "The Immunoglobulin FactsBook" published by Academic Press, 2001).

In one embodiment the agent comprises a variable heavy chain (VH) comprising the following CDRs:
(i) SEQ ID NO: 29 and SEQ ID NO: 30 and SEQ ID NO: 31; or
(ii) SEQ ID NO: 35 and SEQ ID NO: 36 and SEQ ID NO: 37; or
(iii) SEQ ID NO: 41 and SEQ ID NO: 42 and SEQ ID NO: 43; or
(iv) SEQ ID NO: 47 and SEQ ID NO: 48 and SEQ ID NO: 49; or
(v) SEQ ID NO: 53 and SEQ ID NO: 54 and SEQ ID NO: 55; or
(vi) SEQ ID NO: 59 and SEQ ID NO: 60 and SEQ ID NO: 61; or
(vii) SEQ ID NO: 65 and SEQ ID NO: 66 and SEQ ID NO: 67; or
(viii) SEQ ID NO: 71 and SEQ ID NO: 72 and SEQ ID NO: 73; or
(ix) SEQ ID NO: 77 and SEQ ID NO: 78 and SEQ ID NO: 79; or
(x) SEQ ID NO: 83 and SEQ ID NO: 84 and SEQ ID NO: 85; or
(xi) SEQ ID NO: 89 and SEQ ID NO: 90 and SEQ ID NO: 91; or
(xii) SEQ ID NO: 95 and SEQ ID NO: 96 and SEQ ID NO: 97; or
(xiii) SEQ ID NO: 101 and SEQ ID NO: 102 and SEQ ID NO: 103.

Preferably, the agent comprises a variable light chain (VL) comprising the following CDRs:
(i) SEQ ID NO: 32 and SEQ ID NO: 33 and SEQ ID NO: 34; or
(ii) SEQ ID NO: 38 and SEQ ID NO: 39 and SEQ ID NO: 40; or
(iii) SEQ ID NO: 44 and SEQ ID NO: 45 and SEQ ID NO: 46; or
(iv) SEQ ID NO: 50 and SEQ ID NO: 51 and SEQ ID NO: 52; or
(v) SEQ ID NO: 56 and SEQ ID NO: 57 and SEQ ID NO: 58; or (vi) SEQ ID NO: 62 and SEQ ID NO: 63 and SEQ ID NO: 64; or
(vii) SEQ ID NO: 68 and SEQ ID NO: 69 and SEQ ID NO: 70; or
(viii) SEQ ID NO: 74 and SEQ ID NO: 75 and SEQ ID NO: 76; or
(ix) SEQ ID NO: 80 and SEQ ID NO: 81 and SEQ ID NO: 82; or
(x) SEQ ID NO: 86 and SEQ ID NO: 87 and SEQ ID NO: 88; or
(xi) SEQ ID NO: 92 and SEQ ID NO: 93 and SEQ ID NO: 94; or
(xii) SEQ ID NO: 98 and SEQ ID NO: 99 and SEQ ID NO: 100; or
(xiii) SEQ ID NO: 104 and SEQ ID NO: 105 and SEQ ID NO: 106.

Optionally, the agent comprises a variable heavy chain (VH) amino acid sequence selected from the group consisting of: SEQ ID NO: 3; SEQ ID NO: 4; SEQ ID NO: 5, SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; and SEQ ID NO: 15.

Optionally, the agent comprises a variable light chain (VL) amino acid sequence selected from the group consisting of: SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO:23; SEQ ID NO: 24; SEQ ID NO: 25; SEQ ID NO: 26; SEQ ID NO: 27; and SEQ ID NO: 28.

Preferably, the agent comprises the following CDR amino acid sequences:
(i) SEQ ID NO: 29 and SEQ ID NO: 30 and SEQ ID NO: 31 and SEQ ID NO: 32 and SEQ ID NO: 33 and SEQ ID NO: 34; or
(ii) SEQ ID NO: 35 and SEQ ID NO: 36 and SEQ ID NO: 37 and SEQ ID NO: 38 and SEQ ID NO: 39 and SEQ ID NO: 40; or
(iii) SEQ ID NO: 41 and SEQ ID NO: 42 and SEQ ID NO: 43 and SEQ ID NO: 44 and SEQ ID NO: 45 and SEQ ID NO: 46; or
(iv) SEQ ID NO: 47 and SEQ ID NO: 48 and SEQ ID NO: 49 and SEQ ID NO: 50 and SEQ ID NO: 51 and SEQ ID NO: 52; or
(v) SEQ ID NO: 53 and SEQ ID NO: 54 and SEQ ID NO: 55 and SEQ ID NO: 56 and SEQ ID NO: 57 and SEQ ID NO: 58; or
(vi) SEQ ID NO: 59 and SEQ ID NO: 60 and SEQ ID NO: 61 and SEQ ID NO: 62 and SEQ ID NO: 63 and SEQ ID NO: 64; or
(vii) SEQ ID NO: 65 and SEQ ID NO: 66 and SEQ ID NO: 67 and SEQ ID NO: 68 and SEQ ID NO: 69 and SEQ ID NO: 70; or
(viii) SEQ ID NO: 71 and SEQ ID NO: 72 and SEQ ID NO: 73 and SEQ ID NO: 74 and SEQ ID NO: 75 and SEQ ID NO: 76; or
(ix) SEQ ID NO: 77 and SEQ ID NO: 78 and SEQ ID NO: 79 and SEQ ID NO: 80 and SEQ ID NO: 81 and SEQ ID NO: 82; or
(x) SEQ ID NO: 83 and SEQ ID NO: 84 and SEQ ID NO: 85 and SEQ ID NO: 86 and SEQ ID NO: 87 and SEQ ID NO: 88; or
(xi) SEQ ID NO: 89 and SEQ ID NO: 90 and SEQ ID NO: 91 and SEQ ID NO: 92 and SEQ ID NO: 93 and SEQ ID NO: 94; or
(xii) SEQ ID NO: 95 and SEQ ID NO: 96 and SEQ ID NO: 97 and SEQ ID NO: 98 and SEQ ID NO: 99 and SEQ ID NO: 100; or
(xiii) SEQ ID NO: 101 and SEQ ID NO: 102 and SEQ ID NO: 103 and SEQ ID NO: 104 and SEQ ID NO: 105 and SEQ ID NO: 106.

Even more preferably, the agent comprises the following amino acid sequences:
(i) SEQ ID NO: 3 and SEQ ID NO: 16; or
(ii) SEQ IS NO: 4 and SEQ ID NO: 17; or
(iii) SEQ IS NO: 5 and SEQ ID NO: 18; or
(iv) SEQ ID NO: 6 and SEQ ID NO: 19; or
(v) SEQ ID NO: 7 and SEQ ID NO: 20; or
(vi) SEQ ID NO: 8 and SEQ ID NO: 21; or
(vii) SEQ ID NO: 9 and SEQ ID NO: 22; or
(viii) SEQ ID NO: 10 and SEQ ID NO: 23; or
(ix) SEQ ID NO: 11 and SEQ ID NO: 24; or
(x) SEQ ID NO: 12 and SEQ ID NO: 25; or
(xi) SEQ ID NO: 13 and SEQ ID NO: 26; or
(xii) SEQ ID NO: 14 and SEQ ID NO: 27; or
(xiii) SEQ ID NO: 15 and SEQ ID NO: 28.

The agents of the invention may also comprise the constant regions (CH) and (CL) of SEQ ID NO 1 and SEQ ID NO 2.

In a further embodiment, the agent is capable of competing with the agents of the invention described herein, for example agents comprising the amino acid sequences set out in the embodiments above (for example SEQ ID NOs: 1-106), for preventing or reducing FcγRIIb binding to the Fc domain of the antibody molecule.

By "capable of competing" for preventing or reducing FcγRIIb binding to the Fc domain of the antibody molecule with an agent (such as an antigen molecule) as defined herein we mean that the tested agent is capable of inhibiting or otherwise interfering, at least in part, with the binding of an agent as defined herein to FcγRIIb and preventing or reducing FcγRIIb binding to the Fc domain of the antibody molecule.

For example, the agent may be capable of inhibiting the binding of an agent described herein by at least 10%, for example at least 20%, 30%, 40%, 50%, 60%, 70%, 80%, 90%, 95% or even by 100% and/or inhibiting the ability of the agent to prevent or reduce FcγRIIb binding to the Fc domain of the antibody molecule by at least 10%, for example at least 20%, 30%, 40%, 50%, 60%, 70%, 80%, 90%, 95% or even by 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in *Antibodies: A Laboratory Manual*, Harlow & Lane, which is incorporated herein by reference (for example, see pages 567 to 569, 574 to 576, 583 and 590 to 612, 1988, CSHL, NY, ISBN 0-87969-314-2).

The agents of the invention may comprise the following constant regions (CH and CL):

```
IgG1-CH                                                              [SEQ ID NO: 1]

ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGV
```

```
EVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKSLSLSP

GK

λ-CL
                                                    [SEQ ID NO: 2]
QPKAAPSVTLFPPSSEELQANKATLVCLISDFYPGAVTVAWKADSSPVKAGVETT

TPSKQSNNKYAASSYLSLTPEQWKSHRSYSCQVTHEGSTVEKTVAPTECS

The agents of the invention may comprise one or more sequences of clones 1-14:
Clone 1
VH
                                                    [SEQ ID NO: 3]
EVQLLESGGGLVQPGGSLRLSCAASGFTFSNYGMHWVRQAPGKGLEWVAVISYDGSNKYYADSVKGRF
         FrH1         CDRH1       FrH2       CDRH2

TISRDNSKNTLYLQMNSLRAEDTAVYYCAREWRDAFDIWGQGTLVTSS
       FrH            CDRH3       FrH4

-VL
                                                    [SEQ ID NO: 16]
QSVLTQPPSASGTPGQRVTISCTGSSSNIGAGYDVHWYQQLPGTAPKLLIYSDNQRPSGVPDRFSGSKSG
        FrL1       CDRL1         FrL2        CDRL2      FrL3

TSASLAISGLRSEDEADYYCAAWDDSLSGSWVFGGGTKLTVLG
                    CDRL3       FrL4

CDR Regions
                                                    [SEQ ID NO: 29]
CDRH1: NYGMH

[SEQ ID NO: 30]
CDRH2: VISYDGSNKYYADSVKG

[SEQ ID NO: 31]
CDRH3: EWRDAFDI

[SEQ ID NO: 32]
CDRL1: TGSSSNIGAGYDVH

[SEQ ID NO: 33]
CDRL2: SDNQRPS

[SEQ ID NO: 34]
CDRL3: AAWDDSLSGSWV

Clone 2
-VH
                                                    [SEQ ID NO: 4]
EVQLLESGGGLVQPGGSLRLSCAASGFTFSTYGMHWVRQAPGKGLEWVAVIAYDGSKKDYADSVKGRFTISR

DNSKNTLYLQMNSLRAEDTAVYYCAREYRDAFDIWGQGTLVTVSS

-VL
                                                    [SEQ ID NO: 17]
QSVLTQPPSASGTPGQRVTISCTGSSSNIGAGYDVHWYQQLPGTAPKLLIYGNSNRPSGVPDRFSGSKSGTTA

SLAISGLRSEDEADYYCAAWDDSVSGWMFGGGTKLTVLG

CDR Regions
                                                    [SEQ ID NO: 35]
CDRH1: TYGMH

[SEQ ID NO: 36]
CDRH2: VIAYDGSKKDYADSVKG

[SEQ ID NO: 37]
CDRH3: EYRDAFDI
```

```
                                                                    [SEQ ID NO: 38]
CDRL1: TGSSSNIGAGYDVH

[SEQ ID NO: 39]
CDRL2: GNSNRPS

[SEQ ID NO: 40]
CDRL3: AAWDDSVSGWM

Clone 3
-VH
                                                                    [SEQ ID NO: 5]
EVQLLESGGGLVQPGGSLRLSCAASGFTFNNYGMHWVRQAPGKGLEWVAVISYDGSNRYYADSVKGRFTM
SRDNSKNTLYLQMNSLRAEDTAVYYCARDRWNGMDVWGQGTLVTVSS -VL
                                                                    [SEQ ID NO: 18]
QSVLTQPPSASGTPGQRVTISCSGSSSNIGAGYDVHWYQQLPGTAPKLLIYANNQRPSGVPDRFSGSKSGTSA
SLAISGLRSEDEADYYCAAWDDSLNGPWVFGGGTKLTVLG CDR Regions
                                                                    [SEQ ID NO: 41]
CDRH1: NYGMH

[SEQ ID NO: 42]
CDRH2: VISYDGSNRYYADSVKG

[SEQ ID NO: 43]
CDRH3: DRWNGMDV

[SEQ ID NO: 44]
CDRL1: SGSSSNIGAGYDVH

[SEQ ID NO: 45]
CDRL2: ANNQRPS

[SEQ ID NO: 46]
CDRL3: AAWDDSLNGPWV

Clone 4
-VH
                                                                    [SEQ ID NO: 6]
EVQLLESGGGLVQPGGSLRLSCAASGFTFSSYGMHWVRQAPGKGLEWVAVISYDGSDTAYADSVKGRFTISR
DNSKNTLYLQMNSLRAEDTAVYYCARDHSVIGAFDIWGQGTLVTVSS -VL
                                                                    [SEQ ID NO: 19]
QSVLTQPPSASGTPGQRVTISCSGSSSNIGSNTVNWYQQLPGTAPKLLIYDNNKRPSGVPDRFSGSKSGTSASL
AISGLRSEDEADYYCSSYAGSNNVVFGGGTKLTVLG CDR Regions
                                                                    [SEQ ID NO: 47]
CDRH1: SYGMH

[SEQ ID NO: 48]
CDRH2: VISYDGSDTAYADSVKG

[SEQ ID NO: 49]
CDRH3: DHSVIGAFDI

[SEQ ID NO: 50]
CDRL1: SGSSSNIGSNTVN

[SEQ ID NO: 51]
CDRL2: DNNKRPS

[SEQ ID NO: 52]
CDRL3: SSYAGSNNVV
```

-continued

Clone 5
-VH
[SEQ ID NO: 7]
EVQLLESGGGLVQPGGSLRLSCAASGFTFS NYGMH WVRQAPGKGLEWVA VISYDGSNKYYADSVKG RFTISR
DNSKNTLYLQMNSLRAEDTAVYYCAR DQLGEAFDI WGQGTLVTVSS -VL
[SEQ ID NO: 20]
QSVLTQPPSASGTPGQRVTISC TGSSSNIGAYDVH WYQQLPGTAPKLLIY DNNKRPS GVPDRFSGSKSGTSA
SLAISGLRSEDEADYYC ATWDDSLSGPV FGGGTKLTVLG CDR Regions
[SEQ ID NO: 53]
CDRH1: NYGMH

[SEQ ID NO: 54]
CDRH2: VISYDGSNKYYADSVKG

[SEQ ID NO: 55]
CDRH3: DQLGEAFDI

[SEQ ID NO: 56]
CDRL1: TGSSSNIGAYDVH

[SEQ ID NO: 57]
CDRL2: DNNKRPS

[SEQ ID NO: 58]
CDRL3: ATWDDSLSGPV

Clone 6
-VH
[SEQ ID NO: 8]
EVQLLESGGGLVQPGGSLRLSCAASGFTFD DYGMS WVRQAPGKGLEWVS AISGSGSSTYYADSVKG RFTISR
DNSKNTLYLQMNSLRAEDTAVYYCAG GDIDYFDY WGQGTLVTVSS -VL
[SEQ ID NO: 21]
QSVLTQPPSASGTPGQRVTISC TGSSSNFGAGYDVH WYQQLPGTAPKLLIY ENNKRPS GVPDRFSGSKSGTSA
SLAISGLRSEDEADYYC AAWDDSLNGPV GGGTKLTVLG CDR Regions
[SEQ ID NO: 59]
CDRH1: DYGMS

[SEQ ID NO: 60]
CDRH2: AISGSGSSTYYADSVKG

[SEQ ID NO: 61]
CDRH3: GDIDYFDY

[SEQ ID NO: 62]
CDRL1: TGSSSNFGAGYDVH

[SEQ ID NO: 63]
CDRL2: ENNKRPS

[SEQ ID NO: 64]
CDRL3: AAWDDSLNGPV

Clone 7
-VH
[SEQ ID NO: 9]
EVQLLESGGGLVQPGGSLRLSCAASGFTFS SYGMH WVRQAPGKGLEWVA VISYDGSNKYYADSVKG RFTISR
DNSKNTLYLQMNSLRAEDTAVYYCAR ERRDAFDI WGQGTLVTVSS -VL
[SEQ ID NO: 22]
QSVLTQPPSASGTPGQRVTISC TGSSSNIGAYDVH WYQQLPGTAPKLLIY SDNQRPS GVPDRFSGSKSGTSA
SLAISGLRSEDEADYYC ATWDSDTPV FGGGTKLTVLG -continued CDR Regions

CDRH1: SYGMH [SEQ ID NO: 65]

CDRH2: VISYDGSNKYYADSVKG [SEQ ID NO: 66]

CDRH3: ERRDAFDI [SEQ ID NO: 67]

CDRL1: TGSSSNIGAGYDVH [SEQ ID NO: 68]

CDRL2: SDNQRPS [SEQ ID NO: 69]

CDRL3: ATWDSDTPV [SEQ ID NO: 70]

Clone 8
-VH
[SEQ ID NO: 10]
EVQLLESGGGLVQPGGSLRLSCAASGFTFSSYGMHWVRQAPGKGLEWVAVISYDGSNKYYADSVKGRFTISR
DNSKNTLYLQMNSLRAEDTAMYYCARDHSAAGYFDYWGQGTLVTVSS -VL
[SEQ ID NO: 23]
QSVLTQPPSASGTPGQRVTISCSGSSSNIGSNTVNWYQQLPGTAPKLLIYGNSIRPSGGPDRFSGSKSGTSASL
AISGLRSEDEADYYCASWDDSLSSPVFGGGTKLTVLG CDR Regions

CDRH1: SYGMH [SEQ ID NO: 71]

CDRH2: VISYDGSNKYYADSVKG [SEQ ID NO: 72]

CDRH3: DHSAAGYFDY [SEQ ID NO: 73]

CDRL1: SGSSSNIGSNTVN [SEQ ID NO: 74]

CDRL2: GNSIRPS [SEQ ID NO: 75]

CDRL3: ASWDDSLSSPV [SEQ ID NO: 76]

Clone 9
-VH
[SEQ ID NO: 11]
EVQLLESGGGLVQPGGSLRLSCAASGFTFGSYGMHWVRQAPGKGLEWVSGISWDSAIIDYAGSVKGRFTISR
DNSKNTLYLQMNSLRAEDTAVYYCAKDEAAAGAFDIWGQGTLVTVSS -VL
[SEQ ID NO: 24]
QSVLTQPPSASGTPGQRVTISCTGSSSNIGAGYDVHWYQQLPGTAPKLLIYGNTDRPSGVPDRFSGSKSGTSA
SLAISGLRSEDEADYYCAAWDDSLSGPVVFGGGTKLTVLG CDR Regions

CDRH1: SYGMH [SEQ ID NO: 77]

CDRH2: GISWDSAIIDYAGSVKG [SEQ ID NO: 78]

CDRH3: DEAAAGAFDI [SEQ ID NO: 79]

CDRL1: TGSSSNIGAGYDVH [SEQ ID NO: 80]

CDRL2: GNTDRPS [SEQ ID NO: 81]

CDRL3: AAWDDSLSGPVV [SEQ ID NO: 82]

-continued

Clone 13
-VH

[SEQ ID NO: 15]

EVQLLESGGGLVQPGGSLRLSCAASGFTLS SYGIS WVRQAPGKGLEWVS GISGSGGNTYYADSVKG RFTISRD
NSKNTLYLQMNSLRAEDTAVYYCAS SVGAYANDAFDI WGQGTLVTVSS

-VL

[SEQ ID NO: 28]

QSVLTQPPSASGTPGQRVTISC TGSSSNIGAGYDVH WYQQLPGTAPKLLIY GDTNRPS GVPDRFSGSKSGTSA
SLAISGLRSEDEADYYC AAWDDSLNGPV FGGGTKLTVLG

CDR Regions

[SEQ ID NO: 101]
CDRH1: SYGIS

[SEQ ID NO: 102]
CDRH2: GISGSGGNTYYADSVKG

[SEQ ID NO: 103]
CDRH3: SVGAYANDAFDI

[SEQ ID NO: 104]
CDRL1: TGSSSNIGAGYDVH

[SEQ ID NO: 105]
CDRL2: GDTNRPS

[SEQ ID NO: 106]
CDRL3: AAWDDSLNGPV

Clone 10
-VH

[SEQ ID NO: 12]

EVQLLESGGGLVQPGGSLRLSCAASGFTFS SYGMH WVRQAPGKGLEWMA VISYDGSNKYYADSVKG RFTIS
RDNSKNTLYLQMNSLRAEDTAVYYCAR ELYDAFDI WGQGTLVTVSS

-VL

[SEQ ID NO: 25]

QSVLTQPPSASGTPGQRVTISC TGSSSNIGAGYDVH WYQQLPGTAPKLLIY ADDHRPS GVPDRFSGSKSGTSA
SLAISGLRSEDEADYYC ASWDDSQRAVI FGGGTKLTVLG

CDR Regions

[SEQ ID NO: 83]
CDRH1: SYGMH

[SEQ ID NO: 84]
CDRH2: VISYDGSNKYYADSVKG

[SEQ ID NO: 85]
CDRH3: ELYDAFDI

[SEQ ID NO: 86]
CDRL1: TGSSSNIGAGYDVH

[SEQ ID NO: 87]
CDRL2: ADDHRPS

[SEQ ID NO: 88]
CDRL3: ASWDDSQRAVI

Clone 11
-VH

[SEQ ID NO: 13]

EVQLLESGGGLVQPGGSLRLSCAASGFTFS SYGMH WVRQAPGKGLEWVA VISYDGSNKYYADSVKG RFTISR
DNSQNTLYLQMNSLRAEDTAVYYCAR EFGYIILDY WGQGTLVTVSS

-VL

[SEQ ID NO: 26]

QSVLTQPPSASGTPGQRVTISC SGSSSNIGSNTVN WYQQLPGTAPKLLIY RDYERPS GVPDRFSGSKSGTSASL
AISGLRSEDEADYYC MAWDDSLSGVV FGGGTKLTVLG

```
CDR Regions
                                                                    [SEQ ID NO: 89]
CDRH1: SYGMH

[SEQ ID NO: 90]
CDRH2: VISYDGSNKYYADSVKG

[SEQ ID NO: 91]
CDRH3: EFGYIILDY

[SEQ ID NO: 92]
CDRL1: SGSSSNIGSNTVN

[SEQ ID NO: 93]
CDRL2: RDYERPS

[SEQ ID NO: 94]
CDRL3: MAWDDSLSGVV

Clone 12
-VH
                                                                    [SEQ ID NO: 14]
EVQLLESGGGLVQPGGSLRLSCAASGFTFSNHGMHWVRQAPGKGLEWVAVISYDGTNKYYADSVRGRFTIS
RDNSKNTLYLQMNSLRAEDTAVYYCARETWDAFDVWGQGTLVTVSS -VL
                                                                    [SEQ ID NO: 27]
QSVLTQPPSASGTPGQRVTISCSGSSSNIGSNNANWYQQLPGTAPKLLIYDNNKRPSGVPDRFSGSKSGTSAS
LAISGLRSEDEADYYCQAWDSSTVVFGGGTKLTVLG CDR Regions
                                                                    [SEQ ID NO: 95]
CDRH1: NHGMH

[SEQ ID NO: 96]
CDRH2: VISYDGTNKYYADSVRG

[SEQ ID NO: 97]
CDRH3: ETWDAFDV

[SEQ ID NO: 98]
CDRL1: SGSSSNIGSNNAN

[SEQ ID NO: 99]
CDRL2: DNNKRPS

[SEQ ID NO: 100]
CDRL3: QAWDSSTVV
```

Preferred target cell surface antigens may be selected from the following: CD20, Thy-1 (CD90, Cluster of Differentiation 90 (Biofactors. 2009 May-June; 35(3):258-65)); Ly-6 (Lymphocyte Antigen 6 (Mol Biol Rep. 2009 April; 36(4):697-703)); CD59 (Complement regulatory protein (Mol Immunol. 2007 January; 44(1-3):73-81)); Fas (FS7-associated cell surface antigen, CD95, APO-1 or TNFRSF6 (Adv Exp Med Biol. 2009; 647:64-93)); EGFR (Epidermal Growth Factor Receptor (FEBS J. 2010 January; 277(2): 301-8)); Her2 (Human epidermal growth factor receptor 2 (Clin Breast Cancer. 2008 October; 8(5):392-401)); CXCR4 (Chemokine Receptor 4 (Biochim Biophys Acta. 2007 April; 1768(4):952-63)); CD19 (Cluster of Differentiation 19 (Cell Immunol. 1989 February; 118(2):368-81)); CD40 (Cluster of Differentiation 40 (Basic Clin Pharmacol Toxicol. 2009 February; 104(2):87-92)); HLA Molecules (Human Leukocyte Antigen molecules (Korean J Lab Med. 2010 June; 30(3):203)); GM1 (ganglioside, monosialotetrahexosylganglioside (J Lipid Res. 2010 September; 51(9):2731-8)); CD22 (Cheson (2008) NEJM 359(6): 613-26); CD23 (Cheson, 2008); CD80 (Cheson, 2008); CD74 (Cheson, 2008); DRD (Cheson, 2008).

Preferably, in a composition, use, or method according to the invention the surface antigen is selected from CD19, CD20, or CD40 and more preferably, human forms thereof. CD20, especially human CD20, is most preferred.

Advantageously, the antibody molecule that specifically binds the cell surface antigen is a monoclonal antibody, preferably a monoclonal antibody that upon binding to the target cell is removed from the cell surface and internalized into the target cell in an FcγRIIb-dependent manner. Preferably the monoclonal antibody is an anti-CD19, anti-CD20 or anti-CD40 antibody. Most preferably, the monoclonal antibody is an anti-CD20 monoclonal antibody.

In a preferred embodiment, the antibody molecule specifically binding to a cell surface antigen is a Type I anti-CD20 antibody. In another preferred embodiment, the antibody molecule specifically binding to a cell surface antigen is not a Type II anti-CD20 antibody.

In one embodiment, the cell surface antigen is CD20 and the antibody molecule specifically binding to a cell surface antigen is a Type I antibody.

As mentioned above, there are two types of anti-CD20 monoclonal antibodies (mAb). Anti-CD20 mAb were first defined by the inventors as falling into different groupings in 2003 (43 and 25) and then subsequently defined as Type I and II mAbs in 2004 (26). Initially the basis for this was that anti-CD20 mAb fall into two distinct types of reagents based on their ability to eradicate lymphoma xenografts: type I (e.g. Rituximab and 1F5) utilize complement; and type II (e.g. B1), do not. Both types of mAb gave excellent prolongation of survival, but depleting complement activity, by administering CVF, considerably diminished the potency of Rituximab and 1F5, but had no effect on the activity of B1. These results clearly showed that different CD20 mAb operate different effector mechanisms in vivo. Furthermore, they are in complete accord with previous work showing that Rituximab and 1F5 are able to activate complement efficiently as a result of translocating CD20 to lipid rafts in the target cell membrane, something that B1-type mAb cannot do (43). There is an excellent correlation with the ability of mAb to engage complement and induce CD20 to move into lipid rafts (43, 26). Therefore Type I and II nature can be defined by their ability to move CD20 into lipid rafts. This can be determined as indicated below. There is also a correlation with Type II mAb being able to elicit more potent homotypic adhesion and direct cell death but these could not be used alone to define a Type I or II mAb (unlike the Tx-100 raft assays; see below).

Therefore, various anti-CD20 mAb may be classified as type I (e.g. rituximab, ofatumumab) or type II (e.g. tositumomab (B1), GA101, 11B8) according to their ability to redistribute CD20 in the plasma membrane and their activity in various effector assays (25-27). Type I (e.g. rituximab, ofatumumab) anti-CD20 monoclonal antibodies induce CD20 to redistribute into large detergent resistant microdomains (rafts), whereas type II (tositumomab-like) anti-CD20 monoclonal antibodies do not (50).

As discussed above, anti-CD20 mAbs can be designated as Type I or Type II by virtue of whether they redistribute CD20 into lipid rafts. This is done by the Tx-100 insolubility assay or by sucrose density gradient separation and western blotting. Both methods are described in Cragg et al Blood 2003 (43) as follows:

1 Assessment of Raft Associated Antigen by Triton X-100 Insolubility

As a rapid assessment of antigen presence in raft microdomains, we utilised a flow cytometry method based on Triton X-100 insolubility at low temperatures. In brief, cells were washed in RPMI/1% BSA and resuspended at $2.5 \times 10^6$/ml. Cells were then incubated with 10 µg/ml of an FITC conjugated mAb for 15 minutes at 37° C., washed in cold PBS/1% BSA/20 mM sodium azide, and then the sample divided in half. One half was maintained on ice to allow calculation of 100% surface antigen levels, whilst the other was treated with 0.5% Triton X-100 for 15 minutes on ice to determine the proportion of antigens remaining in the insoluble raft fraction. Cells were then maintained at 4° C. throughout the remainder of the assay, washed once in PBS/BSA/azide, resuspended and assessed by flow cytometry as detailed above. Similar results were obtained using indirect methods of detection. To determine the constitutive level of raft association of target antigens, cells were first treated with 0.5% Triton X-100 for 15 minutes on ice and washed in PBS/BSA/azide prior to binding of FITC-labeled mAb. To assess whether more antigen could be moved into the Triton X-100 insoluble fraction by additional cross-linking, cells were incubated with FITC-mAb as before, washed and then divided into four. Two of these samples were incubated with goat anti-mouse Ig F(ab')$_2$ fragments for 15 minutes on ice. After washing, one of the cross-linked and one of the non-cross-linked samples were lysed in Triton X-100 and washed as detailed above prior to flow cytometry.

2. Sucrose Density Gradient Separation and Western Blotting—Preparation of Lipid Raft Fractions and Western Blotting Monoclonal Ab (1 µg/$10^6$ cells) was added to cells at 37° C. Following 20 minutes incubation, cells were pelleted and lysed in ice-cold 1.0% Triton X-100 in MES-buffered saline (25 mM MES, pH 6.5, 150 mM NaCl, 1 mM phenylmethylsulfonyl fluoride, 5 µg/ml aprotinin, 5 µg/ml leupeptin, 10 mM EDTA). Lipid raft fractions were then prepared by sucrose density gradient centrifugation. Briefly, Lysates were mixed with an equal volume of 80% sucrose in lysis buffer, overlaid with a discontinuous 5-30% sucrose density gradient and then centrifuged at 200,000×g for 16 h. Fractions (0.5 ml) were collected and analysed by Western blotting. 15 ml aliquots of each fraction were diluted 1:1 in 2× loading buffer, heated to 95° C. for 5 min and separated on 15% SDS-PAGE gels, before transfer onto PVDF membranes and incubated with primary antibody (for example mouse anti-CD20, clone 7D1 to detect CD20 or anti-Lyn rabbit polysora; Serotec, UK to identify the raft fractions), followed by HRP-conjugated secondary antibody (Amersham Biosciences UK Ltd). Blots were visualised using ECL+plus (Amersham Biosciences UK Ltd).

Anti-CD20 mAbs can require the AxP motif in the large loop of CD20. (Ofatumumab and other Genmab antibodies do not). However, (Niederfelner et al. (51)) indicates Type II mAb bind to a slightly different region of the CD20 loop compared to Type I.

Preferably, in a composition, use, or method according to the invention the target cell is a cancer cell. More preferably, a cancer selected from non-Hodgkin lymphoma, including but not limited to follicular lymphoma, diffuse large B cell lymphoma, mantle cell lymphoma, or chronic lymphocytic leukaemia.

In one embodiment the invention provides compositions, uses and methods for treating cancer, in particular a B cell malignancy which is preferably selected from lymphomas, chronic lymphocytic leukemias, acute lymphoblastic leukemias, multiple myeloma, Hodgkin's and non-Hodgkin's disease, diffuse large B cell lymphoma, follicular lymphoma with areas of diffuse large B cell lymphoma, small lymphocytic lymphoma, mantle cell lymphoma, and diffuse small cleaved cell lymphoma or combinations thereof. In certain embodiments, the B cell malignancy is a lymphoma, such as non-Hodgkin's (NHL).

In another embodiment the invention provides compositions, uses and methods for treating an inflammatory disease. This may be an autoimmune disease, such as Hashimoto's thyroiditis, pernicious anemia, Adison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis or combinations thereof. In specific embodiments, the autoimmune disease is rheumatoid arthritis or systemic lupus erythematosus.

In preferred embodiments the treatment is of diseases including, chronic lymphocytic leukemia (CLL), non-Hodgkin lymphoma (NHL), B cell malignancies, Rheumatoid arthritis, systemic lupus erythematosus, dermatomyositis, systemic sclerosis and autoimmune blistering diseases.

In a preferred embodiment the treatment that is enhanced by use of the invention is treatment with an anti-CD20 mAb, such as rituximab.

Definitions

By "elevated" we include the meaning that the cells in question express higher levels of FcγRIIb on their surface than control or reference cells that express low or medium levels of FcγRIIb on their surface. For example, if the cells in question are a type of B cell, "elevated" levels of FcγRIIb expression would be recognized if the level of expression was higher than the normal (preferably median) level of expression of FcγRIIb by B cells of the same cell type. Alternatively, "elevated" levels would be recognized if the cells in question expressed FcγRIIb at a level higher than a different cell type which expresses FcγRIIb at low or medium level.

According to the invention, the greater the degree of elevation in FcγRIIb expression of target cells, the worse the predicted response of those cells to treatment with an antibody molecule that binds specifically to a surface antigen of the target cells and that has an Fc domain capable of binding FcγRIIb. Hence, the greater the elevation in FcγRIIb expression, the greater the benefit to be gained from the use of an agent that prevents or reduces binding of the Fc domain to FcγRIIb according to the invention as demonstrated in FIGS. 2D and 3A. After measuring FcγRIIb levels by IHC (FIG. 10B) and separating MCL samples into positive and negative for FcγRIIb, a clear clinical difference in response was seen following rituximab-based therapy. (FIGS. 10C and 10D).

Skilled persons can readily determine levels of expression of FcγRIIb on cells by a variety of known methods, such as the flow cytometry and immunohistochemical staining methods described in the accompanying Figures and examples.

A skilled person would appreciate that the "normal" and "elevated" expression level of FcγRIIb will vary between different cell types and different disease states and would be capable of identifying a "normal" and an "elevated" expression level of FcγRIIb for a given target cell or disease state using methods well known in the art and described herein. Exemplary levels of "normal" (or median) and "elevated" levels of FcγRIIb expression on certain cell types are provided in FIG. 2C. In these particular examples, in Follicular Lymphoma (FL) "normal" levels are approximately 50 (ratio of Geo MFI FcγRIIb to isotype control) and "elevated" levels are approximately 125 or 400 or more, whilst in Diffuse large B-cell lymphoma (DLBCL) "normal" levels are approximately 20 and "elevated" levels are approximately 80 or more, whilst in Mantle cell lymphoma (MCL) "normal" levels are approximately 60 and "elevated" levels are approximately 110 or 190 or more, and in chronic lymphoid leukemia (CLL) "normal" levels are approximately 100 and "elevated" levels are approximately 300 or more.

Preferably, the elevated FcγRIIb expression level is at least 1.1 fold increased over the normal (preferably median) expression level of cells of the same cell type (or of cells of a different cell type), or at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0. 21.0, 22.0, 23.0, 24.0 or 25.0 or more fold increased over the normal (or median) expression level of cells of the same cell type or of cells of a different cell type. Preferably they are at least 1.8 fold increased over the normal (or median) expression level of cells of the same cell type or of cells of a different cell type As shown in the accompanying examples, the inventors have determined that the level of FcγRIIb expression correlates with an increased modulation of mAb from the cell surface. Even higher levels of FcγRIIb expression give an even higher modulation, i.e. there is a correlation between degree of elevation of expression and modulation as shown in FIGS. 2D and 3A. In FIG. 2D the expression level of FcγRIIb is plotted versus the level of modulation observed. The correlation is such that the highest levels of FcγRIIb (e.g. >400) results in the lowest level of surface CD20 (<20%) i.e. the greatest effect on modulating the mAb from the cell surface. In FIG. 3A, low (18), medium (70) and high (124) levels of FcγRIIb were introduced into an FcγRIIb-negative cell line (Ramos) and this was directly correlated with reducing levels of cell surface CD20 (60, 40, 30% for low medium and high) in proportion to the expression of the FcγRIIb. FcγRIIb expression levels are given as a ratio of the Geometric Mean Fluorescent Intensity (Geo MFI) of FcγRIIb to isotype control Modulation reduces the amount of mAb left on the cell surface. mAbs require the Fc to engage with immune effector mechanisms (ADCC, ADCP, CDC) in order to delete target cells. Therefore reducing modulation with FcγRIIb blocking mAb will improve Fc-dependent effector functions. This is shown for ADCP (phagocytosis) in FIG. 8. Phagocytosis with rituximab alone was 40% but rose to 55% when the FcγRIIb was blocked by AT10.

By "antibody molecule" we include monoclonal antibodies, synthetic antibodies, recombinantly produced antibodies, multispecific antibodies, human antibodies, chimeric antibodies, camelized antibodies, single-chain Fvs (scFv), single chain antibodies, Fab fragments, F(ab') fragments, disulfide-linked Fvs (sdFv), intrabodies, or epitope-binding fragments of any of the above. Preferably, the antibodies of the invention are monoclonal antibodies, and more preferably, humanized or human antibodies.

Methods for the preparation and characterization of antibody molecules which are useful in the compositions, use and methods of the present invention are well known to skilled persons. For example, WO 2008/002933, in Section 5.3 to 5.3.1 pages 74-91, describes the preparation and characterization of monoclonal antibodies that bind specifically to a target cell surface antigen such as CD20 or FcγRIIb. Useful antibodies that specifically bind FcγRIIb and CD20, including monoclonal antibodies produced by hybridomas deposited under the Budapest Treaty, are also disclosed on pages 15 to 21 of WO 2008/002933, the disclosure of which is incorporated herein by reference.

By "specifically binds" we include agents such as antibody molecules that bind to a target antigen but do not bind (cross-react) to other antigens or bind such antigens more weakly, i.e. with a lower affinity than the target antigen. For example, an antibody that specifically binds to FcγRIIB may bind to other peptides or polypeptides with lower affinity as determined by, e.g., immunoassays, BIAcore, or other assays known in the art. Preferably, antibodies that specifically bind to FcγRIIB or a fragment thereof do not cross-react with other antigens. Antibodies that specifically bind to FcγRIIB can be identified, for example, by immunoassays, BIAcore, or other techniques known to those of skill in the art. An antibody or a fragment thereof binds specifically to a FcγRIIB when it binds to FcγRIIB with higher affinity than to any cross-reactive antigen as determined using experimental techniques, such as western blots, radioimmunoassay (RIA) and enzyme-linked immunosorbent assays (ELISAs) (See Fundamental Immunology Second Edition, Raven Press, New York at pages 332-336 (1989) for a discussion regarding antibody specificity) and binds FcγRIIB, particularly human FcγRIIB, more particularly native human FcγRIIB, with a greater affinity than said antibody or a fragment thereof binds FcγRIIA, particularly human FcγRIIA, more particularly native human FcγRIIA. Representative antibodies are disclosed in US Patent Application Nos. 2004-0185045; 2005-0260213; and 2006-0013810, which are all herein expressly incorporated by reference in their entireties.

Preferably certain FcγRIIB antibodies used in combination with CD20 antibodies in the compositions and methods of the invention bind the extracellular domain of native human FcγRIIB. In some embodiments, the antibody or a fragment thereof binds FcγRIIB with at least 2 times greater affinity than said antibody or a fragment thereof binds FcγRIIA. In other embodiments, the antibody or a fragment thereof binds FcγRIIB with at least 4 times, at least 6 times, at least 8 times, at least 10 times, at least 100 times, at least 1000 times, at least $10^4$, at least $10^5$, at least $10^6$, at least $10^7$, or at least $10^8$ times greater affinity than said antibody or a fragment thereof binds FcγRIIA. In a preferred embodiment, said antibody or a fragment thereof bind FcγRIIB with 100 times, 1000 times, $10^4$ times, $10^5$ times, $10^6$ times, $10^7$ times, $10^8$ times greater affinity than said antibody or a fragment thereof binds FcγRIIA.

BRIEF DESCRIPTION OF THE DRAWINGS

Examples which embody aspects of the invention will now be described with reference to the accompanying figures in which:

FIGS. 1A-1B. Type I mAb internalize from the cell surface of normal and malignant human B-cells.

FIG. 1A. Primary CLL cells were cultured with Tosit-488, GA101gly-488, Ritux-488 or Ofatum-488 (all at 5 µg/ml) for 2 or 6 h. Cells were then harvested and washed twice before addition of anti-Alexa-488 to one half of the sample for 30 min at 4° C. to discriminate between internalized and non-internalized mAb. Surface accessible CD20(%) was determined using the following calculation: Surface accessible CD20+(Pre-quench Geo MFI—Post-quench GEO MFI)/(Pre-quench Geo MFI)×100. Each point represents a sample from a different CLL patient. Statistical analysis was performed using the Wilcoxon paired test, **p value<0.001, and medians are shown. FIG. 1B. A variety of primary B cell tumors and normal B cells from healthy volunteers was then examined in the same assay with Tosit-488 or Ritux-488. Statistical analysis was performed using the Mann Whitney test and medians are shown.

FIG. 1C. Correlation between modulation and known CLL prognostic factors: CLL cases were phenotyped for IgVH gene mutational status, Zap-70 and CD38 expression, and internalization assays were performed on these samples to assess modulation Correlation between each prognostic feature and CD20 modulation was performed by Spearman's correlation analysis. No correlation was seen with each prognostic factor (p>0.05). FIG. 1D. Similarly, sIg status, ability of cells to elicit calcium flux and viability of CLL cells were assessed, and compared with CD20 modulation. Again, no correlation was seen. FIG. 1E. CD20 expression of CLL cells were assessed by FACS using Ritux-488, and compared with CD20 modulation. A weak correlation was seen (Spearman r value −0.34, p=0.038). Subsequent analysis using multivariate regression of CD20 and FcγRIIb expression against CD20 modulation showed that the weak correlation with CD20 was not significant (p=0.638). FIG. 1F. sIg expression of IgM-positive CLL cases were determined by FACS and the level of expression compared with CD20 modulation. No correlation was found (p>0.05). FIG. 1G. CLL cases were cultured with Rit m2a-488 for 2 h and internalization assay performed as in FIG. 1A. Within a single CLL case, variation in CD38 expression was seen. The FACS plots show samples pre-quenching (left) and post-quenching (right). The corresponding histograms highlight that $CD38^{+ve}$ and $CD38^{-ve}$ cells within a single sample modulated at the same rate. $CD38^{+ve}$ and $CD38^{-ve}$ cells are represented by solid and hollow peaks respectively. These results are representative of 3 different cases.

FIG. 2A. The internalization assay described in 1a) was repeated after culturing CLL cells for 6 h with Alexa-488-labelled fragments of rituximab; Fab', $F(ab')_2$ and IgG. Data represent the mean levels of modulation+/−SD for 3 different CLL samples. FIG. 2B. CLL cells were cultured with Tosit-488, Ritux-488+/−AT10 and Rit m2a-488 as in 1a) for 2 and 6 h. Mean+/−modulation are shown from 6 different CLL samples. Addition of anti-FcγRII mAb AT10, to rituximab, reduced CD20 modulation to levels similar to Rit m2a, whereas addition of AT10 to Rit m2a made no significant difference to modulation. FIG. 2C A variety of normal and malignant B cell samples were stained for FcγRIIb expression with AT10-PE. The histogram shows the diversity of FcγRIIb expression in 3 different CLL cases, representing nominal high (black line), medium (dark gray line) and low expressors (light gray line). The scatterplot shows differences in FcγRIIb expression across healthy B cells, CLL, SLL, MCL, FL and SLBCL. FcγRIIb expression was expressed as a ratio of FcγRIIb:isotype control Geo MFI to control small differences due to inter-experimental variation. Median values are shown. FIG. 2D. FcγRIIb expression was plotted against CD20 modulation across all NHL subtypes and normal B cells (obtained from internalization assay described in 1A) and co-cultured with Ritux-488 for 6 h). Analysis was performed using a Spearman's correlation assuming a non-parametric distribution. A strong correlation was demonstrated. Spearman r value=−0.74, 95% confidence interval between −0.83 and −0.61 and p<0.0001.

FIGS. 3A-3B. FcγRIIb expression is a major determinant of CD20 modulation. FIG. 3A. Ramos cells transfected with FcγRIIb were sorted to express low, medium and high levels of FcγRIIb and assessed in the internalization assay using Tosit-488 and Ritux-488 at the 6 h time-point alongside mock-transfected cells. The bars represent means values+/−SD from independent experiments. Geo MFI values for FcγRIIb expression of the sorted cells are listed on the right. FIG. 3B. The internalization assay was repeated using Tosit-488 and Ritux-488 on normal Ramos cells, Rx3 cells (which lack BCR expression), mock-transfected Rx3 cells and FcγRIIb-transfected Rx3 cells following incubation for 6 h. Data points from 5 independent experiments are shown along with the median value.

FIGS. 4A-4E. CD20 and FcγRIIb co-ligation occurs predominantly in a cis fashion and leads to activation of FcγRIIb. FIG. 4A. Raji cells were cultured with the specified mAb (10 µg/ml) for 2 h at 37° C. before harvesting, lysis and subsequent immunoblotting for phosphorylated FcγRIIb. FIG. 4B Left panel; PKH26-labeled Ramos cells ($FcγRIIb^{-ve}$, R1) were mixed 1:1 with sorted high FcγRIIb-expressing Ramos transfectants (R2) (described in FIG. 3A). Right panel; modulation of CD20 on $FcγRIIb^{+ve}$ and $FcγRIIb^{-ve}$ cells after culture with Ritux-488 for 6 h. As controls, both populations were also cultured alone. Data represent the mean levels of modulation+/−SD from 3 independent experiments. FIG. 4C. In a similar experiment, a low FcγRIIb-expressing CLL was PKH26-labeled then mixed 1:1 with a higher FcγRIIb-expressing CLL. The experiment was performed three times, each time with a different high FcγRIIb-expressing CLL. FcγRIIb levels (Geo MFI) were 42 (low) and 275, 306 and 165 for the high expressors. The internalization assay was then performed as in 4B. Data represent the mean levels of modulation+/−SD. FIG. 4D. Different CLL samples were cultured with Ritux-488 for 6 h at 20, 4 and $1 \times 10^5$ cells/ml, and the internalization assay performed at 6 h as before. FIG. 4E. Raji cells were cultured at 20, 4, and $1 \times 10^5$ cells/ml with the specified mAb (10 μg/ml) for 2 h at 37° C. Images were captured using a bright field microscope to demonstrate differences in cell proximity. Cells were then harvested and assessed by immunoblotting for phosphorylated FcγRIIb as described in FIG. 4A.

FIG. 5A. CLL cells were incubated with either Tosit-488 or Ritux-488 for 2 h and then stained with anti-CD19-APC and AT10-PE. Data show the mean+/1 SD for FcγRIIb expression as a % of untreated (n+6 CLL samples). FcγRIIb expression after Ritux-488 was significantly lower than after Tosit-488, *p<0.05. FIG. 5B. CLL cells were washed, fixed and permeabilized before staining with AT10-647 (blue), washing and analysis with confocal microscopy. This image represents the FcγRIIb staining pattern in unstimulated cells. FIG. 5C. The same CLL sample was cultured with Ritux-488 for 30 min then treated as described in 5b). Cells at this time-point displayed obvious co-localization between Ritux-488 (green) with AT10-647 (blue). FIG. 5D. CLL cells were incubated with Tosit-488 for 6 h before preparation for microscopy as in 5B. In addition, cells were also stained with biotinylated LAMP-1 and streptavidin-546 (red) to stain for lysosomes. Tosit-488 remained uniformly on the surface and AT10-647 staining was unchanged from baseline seen in 5B. There was no co-localization with LAMP-1. FIG. 5E. CLL cells were treated with Ritux-488 for 6 h and assessed as in FIG. 5D). Two representative cells are shown here. The top cell shows unambiguous co-localization between Ritux-488 and AT10-647, but no co-localization with LAMP-1. The bottom cell shows co-localizatoin of all three fluorochromes. In each case the bright field (BF) image is shown from the same cell. Scale bars represent 5 m.

FIG. 8. Enhanced phagocytosis of CLL cells treated with rituximab by co-incubation with a FcγRII blocking mAb. Monocytes were derived from healthy volunteers and differentiated into macrophages with M-CSF in a 6-well plate for a minimum period of 7 days prior to use. Macrophages were then harvested and allowed to adhere in a 96-well plate at $5 \times 10^5$ cells/well for a minimum of 2 hours prior to addition of CFSE-labelled CLL cells. CSFE-labelled CLL cells were untreated or opsonised with 10 μg/ml of rituximab (ritux) and the FcγRIIb blocking mAb AT10 (fab')$_2$ for either 15 mins or 6 h before washing twice and adding to macrophages (1:1 ratio) for at least 30 mins. Anti-CD16 f(ab)$_2$-APC (5 μg/ml) was then added to each well for 15 mins at Room Temperature (RT) to stain macrophages and then wells washed once with Facs wash (PBS BSA azide) at RT. Further ice cold FACS wash was added and the plate incubated on ice for 10 minutes prior to harvesting for analysis by Facs. % Double-positive macrophages represent % of CD16+CFSE+ positive cells, expressed as a total of % CD16+ cells. N=3 replicates, line represents mean. The data clearly show that phagocytosis of CLL cells is higher when the rituximab has been added for only 15 minutes, compared to 6 h. This decrease in efficacy is associated with modulation of the rituximab from the cell surface and can be reversed by treatment with the FcγRIIb blocking mAb AT10. Importantly, the FcγRIIb mAb is only added to the CLL cells and so has no effect on the macrophages themselves. Furthermore, only Fab2 fragments of AT10 are used and therefore increased phagocytosis cannot occur as a result on more mAb being bound to the CLL cell surface. This conclusion is also supported by the observation that no increase in phagocytosis is observed following incubation for only 15 minutes (a time at which v little rituximab modulation would have occurred).

FIG. 9. FcγRIIb expression by IHC. Paraffin-embedded tissues were stained for FcγRIIb expression using anti-CD32b specific mAb, EP888Y. Images from 4 different FL patients are shown (×40 total magnification, and ×150 magnification inset). FcγRIIb expression was also examined by flow cytometry by staining matching viable cells with AT10-PE. FcγRIIb expression obtained by flow cytometry is shown on the top left corner of each image.

FIGS. 10A-10D. FcγRIIb levels predict clinical outcome in rituximab-treated MCL patients. As proof-of-concept of our in vitro findings, we retrospectively examined the FcγRIIb expression of a cohort of MCL patients who had received rituximab. Diagnostic paraffin-embedded tissue was stained by immunohistochemistry using an FcγRIIb-specific mAb (FIG. 11). Strong membrane staining was seen in FcγRIIb+ve but not FcγRIIb-ve lymphoma samples. The FcγRIIb staining shown in FIGS. 10A and 10B by IHC correlated with the FcγRIIb expression shown by flow cytometry as shown in FIG. 2D (with the value determined by flow cytometry in 2D shown as the number inset in FIGS. 10A and 10B). These results correlated with FcγRIIb expression of corresponding DMSO-frozen samples, obtained by flow cytometry (FIG. 2C, inset values). Despite studying only a small cohort of 16 MCL patients, patients with FcγRIIb-ve lymphoma had significantly better median progression-free survival than those with FcγRIIb+ve cells (median 852 and 189 days, respectively). FIG. 10C shows the differences in survival in the FcγRIIb+ and − subsets. The groups were comparable in terms of clinical features (MCL international prognostic index, data not shown), but there was heterogeneity in chemotherapy types used. In order to address this, we examined the results in those patients treated with either single-agent rituximab or fludarabine, cyclophosphamide and rituximab (FCR) for initial therapy, and similar results were observed. FIG. 10D shows the differences in survival in the FcγRIIb+ and − subsets after the patient cohorts were further controlled as discussed.

Ability of anti-CD32b mAb to block modulation of rituximab. The Y axis shows surface accessible CD20(%). Rituximab-alexa 488 was added to Ramos cells transfected with CD32B in the presence or absence of different CD32b blocking mAb (WT or 297Q (nq) mutants) and modulation assessed after 1, 2, 6 and 24 h. As a control for the blocking ability of CD32 mAb we also included the dual CD32a and b specific mAb, AT10 (IgG and Fab2 fragments (Fab)), alongside a negative control, isotype matched irrelevant mAb (iso wt or nq). Finally, ALEXa 488-labeled B1 was included as a control mAb that does not modulate rapidly. The data clearly indicate that all 3 nCoDeR© mAb (C1, C11 and C13) are able to block the modulation of rituximab in either the wt or 297q format. In particular the C11 mAb was extremely effective.

Figure 13:
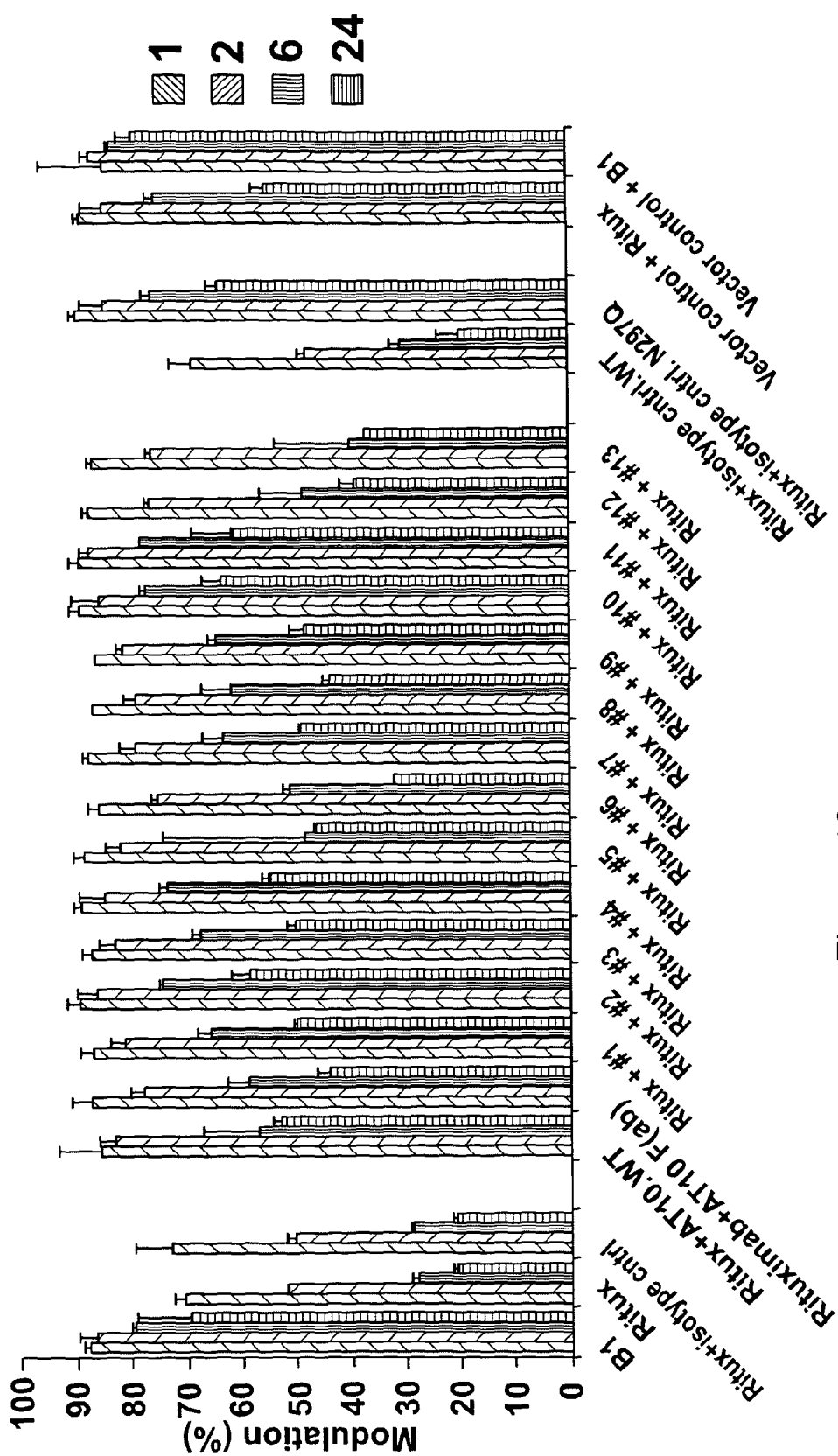

FIG. 13. Ability of anti-CD32b mAb to block modulation of rituximab. All 13 mAb (nq) and C11 as a wt Rituximab-alexa 488 was added to Ramos cells transfected with CD32B in the presence or absence of different CD32b blocking mAb (WT or 297Q mutants) and modulation assessed after 1, 2, 6 and 24 h. The Y axis shows surface accessible CD20(%). As a control for the blocking ability of CD32 mAb we also included the dual CD32a and b specific mAb, AT10 (IgG and Fab2 fragments (Fab)), alongside a negative control, isotype matched irrelevant mAb (iso wt or nq). Finally, ALEXa 488-labeled B1 was included as a control mAb that does not modulate rapidly. In addition, control CD32 negative Ramos cells were included to allow estimation of the maximal effect of the CD32 blocking mAb. The data clearly indicate that all the majority of nCoDeR© mAb were able to block the modulation of rituximab. In particular the C10 and C11 mAb were extremely effective and appeared to block modulation almost completely even at 24 h.

Figure 14A:
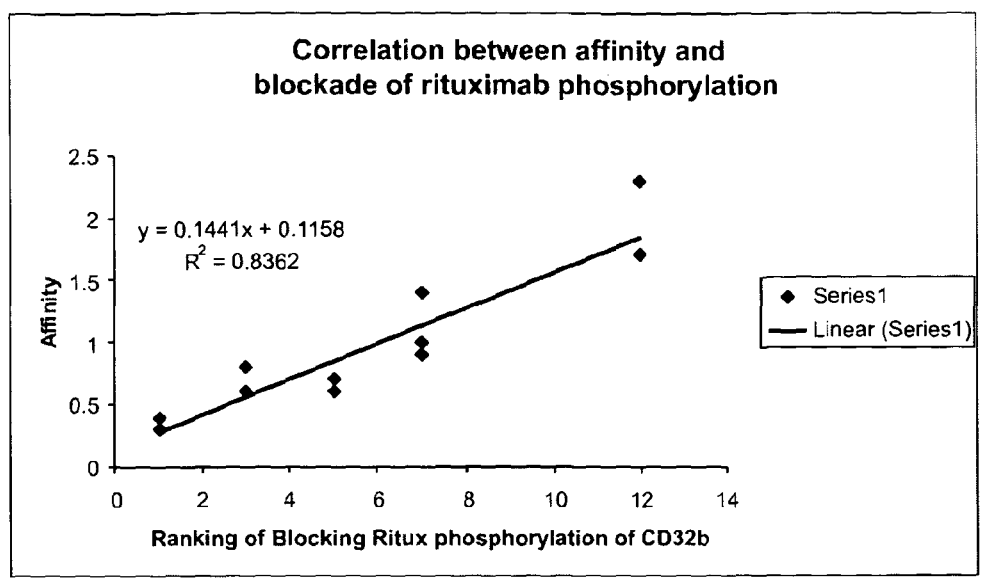

FIG. 14A. Correlation between affinity and the ability of ant-CD32b blocking mAb to prevent phosphorylation of CD32b after rituximab binding.

The relative affinity of the mAb was determined by a dose titration experiment measuring mAb binding to CD32B transfected CHO cells. Briefly, CD32B transfected adherent CHO K1 cell were seeded into FMAT plates. IgG were titrated in 1:2 dilutions from 30 nM to approximately 0.015 nM and left to bind for 1 h at room temperature. After washing bound IgG were detected with anti-human-IgG-APC. Finally, the plates were washed and read in the FMAT (Applied Biosystems). This gives an EC50 value for mAb binding to target expressing cells and can be translated to a relative affinity. This relative affinity was then correlated with the ability of anti-CD32b blocking mAb to prevent phosphorylation of CD32b after rituximab binding. This was determined by stimulating cells with rituximab in the presence or absence of anti-CD32b mAb and then performing western blotting for phospho-CD32b. The CD32b mAb were then ranked according to their ability to block the CD32 phosphorylation with 1 being the most effective. There was evidently a close correlation between the affinity of the mAb and the ability to block CD32b phosphorylation.

Figure 14B:
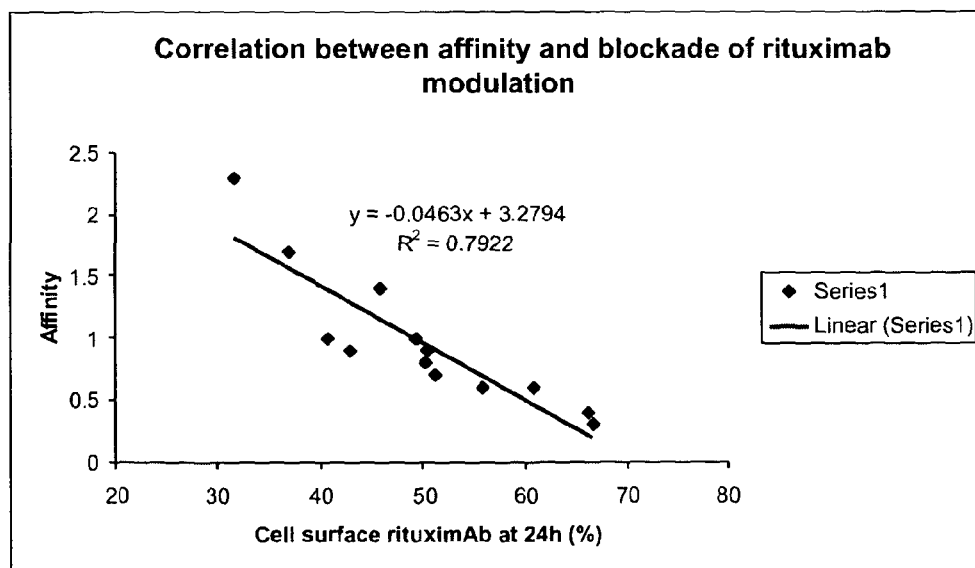

FIG. 14B. Correlation between affinity and the ability of ant-CD32b blocking mAb to prevent modulation of rituximab.

Correlation between affinity of the ant-CD32b blocking mAb and their ability to prevent rituximab modulation. The relative affinity of the mAb was determined by a dose titration experiment measuring mAb binding to CD32B transfected CHO cells. Briefly, CD32B transfected adherent CHO K1 cell were seeded into FMAT plates. IgG were titrated in 1:2 dilutions from 30 nM to approximately 0.015 nM and left to bind for 1 h at room temperature. After washing bound IgG were detected with anti-human-IgG-APC. Finally, the plates were washed and read in the FMAT (Applied Biosystems). This gives an EC50 value for mAb binding to target expressing cells and can be translated to a relative affinity. This relative affinity was then correlated with the ability of ant-CD32b blocking mAb to prevent modulation of rituximab on CD32b-transfected Ramos cells (shown in the previous figure). There was evidently a strong correlation between the affinity of the mAb and the ability to block rituximab modulation. This data confirms the central role of CD32B in accelerating the modulation of rituximab from the target cell surface.

Figure 15:
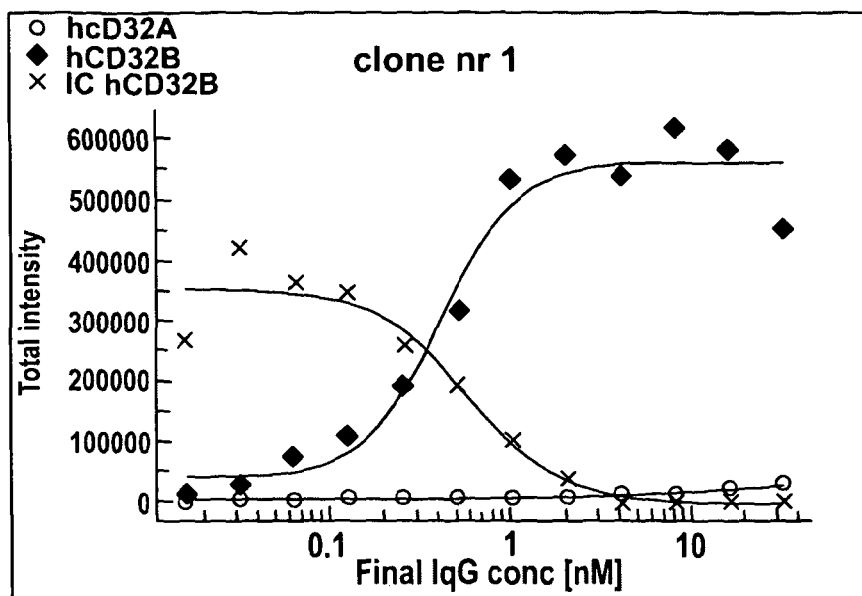

FIG. 15. As mediated by clone 1. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 1. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 16:
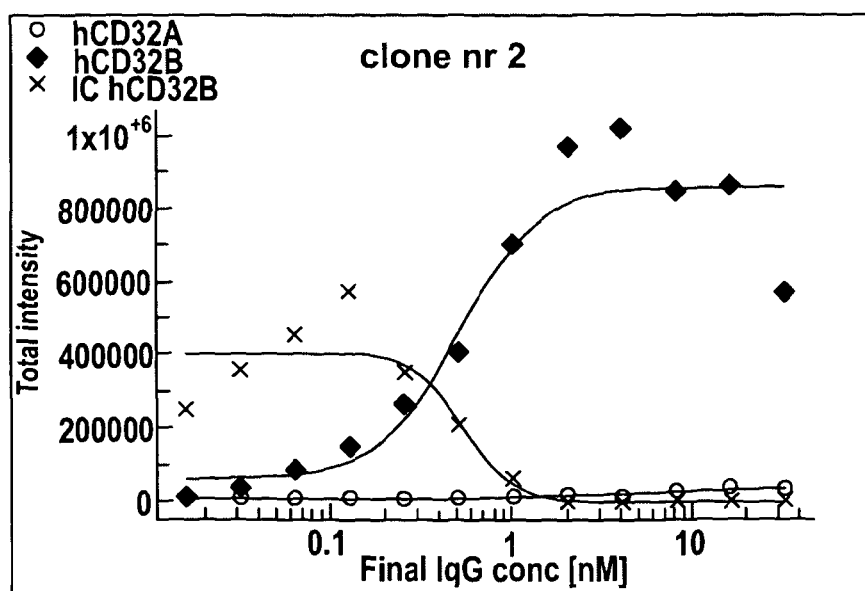

FIG. 16. As mediated by clone 2. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 2. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 17:
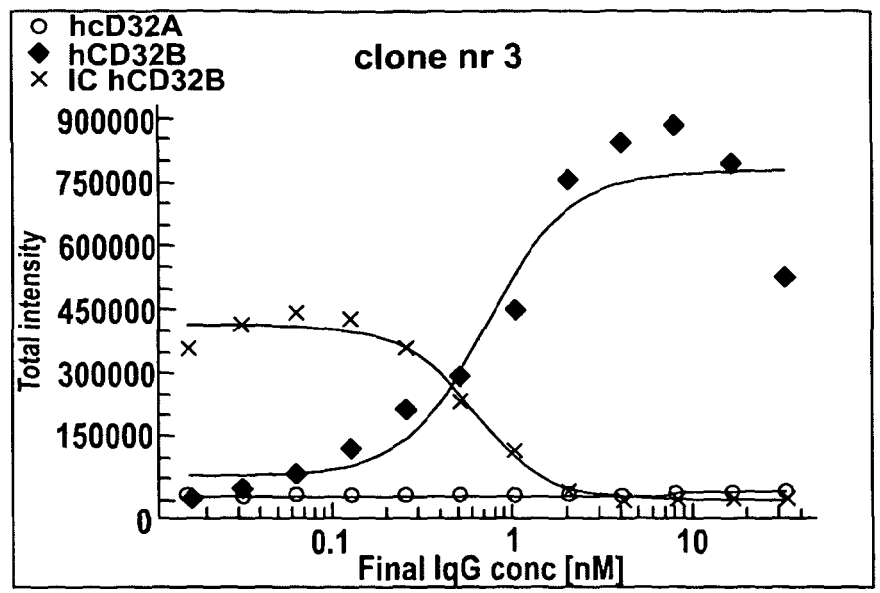

FIG. 17. As mediated by clone 3. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 3. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 18:
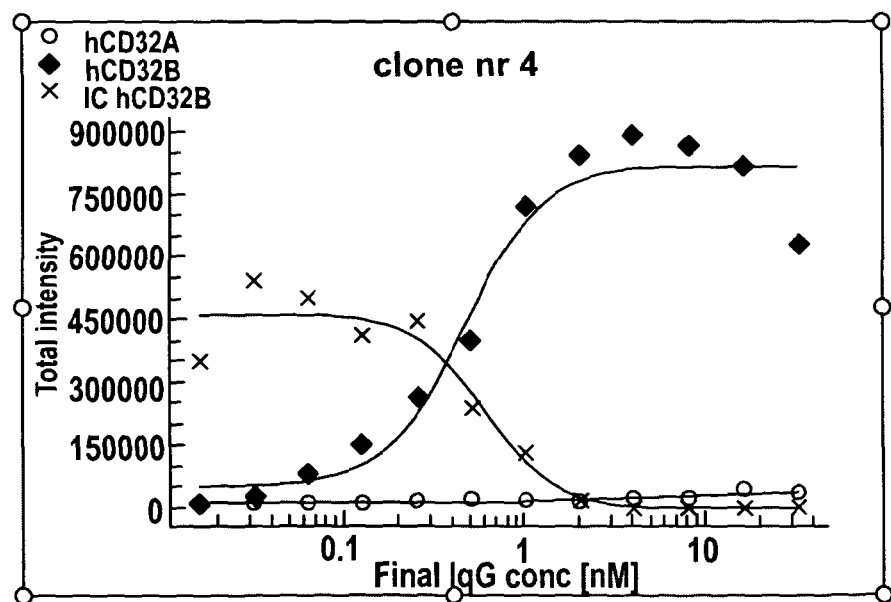

FIG. 18. As mediated by clone 4. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 4. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 19:
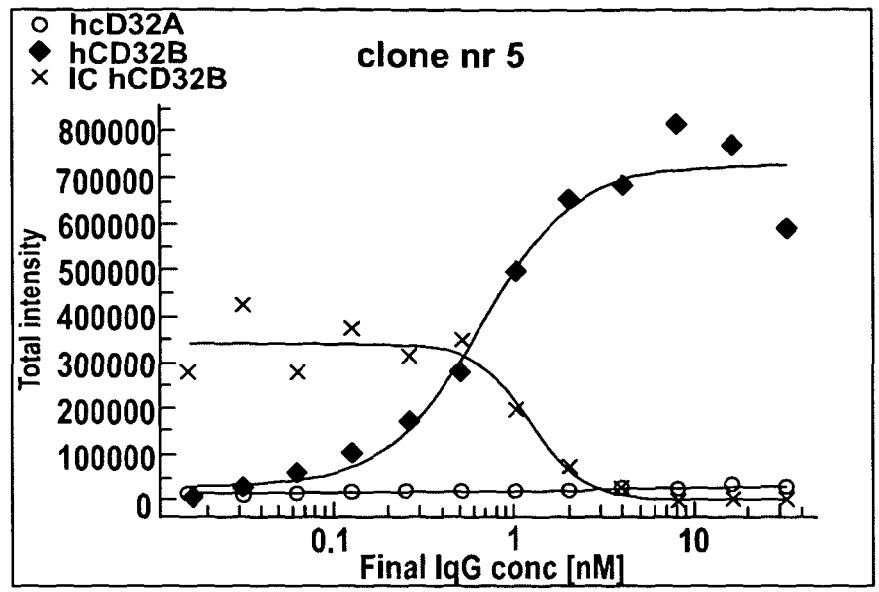

FIG. 19. As mediated by clone 5. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 5. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 20:
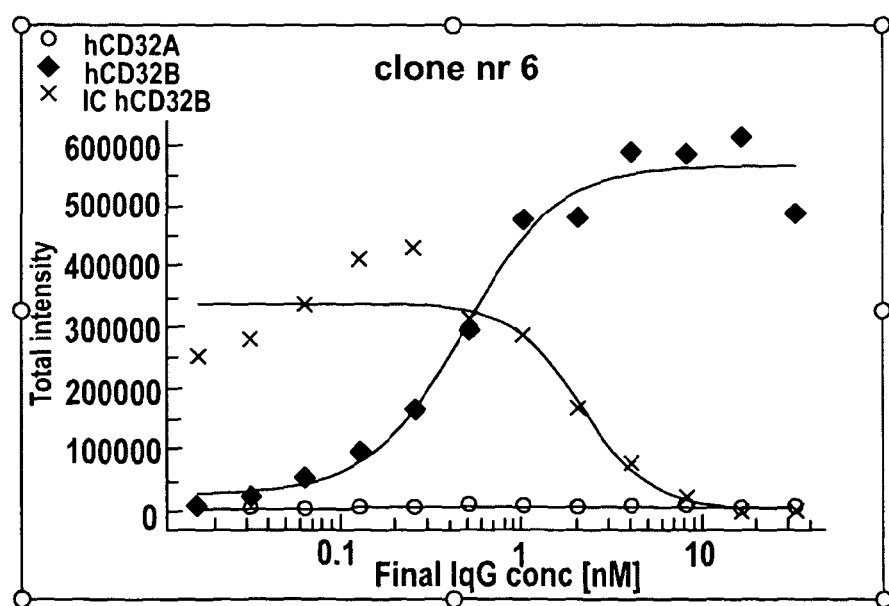

FIG. 20. As mediated by clone 6. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 6. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 21:
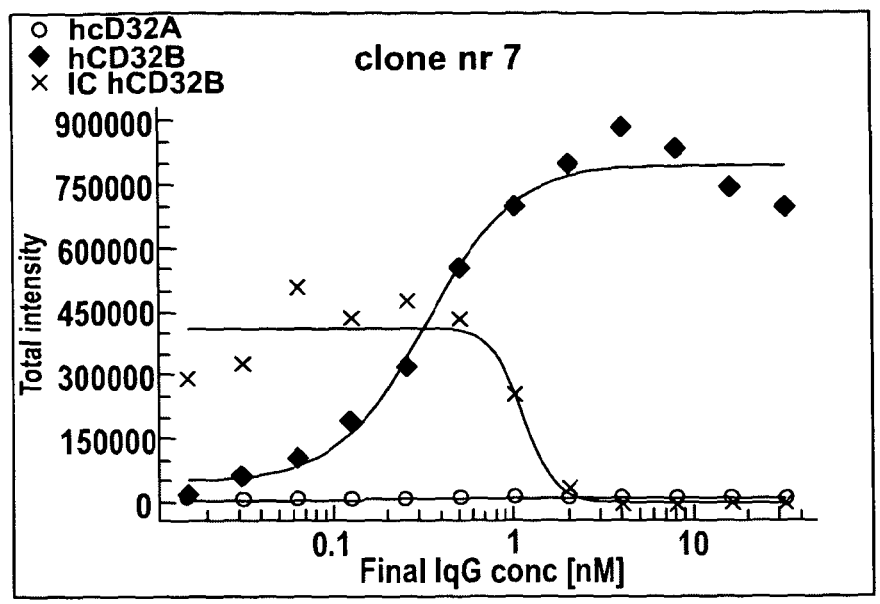

FIG. 21. As mediated by clone 7. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 7. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 22:
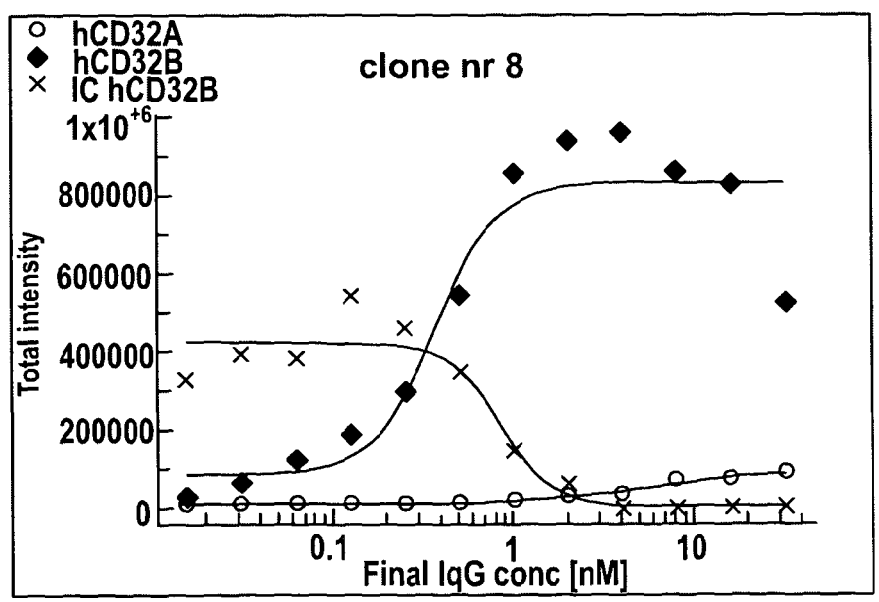

FIG. 22. As mediated by clone 8. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 8. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 23:
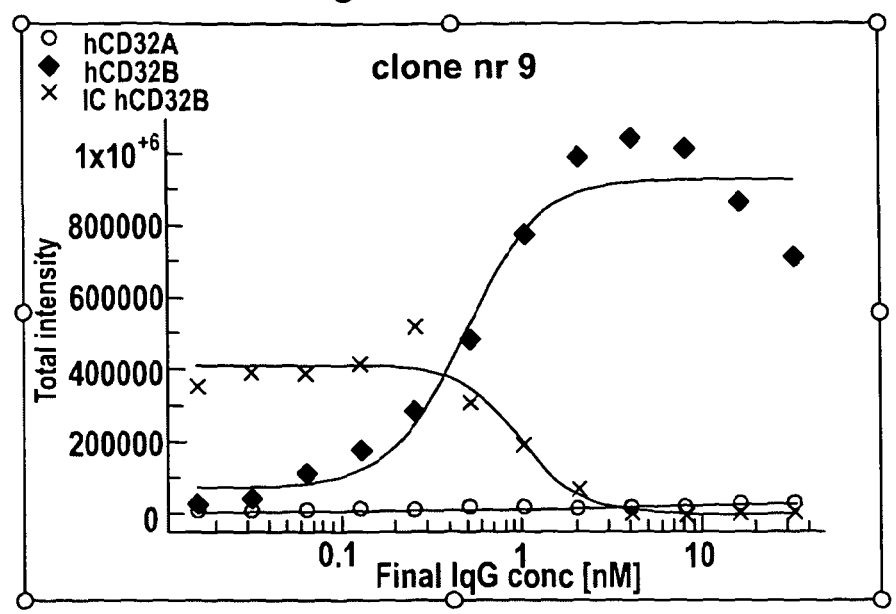

FIG. 23. As mediated by clone 9. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 9. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 24:
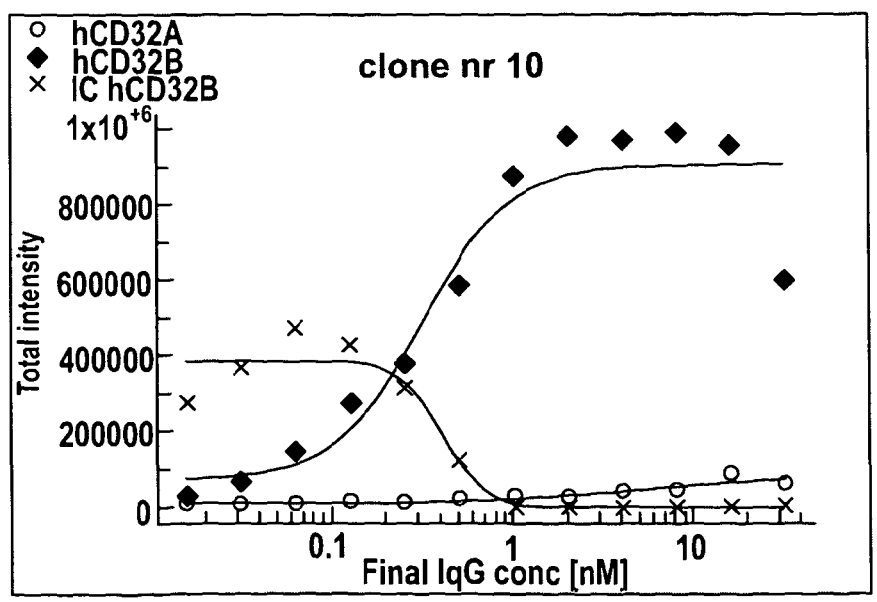

FIG. 24. As mediated by clone 10. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 10. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 25:
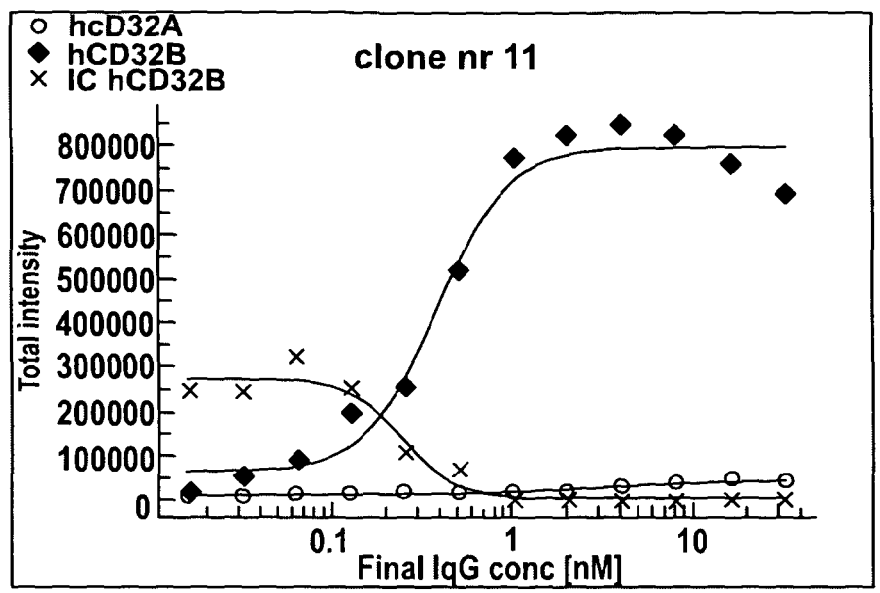

FIG. 25. As mediated by clone 11. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 11. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 26:
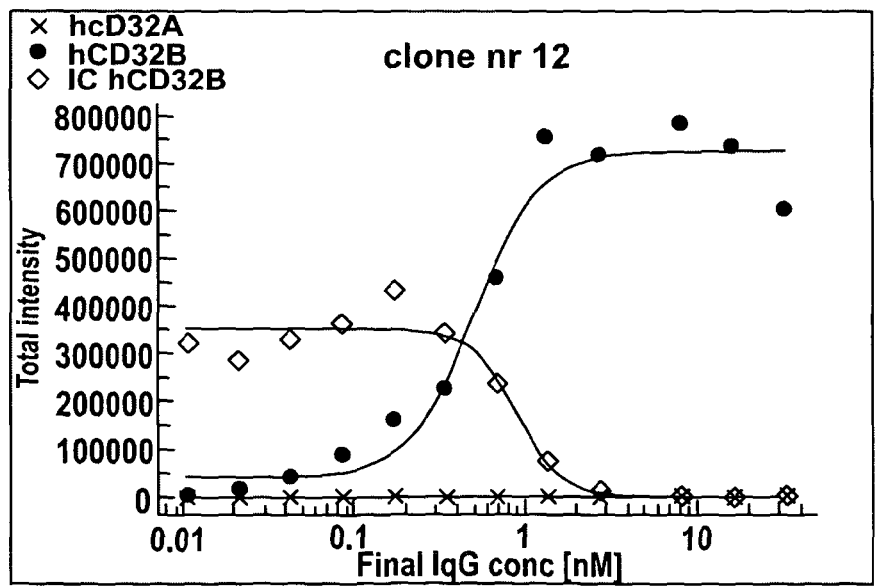

FIG. 26. As mediated by clone 12. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 12. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 27:
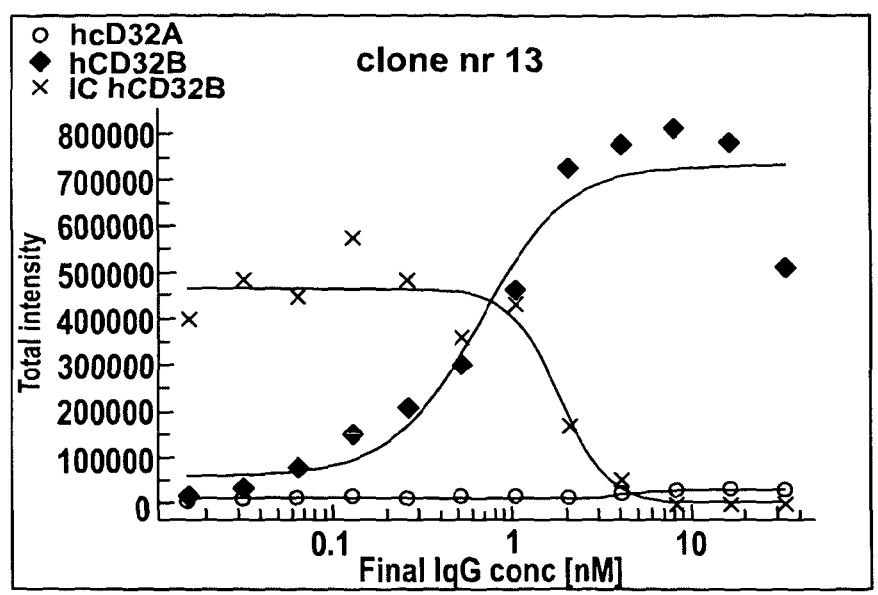

FIG. 27. As mediated by clone 13. Dose dependent binding to hCD32B transfected cells and dose dependent binding and inhibition of immune complex to hCD32B transfected cells.

Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells. As mediated by clone 13. Cells were seeded into FMAT plates. Immune complexes were prepared by coating FITC to BSA and thereafter mix this with a 10:1 molar ratio with a FITC specific hIgG1 antibody. The total intensity reflects binding, the higher intensity the higher binding. The binding is either immune complex (IC) or mAb's.

Figure 28:
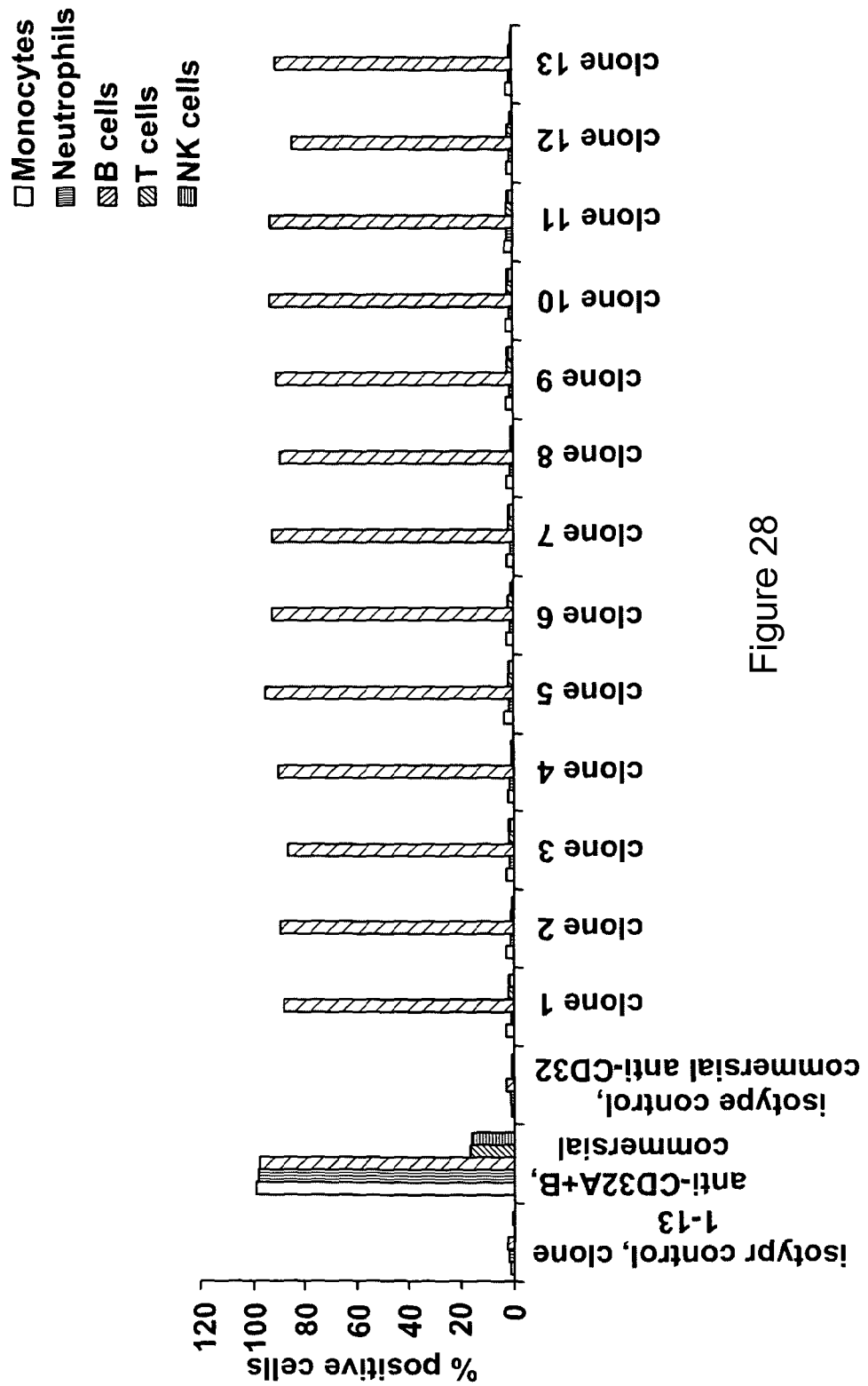

FIG. 28. Showing cell specificity of the anti-CD32B antibodies.

PBMCs isolated from peripheral blood was prepared using Ficoll density gradient. Cells were stained with cell specific markers and evaluated for binding of the CD32B specific antibodies. As shown in the figure, only B cells (CD19+ cells) stained positive with clone 1-13.

Figure 29:
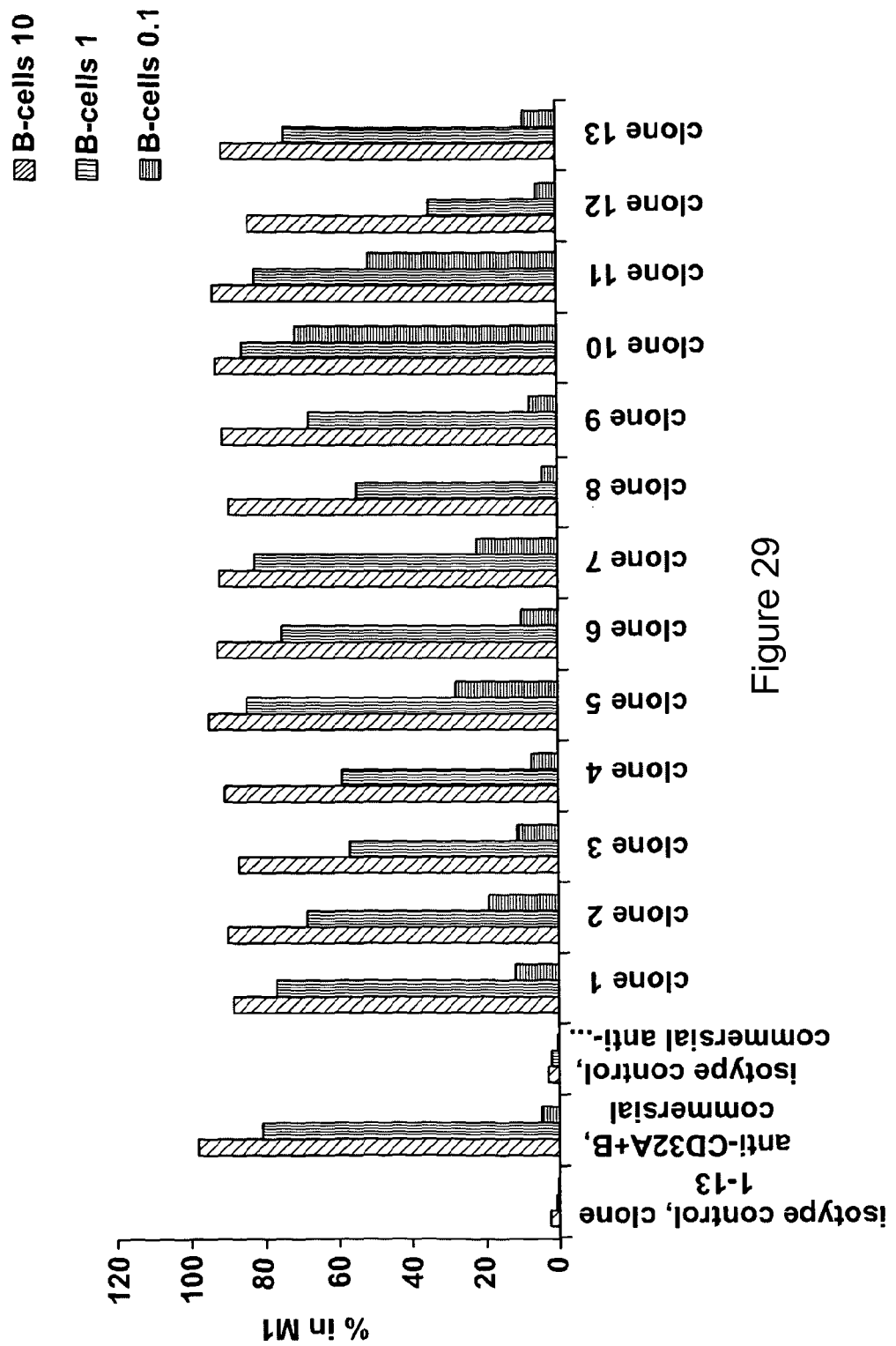

FIG. 29. Dose dependent staining of B cells by clone 1-13.

PBMCs isolated from peripheral blood was prepared using Ficoll density gradient. Cells were stained with CD19 and thereafter with 10, 1 or 0.1 mg/ml CD32B specific antibodies as indicated. In this figure, B cells (known to express CD32B) have been gated out using a CD19 specific mAb. This gate is called "M1". When the concentration of CD32B mAb is decreased, the number of B cells stained drops from nearly 100% down to much lower values, showing a specific and dose dependent staining of B cells, as expected from a CD32B specific mAb.

Figure 30:
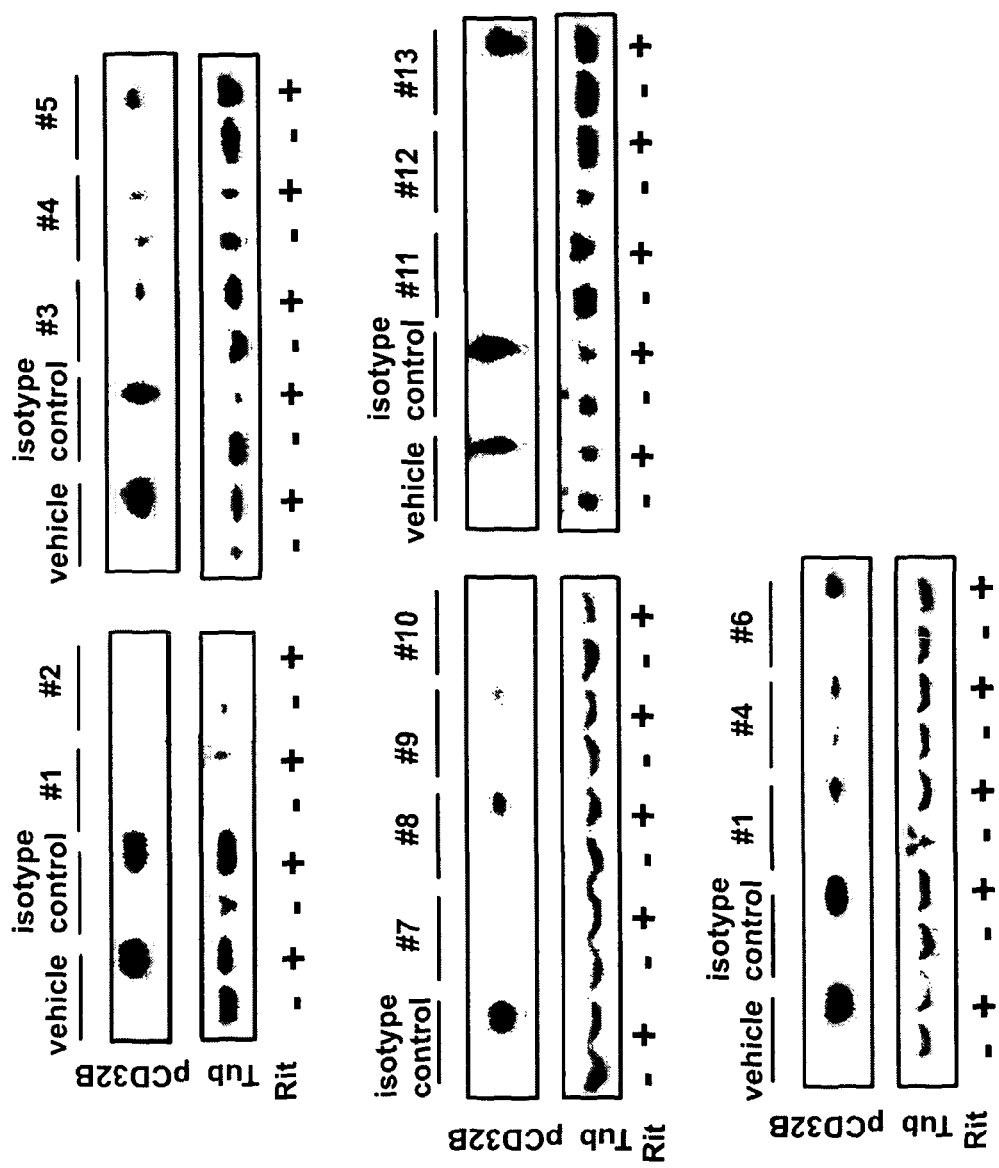

FIG. 30. Capacity of each mAb to inhibit Fc-mediated CD32B phosphorylation.

Raji cells (CD32B positive) where treated with Rituximab (Rit), which caused phosphorylation of CD32B. This where done in absence or presence of CD32B specific mAb's 1-13 and the figure demonstrate each mAb's capacity to inhibit Fc mediated CD32B phosphorylation. "TUB"=tubulin control.

FIG. 31. The effect of CD32b on the rate of modulation of type I anti-CD20 mAbs.

The ability of CD32b to precipitate the internalisation of other Type I anti-CD20 mAb. Alexa-488 labelled versions of each mAb were incubated with pCDNA3-transfected Ramos or CD32B-transfected Ramos cells for 1 or 6 hr and the extent of modulation determined as before. mAb used were rituximab (RTX), in-house produced ofatumumab (OFA) and tositumumomab (Tos). The data clearly show that the rate of internalisation of OFA is similar to that of RTX and is accelerated by the presence of CD32b.

FIG. 32. Anti-CD19 mAb also internalize from the cell surface of malignant human B-cells in a manner which is partially dependent upon CD32B.

Ramos huCD32b transfectants. Internalisation with other surface antigens can also be effected by CD32b expression. The modulation assay was performed as before with different mAb in the presence (+) or absence (−) of CD32 BLOCKING with AT10. Ramos CD32B TRANSFECTANTS were used in this 6 h assay. *p<0.05. f3.3=MHC Class II; RFB9=CD19; RTX=rituximab. If the mAb remains on the cell surface it can be quenched. If it is internalised it cannot be quenched. The lower the % quenched, the higher the level of internalisation. The data clearly show a significant reduction in surface modulation for RTX and RFB9 mAb, and less of a reduction for F3.3 mAb, after incubation with CD32 blocking. These data indicate that target antigens such as CD19 can also internalize from the cell surface of malignant human B-cells in a manner which is partially dependent upon CD32B and can be blocked by anti-CD32b mAb.

Figure 33:
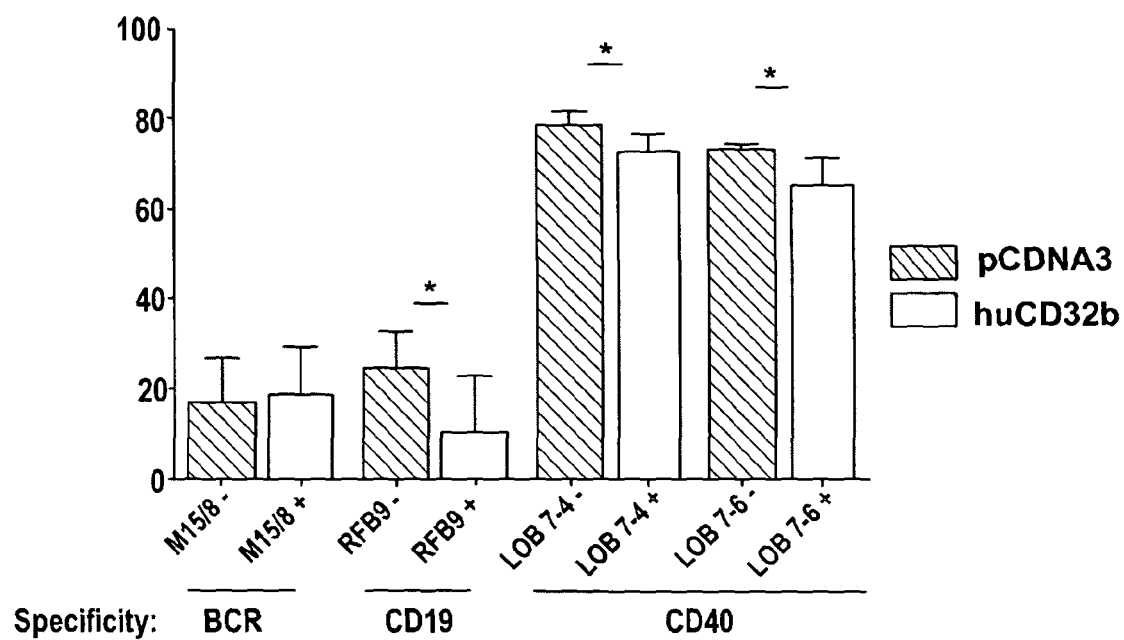

FIG. 33. Internalisation with other surface antigens can also be effected by CD32b expression. Alexa-488 labelled versions of each mAb were incubated with pCDNA3-transfected Ramos or CD32B-transfected Ramos cells for 24 h and the extent of modulation determined as before. *=p<0.05. The y axis shows modulation/internalisation or surface accessible antigen (%). The figure shows this because the amount of internalisation/modulation is increased in the presence of huCD32b. Note that for both anti-CD19 and anti-CD40 mAb there is a statistically significant (*, p<0.05) decrease in cell surface antigen in the presence of CD32b.

FIG. 34. Amino acid sequences of the constant regions of the 14 antibody clones directed against human CD32B in the IgG1-λ format. Amino acid sequences of the IgG1-CH and λ-CL regions are shown.

FIG. 35. Amino acid sequences of the variable regions of antibody clone 1 directed against human CD32B. Amino acid sequences are shown for the VH and VL regions. The labelled CDR sequences are indicated as boxed sequences separated by the labelled framework regions.

FIG. 36. Amino acid sequences of the variable regions of antibody clone 2 directed against human CD32B. Amino acid sequences are shown for the VH and VL regions. The boxed sequences represent the CDR sequences.

FIG. 37. Amino acid sequences of the variable regions of antibody clone 3 directed against human CD32B. Amino acid sequences are shown for the VH and VL regions. The boxed sequences represent the CDR sequences.

FIG. 38. Amino acid sequences of the variable regions of antibody clone 4 directed against human CD32B. Amino acid sequences are shown for the VH and VL regions. The boxed sequences represent the CDR sequences.

FIG. 39. Amino acid sequences of the variable regions of antibody clone 5 directed against human CD32B. Amino acid sequences are shown for the VH and VL regions. The boxed sequences represent the CDR sequences.

FIG. 40. Amino acid sequences of the variable regions of antibody clone 6 directed against human CD32B. Amino acid sequences are shown for the VH and VL regions. The boxed sequences represent the CDR sequences.

FIG. 41. Amino acid sequences of the variable regions of antibody clone 7 directed against human CD32B. Amino acid sequences are shown for the VH and VL regions. The boxed sequences represent the CDR sequences.

FIG. 42. Amino acid sequences of the variable regions of antibody clone 8 directed against human CD32B. Amino acid sequences are shown for the VH and VL regions. The boxed sequences represent the CDR sequences.

FIG. 43. Amino acid sequences of the variable regions of antibody clone 9 directed against human CD32B. Amino acid sequences are shown for the VH and VL regions. The boxed sequences represent the CDR sequences.

FIG. 44. Amino acid sequences of the variable regions of antibody clone 10 directed against human CD32B. Amino acid sequences are shown for the VH and VL regions. The boxed sequences represent the CDR sequences.

FIG. 45. Amino acid sequences of the variable regions of antibody clone 11 directed against human CD32B. Amino acid sequences are shown for the VH and VL regions. The boxed sequences represent the CDR sequences.

FIG. 46. Amino acid sequences of the variable regions of antibody clone 12 directed against human CD32B. Amino acid sequences are shown for the VH and VL regions. The boxed sequences represent the CDR sequences.

FIG. 47. Amino acid sequences of the variable regions of antibody clone 13 directed against human CD32B. Amino acid sequences are shown for the VH and VL regions. The boxed sequences represent the CDR sequences.

EXAMPLES

Example 1: CD20 Modulation in Primary CLL and Other NHL Samples

Figures 1C, 1D:
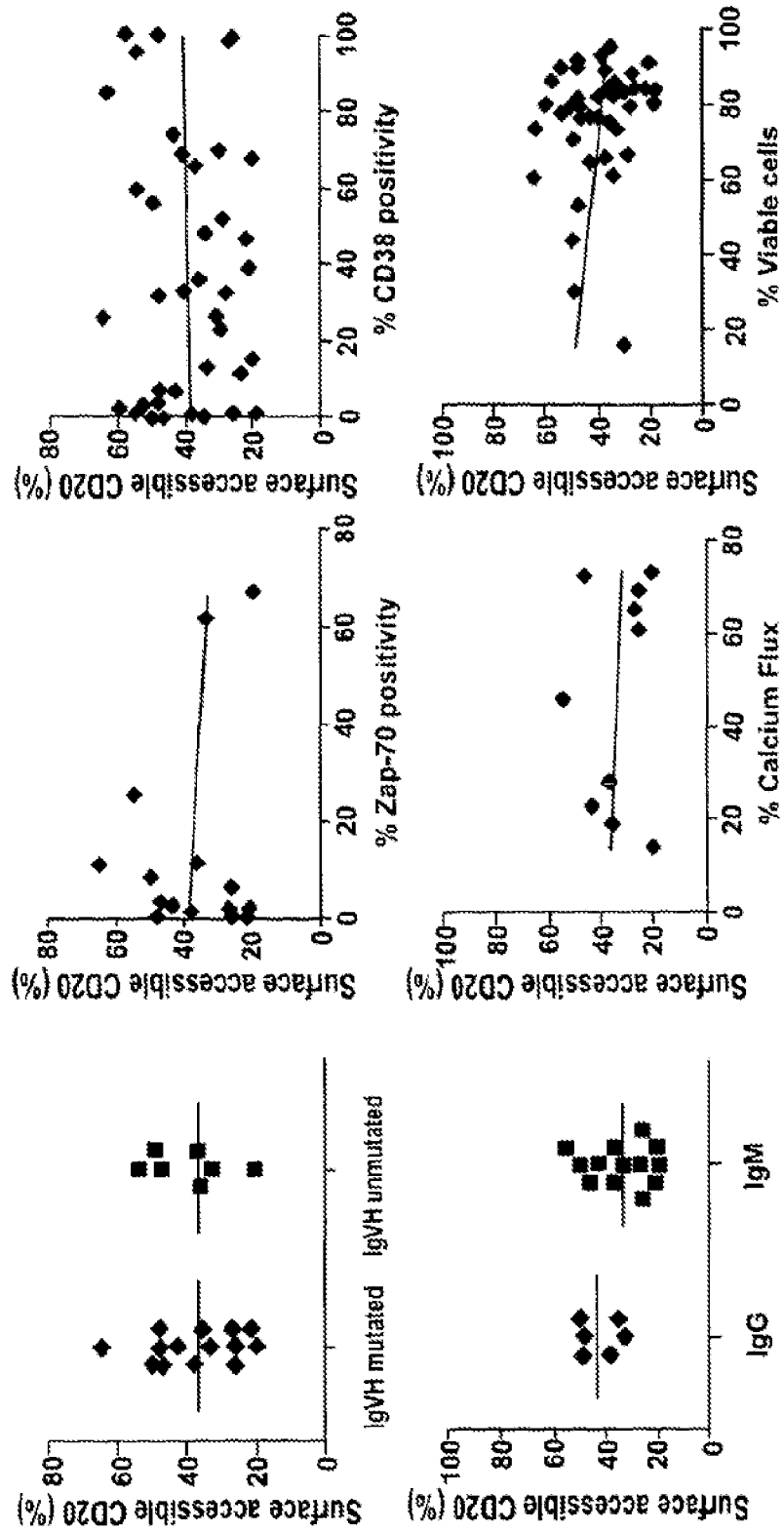
FIGS. 1C-1G. Lack of correlation between CD20 modulation and CLL phenotypic/prognostic markers.
Figure 1F:
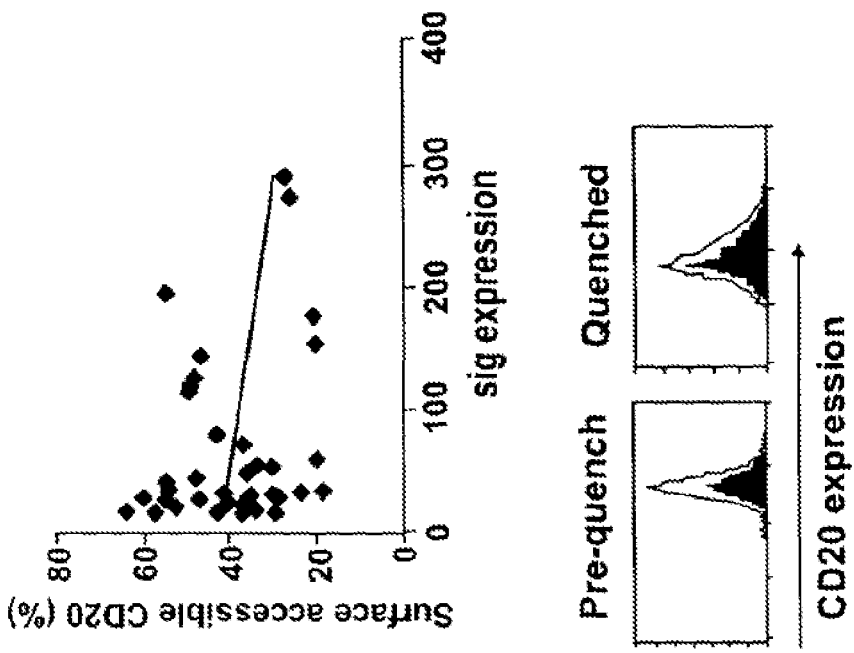

We previously observed heterogeneity in the rate and extent of rituximab modulation in a cohort of CLL samples (28). To validate and extend these findings, we have increased this cohort to a total of 48 CLL samples (FIG. 1A). As before, we compared the ability of rituximab and tositumomab (clinically-relevant prototypes of type I and II mAb, respectively) to reduce the amount of surface accessible CD20 over 2, 6 and 24 h (FIG. 1A and data not shown). In addition, we also tested in-house generated ofatumumab (ofatum; type I) which has recently been FDA approved for use in relapsed CLL, and a non-glycomodified version of GA101 ($GA101_{gly}$; type II) which is currently in clinical development for a range of NHL (19). In line with our previous observations, there was considerable heterogeneity between the samples but with the type I mAb resulting in significantly more modulation than type II mAb. At 6 h, modulation in the presence of rituximab was near maximal, with between 18 and 65% (median 37%) of the mAb remaining accessible in the quenching assay (FIG. 1A). Consistent with its type I nature, ofatumumab also resulted in a high degree of modulation (median 26% accessible at 6 h). In contrast, tositumomab and $GA101_{gly}$ showed far less modulation, with a median of 80% (range 61-89%) and 70% (range 57-81%) of bound mAb accessible at 6 h, respectively.

Within the CLL cohort, we examined a number of factors known to be important in the prognosis of CLL, including ZAP-70 expression (29, 30), CD38 positivity (31, 32) and IgVH gene mutation status (31, 33, 34). The results (FIG. 1C) showed no correlation with any of these disease markers.

We previously demonstrated that despite each NHL subtype having a distinct modulation pattern, they also displayed considerable CD20 modulation heterogeneity (28). To explore this further, we extended the number of primary samples analyzed to include 8 healthy volunteers, 7 SLL, 7 MCL, 11 FL and 7 DLBCL (FIG. 1B). The difference in the ability of type I and II mAb to induce modulation persisted across all histological sub-types. We also observed that CD20 on B cells from the healthy volunteers modulated rapidly in the presence of rituximab, and also more uniformly than with the malignant B cells, suggesting that factors associated with malignancy contribute to the observed heterogeneity. The rate of rituximab-induced modulation with SLL and MCL cells was similar to that with CLL (FIG. 1A), while for DLBCL and FL the rate was somewhat slower (p<0.0001 and 0.0027 respectively, when compared to CLL from FIG. 1A). However, in FL we did observe 2/11 patient samples modulated rituximab very rapidly, leaving barely detectable levels of mAb or CD20 after 6 h culture.

Example 2: Modulation of CD20 in B-NHL is an Fc-Dependent Process

Figures 2A, 2B:
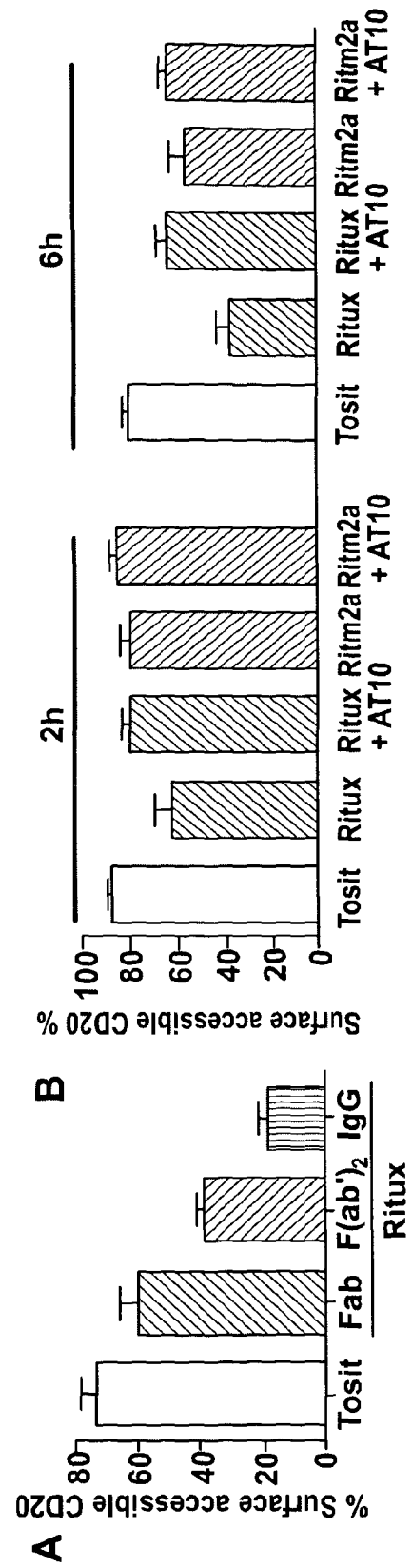
FIGS. 2A-2D. Modulation is an Fc-dependent process.

We and others have previously shown that the efficacy of anti-CD20 mAb in vivo is Fc-dependent (28). We hypothesized that modulation, even in the absence of effector cells, might also be Fc-dependent and tested this by repeating the internalization assay with Fab' and F(ab')$_2$ fragments of rituximab (FIG. 2A). Rituximab Fab' showed only a low level of modulation which could be explained either by the need for bivalent cross-linking of CD20 or by its low affinity univalent binding, as confirmed by cell binding assays (data not shown). In contrast, F(ab')$_2$ and IgG showed a similar binding profile (results not shown), but after 6 h culture the F(ab')$_2$ fragment had modulated significantly less (40% surface accessible CD20) than the intact IgG (20% surface accessible CD20). Since the assays were performed with highly enriched (>95% pure) B cells, the only FcR present in abundance would be the inhibitory FcγRIIb. In the presence of a blocking anti-FcγRII mAb, AT10, the modulation with rituximab was reduced, and comparable with rituximab F(ab')$_2$ fragments or Rit m2a, which binds to FcγRIIb with a lower affinity than human IgG1-bearing rituximab (FIG. 2B). As expected, co-incubation with AT10 resulted in very little influence on the modulation of Rit m2a.

Example 3: Expression of FcγRIIb on Normal B Cells and B-Cell Tumors

Figure 2C:
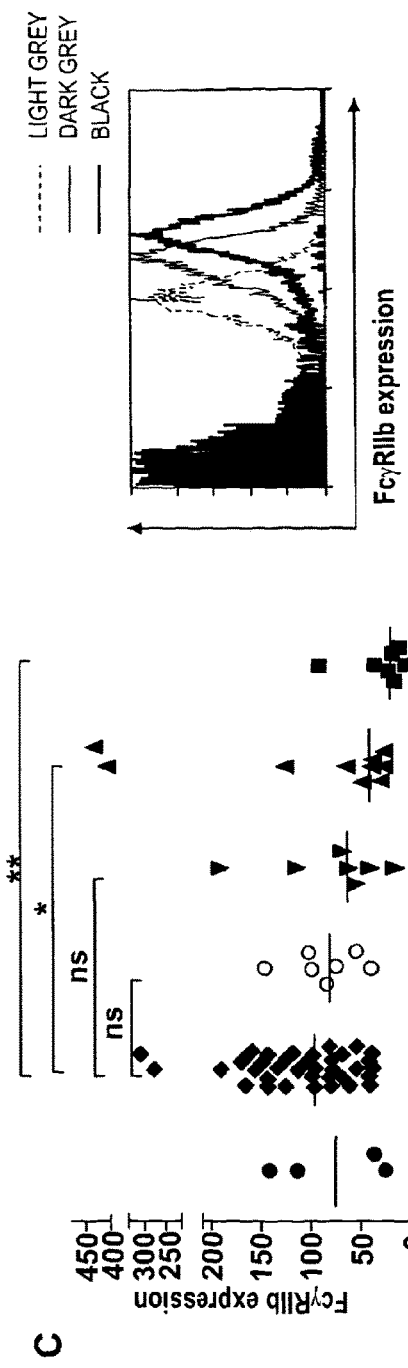

Given the possibility that FcγRIIb:Fc interactions could affect the rate of CD20 modulation, we examined the expression of FcγRIIb on normal B cells and our panel of primary B-cell tumors. As shown in FIG. 2C, there was marked heterogeneity of FcγRIIb expression within each group. Expression on CLL cells was relatively high, ranging from 20- to 300-fold over isotype control. DLBCL and the majority of FL displayed low FcγRIIb expression. Two FL cases displayed very high FcγRIIb expression, and strikingly, these were the same two cases that we had previously observed to modulate extremely rapidly. MCL and SLL expressed an intermediate albeit heterogeneous level of FcγRIIb (FIG. 2C), again consistent with previous findings (21).

Example 4: FcγRIIb Expression Regulates CD20 Modulation

Figure 2D:
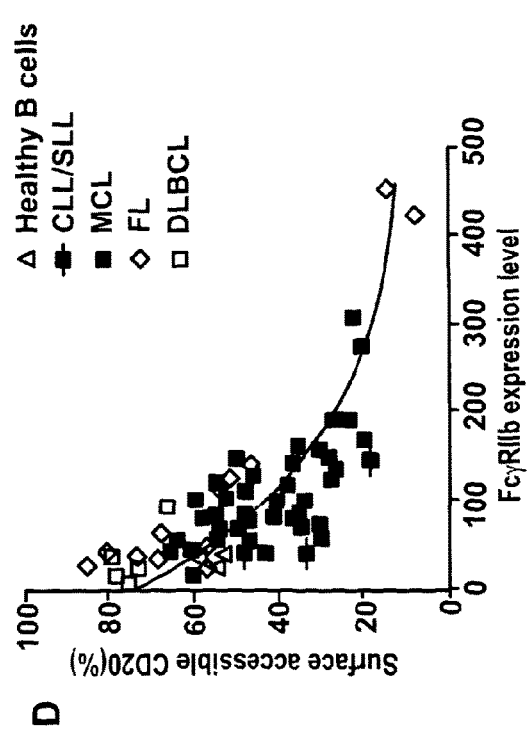

Altogether, these findings suggested that FcγRIIb expression may be a major determinant of CD20 modulation from B cell targets. To test this hypothesis, we compared the FcγRIIb expression and CD20 modulation rates of all of our available healthy B cell and primary NHL samples (FIG. 2D). Spearman's correlation analysis revealed a strong relationship between these parameters (Spearman r value −0.74, with 95% confidence intervals between −0.83 and −0.61 and p<0.0001). The data showed an inverse exponential curve with the majority of FL and DLBCL cases positioned at the top with CLL and MCL samples showing a widespread distribution. This graph also demonstrates that at low expression levels, small differences in FcγRIIb expression could be responsible for relatively large changes in CD20 modulation, thereby underlining the capacity of this receptor in regulating the clearance of anti-CD20:CD20 complexes from the cell surface.

To directly address the role of FcγRIIb in CD20 modulation, FcγRIIb$^{-ve}$ Ramos cells were transfected with an FcγRIIb-encoding plasmid. The resultant FcγRIIb$^{+ve}$ cells displayed variable FcγRIIb expression levels and were subsequently sorted into sub-clones expressing low, medium and high FcγRIIb. These cells, along with parental FcγRIIb$^-$ Ramos cells were then assessed in the internalization assay. In the presence of rituximab, CD20 modulation rates at 6 h correlated with FcγRIIb expression with increasing modulation in the order FcγRIIb$^{-ve}$>FcγRIIb$^{+ve}$ low>FcγRIIb$^{+ve}$ medium>FcγRIIb$^{+ve}$ high (FIG. 3A). Similarly, using B cells obtained from wild-type and FcγRII knockout (KO) mice expressing transgenic human CD20, modulation in FcγRIIb-/- mice cells was less than the wild-type counterparts (data not shown), although it should be noted that appreciable modulation was still observed in the absence of FcγRII, indicating that in this transgenic model factors additional to FcγRII are also involved in regulating CD20 modulation.

Figure 1E:
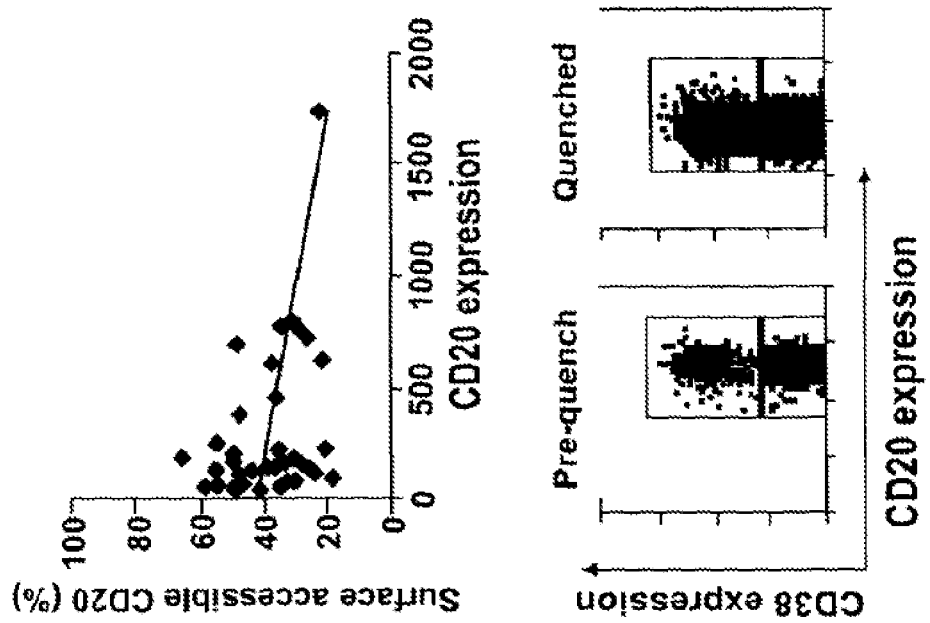
Figure 1G:
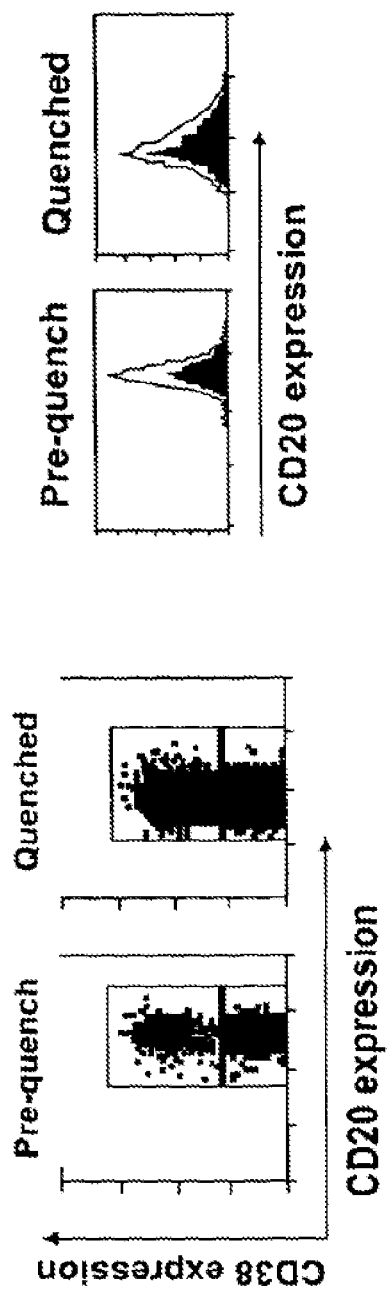

As FcγRIIb is a negative regulator of BCR activation on B cells (reviewed in (35)) and CD20 becomes physically associated with the BCR after engagement by CD20 mAb (36, 37), we hypothesized that BCR expression or signaling activity could influence modulation. Therefore, to exclude differences in BCR expression as the cause of these findings, BCR-deficient Ramos cells (Rx3) were transfected with FcγRIIb, and the modulation of CD20 compared with unmanipulated Ramos cells and mock Rx3 transfected cells (FIG. 3B). These data clearly indicate that Rx3 cells lacking BCR expression modulate more slowly than Ramos cells but that this defect can be overcome by expressing high levels of FcγRIIb (FcγRIIb$^{+ve}$ Rx3 cells). This dominant role of FcγRIIb over BCR in regulating CD20 modulation is supported by the following: 1) that we observe high levels of modulation in CLL cells which characteristically express low levels of BCR (38); and 2) we failed to show any correlation between surface immunoglobulin (sIg) expression on CLL cells and CD20 modulation (FIG. 1E).

Example 5: Modulation of CD20 and FcγRIIb is Preceded by Activation of FcγRIIb

To further probe the interaction between anti-CD20 mAb and FcγRIIb, we investigated antibody-mediated stimulation of FcγRIIb, as indicated by phosphorylation of tyrosine-293 in the intracellular ITIM motif. Raji cells were cultured with tositumomab or rituximab in the presence or absence of anti-FcγRIIb blocking mAb (AT10), before immunoblotting for phosphorylated FcγRIIb. Phosphorylated FcγRIIb was elevated in cells stimulated by rituximab, but not tositumomab, and was inhibited by the addition of AT10 (FIG. 4A). Similar results were observed with Daudi cells (data not shown).

Example 6: CD20 and FcγRIIb Cross-Linking Occurs Predominantly in a Cis Fashion

Rituximab could be co-ligated by CD20 and FcγRIIb on either the same (cis) or adjacent cells (trans). To investigate this, we co-cultured PKH26-labeled FcγRIIb$^-$ Ramos cells with high FcγRIIb-expressing Ramos transfectants (FIG. 4B), and then compared the level of modulation in each cell type, with both cell types cultured alone as a control. As shown previously, when cultured alone the FcγRIIb$^{+ve}$ cells showed greater modulation than cells lacking FcγRIIb (FIG. 4B). In the co-culture, the level of modulation in the FcγRIIb$^{-ve}$ was slightly increased, but did not reach the level seen in the FcγRIIb$^{+ve}$ cells. This result suggests that while a trans interaction may occur, modulation of CD20 mAb by FcγRIIb is predominantly driven in a cis fashion.

To demonstrate that this finding was not specific to the Ramos cell-line, we co-cultured a CLL sample expressing low FcγRIIb (distinguished by PKH26 labeling) with cells from three different CLL cases expressing high levels of FcγRIIb (FIG. 4C). As seen in the previous assay with Ramos cells, in the mixed populations the modulation in the low FcγRIIb B-cells did not approach that seen in the high FcγRIIb population, again suggesting that modulation of CD20 mAb by FcγRIIb is predominantly driven in a cis fashion. However, it is interesting to note that co-culture with the fastest modulating CLL cells resulted in the greatest increase in the modulation of the low FcγRIIb-expressing CLL, but the increase was only modest (approximately 18%; data not shown).

Figure 4E:
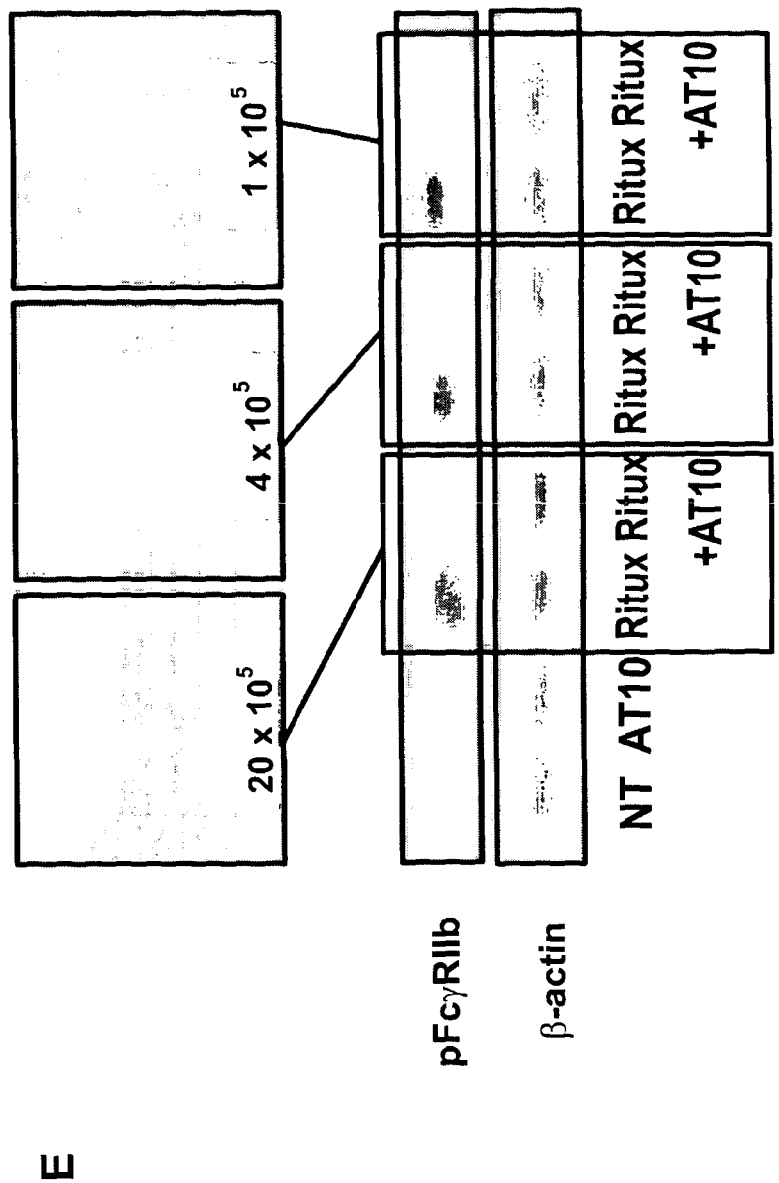

In an additional experiment of this type, CLL cells were cultured at decreasing concentrations to reduce the potential for cell:cell interaction, with the result of a weak trend of less modulation with decreasing cell concentration (FIG. 4D). The same experiment was repeated with different concentrations of Raji cells and again little change in degree or extent of modulation was seen (data not shown). Importantly, bright field microscopy images taken during this experiment demonstrate that the likelihood of inter-cellular (trans) interaction was much less at 1×10$^5$ compared with 2×10$^6$ cells/ml. Furthermore, we observed that there was no marked difference in the levels of phosphorylated FcγRIIb at the different cell densities (FIG. 4E). Altogether, these data indicate that FcγRIIb mediates its effects on CD20 mAb modulation predominantly through events on the same cell with only a small contribution from neighboring FcγRIIb-expressing cells.

Example 7: FcγRIIb is Endocytosed with CD20 into Lysosomes

Figures 5A, 5C:
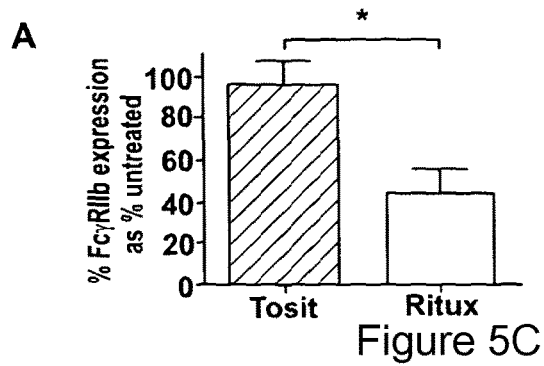
FIGS. 5A-5E Rituximab, CD20 and FcγRIIb internalize together into lysosomes.

To ascertain the fate of FcγRIIb after engagement of rituximab at the cell surface we monitored its expression and location by flow cytometry and confocal microscopy. Using flow cytometry we assessed the surface expression of FcγRIIb on B cells from six different cases of CLL and found that it declined within 2 h of incubation with rituximab but not tositumomab (FIG. 5A). These findings suggest that FcγRIIb might be internalized along with CD20 and rituximab (but not tositumomab) as part of a tri-partite complex.

Figure 5B:
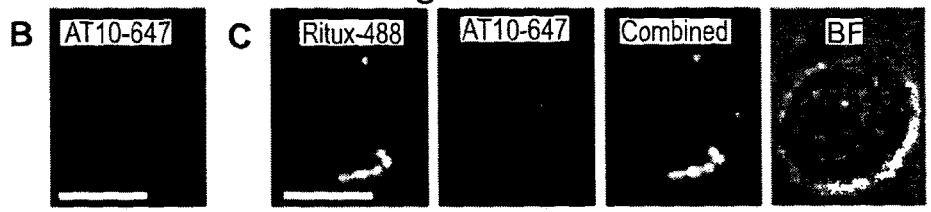
Figure 5D:
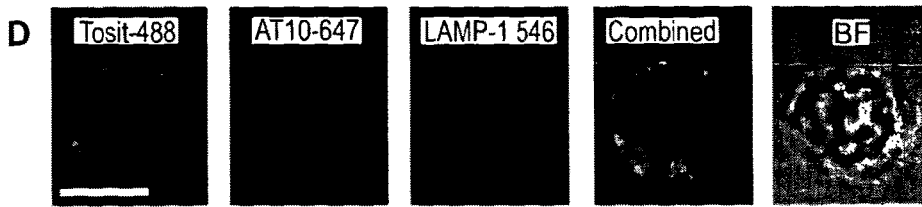
Figure 5E:
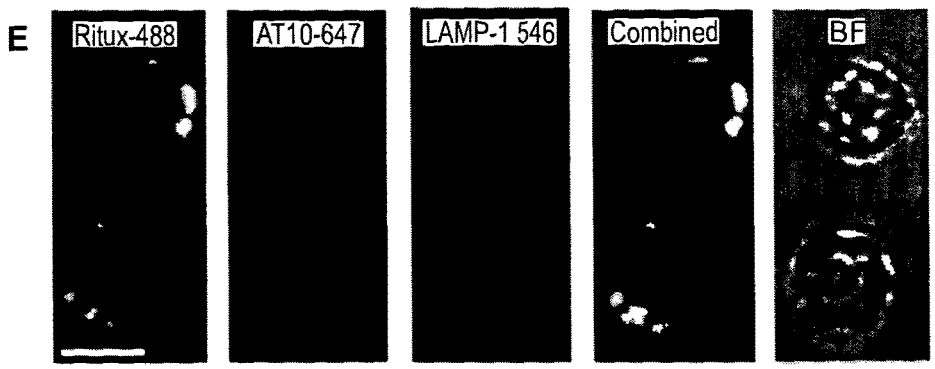

We and others have previously reported endocytosis of rituximab resulting in its trafficking to early endosomes and subsequent degradation in lysosomes (9, 28). To address whether the same process occurred with FcγRIIb as part of an anti-CD20:CD20:FcγRIIb complex in CLL cells we cultured them with either Tosit-488 or Ritux-488 before fixation and staining for FcγRIIb (using Alexa 647-labeled F(ab')$_2$ from AT10) and the lysosomal marker LAMP-1. Prior to stimulation with mAb, FcγRIIb staining was diffuse and non-localized in the plasma membrane (FIG. 5B). Following incubation with anti-CD20 mAb for 30 min, we observed a distinct difference in staining between Ritux-488 and Tosit-488, whereby Tosit-488 remained exclusively on the surface and Ritux-488 demonstrated intracellular punctate staining, consistent with our previous observations (FIG. 5C, data not shown and (28)). After 6 h stimulation, Tosit-488 remained evenly distributed across the cell surface, whilst AT10-647 was unchanged from its baseline appearance at 30 min, and there was no co-localization with LAMP-1 (FIG. 5D). In contrast, over the same time course, Ritux-488 showed a distinct punctate pattern with the majority of cells (58%) demonstrating co-localization between AT10-647 and Ritux-488 (FIG. 5E). Co-localization of Ritux-488 with both LAMP1 and AT10-647 was also observed in 33% of cells. Presumably, the lower degree of co-localization observed between all three stains, reflects the fact that Ritux-488 and FcγRIIb internalize together and likely occupy other intracellular compartments prior to their appearance in lysosomes.

Example 8: FcγRIIb Inhibits Type I Anti-CD20 mAb In Vivo

Figure 6:
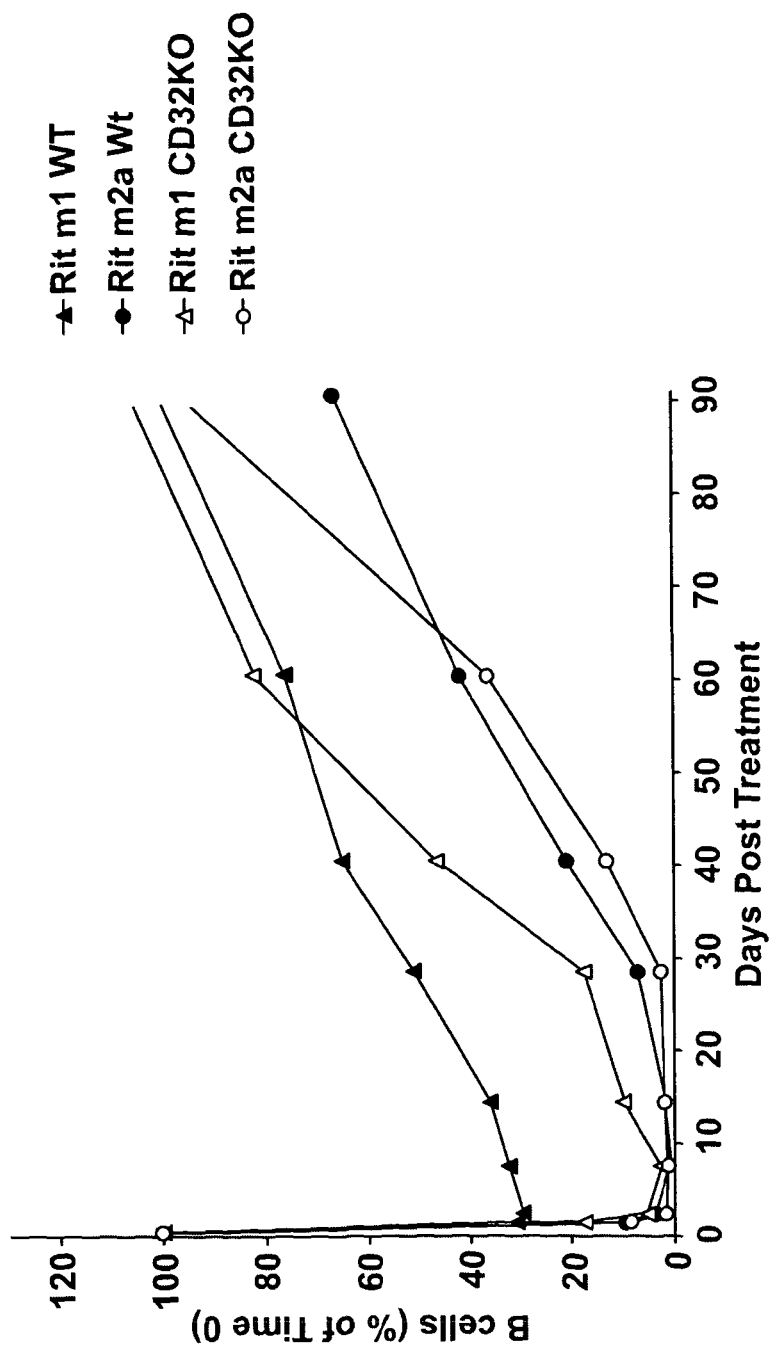
FIG. 6. Lack of inhibitory receptor augments the depleting ability of anti-CD20 mAb. hCD20 Tg mice (WT) or hCD20 Tg mice lacking CD32 (CD32KO) were treated with rituximab variants harboring mouse IgG1 (m1) or mouse IgG2a (m2a); 250 mg iv and then b cell depletion monitored by low cytometry for 90 days through serial bleeding of the mice and staining with B220 and CD19 mAb.

To address whether FcγRIIb might inhibit the efficacy of Type I anti-CD20 mAb in vivo, we performed B cell depletion experiments in hCD20 Tg wild-type mice and also in hCD20 Tg mice lacking FcγRIIb (CD32 KO). In these experiments the mice were treated with rituximab variants (250 μg, iv) harboring mouse IgG1 (m1) or mouse IgG2a (m2a) and then B cell depletion monitored by flow cytometry for 90 days through serial bleeding of the mice and staining with B220 and CD19 mAb (FIG. 6). These variants either bind strongly (m1) or weakly (m2a) to CD32b. The data clearly show that when the m1 isotype was used, depletion is sub-optimal (compared to the m2a) and that loss of CD32 results in a substantial improvement in depletion efficacy. In contrast, the m2a is largely similar in the presence or absence of CD32.

Figure 7:
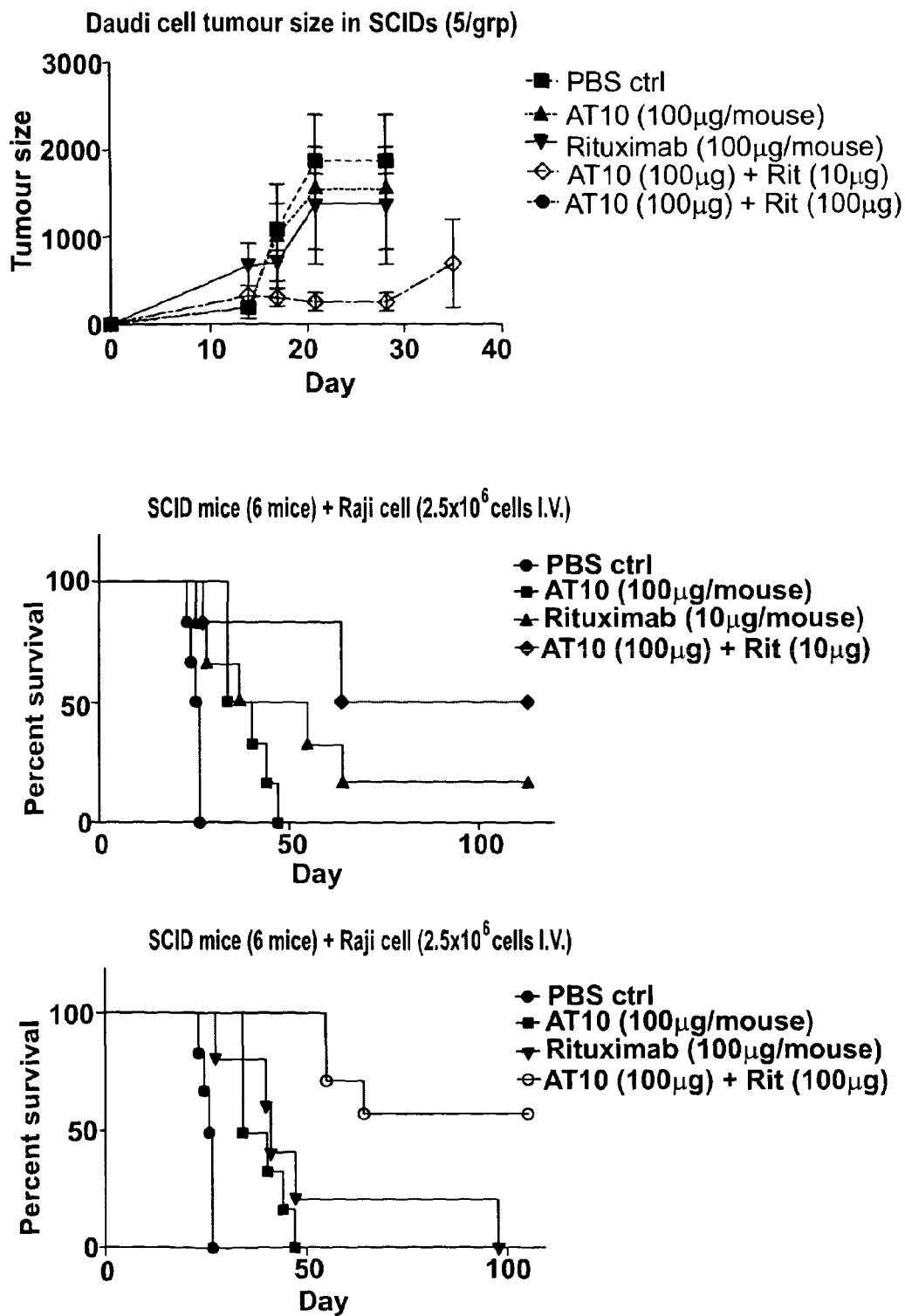
FIG. 7. Blocking the inhibitory receptor CD32b (FcγRIIb) augments the efficacy of anti-CD20 mAb in a human xenograft system. CD20 positive human tumour cells (Daudi or Raji) were inoculated into SCID mice and then treated with either rituximab, AT10 or both and survival of the mice or tumour growth monitored. Doses of mAb used are shown in the figure legends. In A) Daudi cells were inoculated subcutaneously and the tumour monitored by caliper measurements every 305 days. In B) and C) Raji cells were inoculated intravenously.

Example 9: FcγRIIb Enhances and Augments the Activity of Anti-CD20 mAb Against Human Tumours In Vivo To examine the effect of CD32 on human tumour cells and the potential of augmenting current therapeutic mAbs, such as rituximab, we employed a xenograft system. In this system, only the human tumour cells express hCD32 and so any therapeutic effects derive from effects on the tumour cell, most likely by blocking modulation, not through any effects on the host effector cells. In these experiments CD20 positive CD32 positive human tumour cells (Daudi or Raji) were inoculated into SCID mice and then treated with either rituximab, AT10 or both and survival of the mice or tumour growth monitored (FIG. 7). Doses of mAb used are shown in the figure legends. In A) Daudi cells were inoculated subcutaneously and the tumour monitored by caliper measurements every 3-5 days. In B and C Raji tumour cells were injected intravenously and animals monitored for survival. In both models, AT10 was shown to enhance and augment the activity of rituximab, demonstrating the potential of this combination in vivo.

Figure 11:
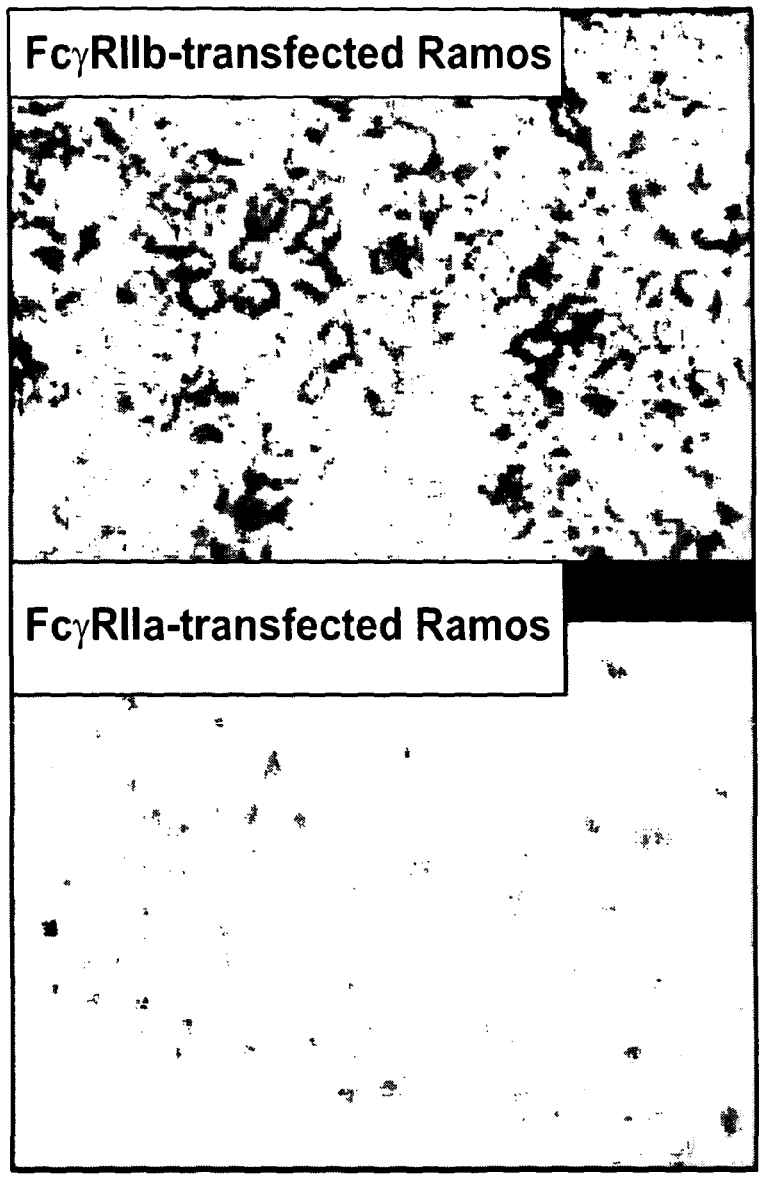
FIG. 11. Confirmation of specificity of anti-FcγRIIb mAb used in immunohistochemistry FcγRIIa and FcγRIIb transfected Ramos cells were cytospun and paraffin-embedded. Immunohistochemistry using mAb to human FcγRIIb demonstrated strong membrane staining in FcγRIIb-transfected Ramos but no staining in FcγRIIa-transfected cells.

Example 10: FcγRIIb Levels Predict Clinical Outcome in Rituximab-Treated MCL Patients As proof-of-concept of our in vitro findings, we retrospectively examined the FcγRIIb expression of a cohort of MCL that had received rituximab. Diagnostic paraffin-embedded tissue was stained by immunohistochemistry using an FcγRIIb-specific mAb (FIG. 11). Strong membrane staining was seen in FcγRIIb+ve but not FcγRIIb-ve lymphoma samples. These results correlated with FcγRIIb expression of corresponding DMSO-frozen samples, obtained by flow cytometry. The FcγRIIb staining shown in FIGS. 10A and 10B by IHC correlated with the FcγRIIb expression shown by flow cytometry as shown in FIG. 2D (with the value determined by flow cytometry in 2D shown as the number inset in FIGS. 10A and 10B). Despite studying only a small cohort of 16 MCL patients, patients with FcγRIIb-ve lymphoma had significantly better median progression-free survival than those with FcγRIIb+ve cells (median 852 and 189 days, respectively). FIG. 10C shows the differences in survival in the FcγRIIb+ and -subsets. The groups were comparable in terms of clinical features (MCL international prognostic index, data not shown), but there was heterogeneity in chemotherapy types used. In order to address this, we examined the results in those patients treated with either single-agent rituximab or fludarabine, cyclophosphamide and rituximab (FCR) for initial therapy, and similar results were observed. FIG. 10D shows the differences in survival in the FcγRIIb+ and − subsets after the patient cohorts were further controlled as discussed.

The Rationale for the experiments in examples 10 and 11 is as follows. If cells express high levels of CD32b (FcγRIIb), they will internalise rituximab more quickly (shown as reduced % surface accessible CD20). If there is less rituximab at the cell surface, then there will be less Fc-dependent effector activity (such as phagocytosis or ADCC) and therefore less tumour cell killing and hence less extensive therapeutic results. Therefore, we checked the FcγRIIb expression in a cohort of patients treated with MCL and determined whether they were high or low expressors of CD32b. Clinical data was already available for this cohort and so the clinical results were then stratified according to whether they were high or low FcγRIIb-expressing tumours. The hypothesis was that tumours expressing low levels of FcγRIIb would be treated successfully with rituximab and those expressing high levels of FcγRIIb would do less well. This is exactly what was shown in the clinical data. FIG. 11 shows the specificity of the mAb used for the FcγRIIb staining. It stains only cells expressing FcγRIIb NOT the closely related FcγRIIa.

After measuring FcγRIIb levels by IHC (FIG. 10B) and separating MCL samples into positive and negative for FcγRIIb, we saw a clear clinical difference in response following rituximab-based therapy (FIGS. 10C and 10D).

Example 11—Selection of Anti-CD32b Monoclonal Antibodies

The amino acid sequences of the variable regions (VH and VL), together with the CDR regions of the 14 antibody clones are shown in FIGS. 37-50. In each case, the constant (CH and CL) regions are the same. The constant regions are shown in FIG. 36.

Selections against CD32B (FcγRIIb) were performed using the n-CoDeR® scFv phage display library. Human CD32A was used as non-target. The extra cellular domains of CD32A and CD32B fused to mIgG$_3$-Fc were produced in HEK293E and purified on protein A. Three consecutive protein selections were performed. Non-target was used as competitor in all selections. Resulting phages were converted to scFv/Fab producing format and transformed into *E. coli* Top10 bacteria for screening of individual clones. Screening determined the specificity for human CD32B and CD32A and was analyzed using coated proteins in ELISA as well as through transfected CHO cells in FMAT. For determination of IC inhibition properties, the IgGs were left to bind CD32B transfected CHO cells followed by addition of an IC in the form of IgG1 coated bovine serum albumin. Bound IC was then detected and inhibiting properties of the IgGs could be evaluated.

Example 12—Ability of Anti-CD32b mAb to Block Modulation of Rituximab

Figure 12:
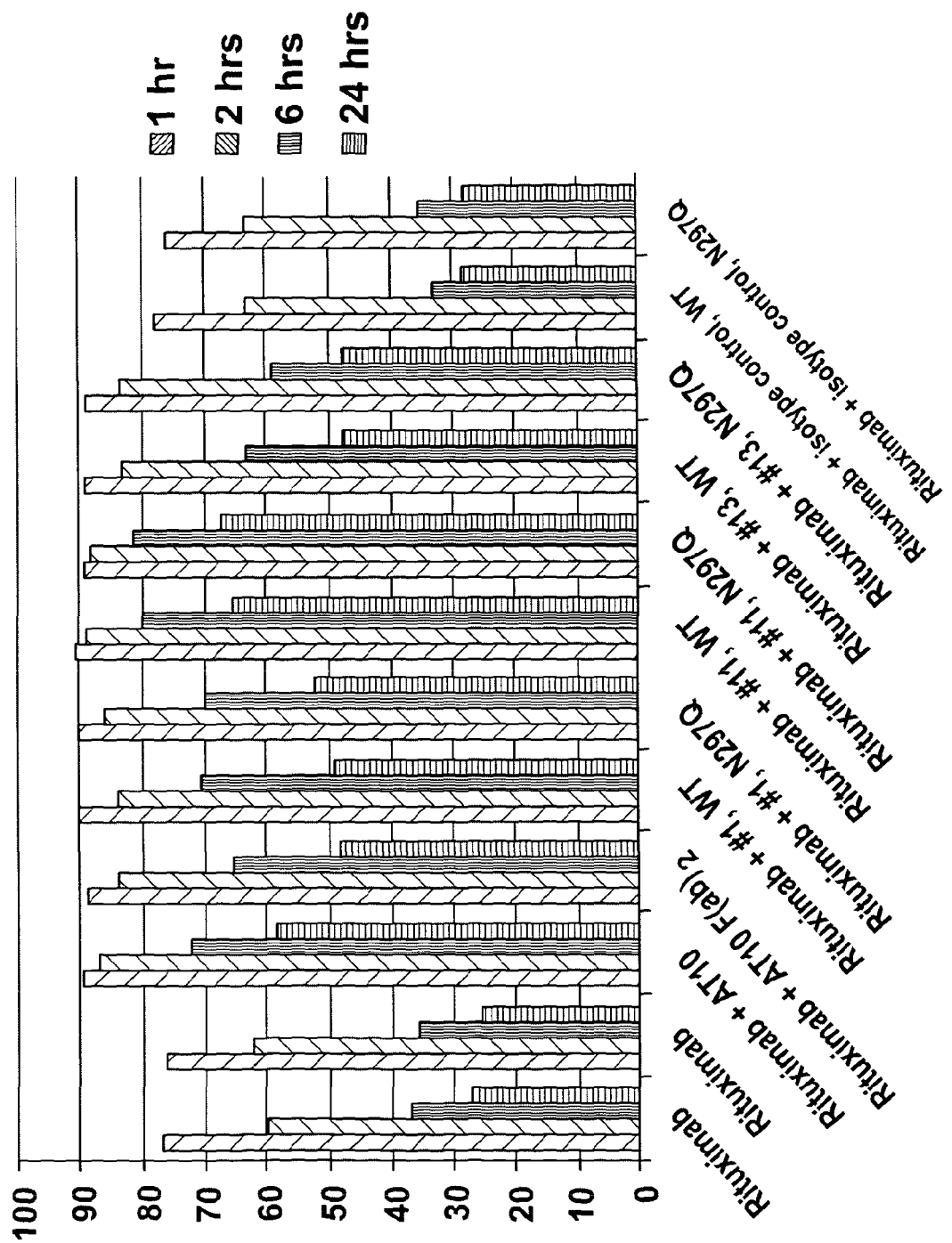
FIG. 12. CD32B specific clones inhibit Rituximab internalization.

Rituximab-alexa 488 was added to Ramos cells transfected with CD32B in the presence or absence of different CD32b blocking mAb (WT or 297Q mutants) and modulation assessed after 1, 2, 6 and 24 h. As a control for the blocking ability of CD32 mAb we also included the dual CD32a and b specific mAb, AT10 (IgG and Fab2 fragments (Fab)), alongside a negative control, isotype matched irrelevant mAb (iso wt or nq). The data in FIG. 12 clearly indicate that all 3 nCoder mAb (C1, C3 and C11) are able to block the modulation of rituximab in either the wt or 297q format.

FIG. 13 shows the ability of anti-CD32b mAb to block modulation of rituximab using all 13 mAb. In addition, control CD32 negative Ramos cells were included to allow estimation of the maximal effect of the CD32 blocking mAb. The data in FIG. 12 clearly indicate that all the nCoder mAb were able to block the modulation of rituximab.

The previous set of experiments had demonstrated that FcγRIIb regulates the internalisation of rituximab. Therefore these experiments sought to examine whether blocking FcγRIIb with anti-FcγRIIb mAb would reduce the amount that rituximab is internalised.

Example 13. Correlation Between Affinity and the Ability of Anti-CD32b Blocking mAb to Prevent Phosphorylation of CD32b after Rituximab Binding and to Prevent Modulation of Rituximab The relative affinity of the mAb was determined by a dose titration experiment measuring mAb binding to CD32B transfected CHO cells. Briefly, CD32B transfected adherent CHO K1 cell were seeded into FMAT plates. IgG were titrated in 1:2 dilutions from 30 nM to approximately 0.015 nM and left to bind for 1 h at room temperature. After washing bound IgG were detected with anti-human-IgG-APC. Finally, the plates were washed and read in the FMAT (Applied Biosystems). This gives an EC50 value for mAb binding to target expressing cells and can be translated to a relative affinity. The relative affinity was then correlated with the ability of ant-CD32b blocking mAb to prevent phosphorylation of CD32b after rituximab binding. This was determined by stimulating cells with rituximab in the presence or absence of anti-CD32b mAb and then performing western blotting for phospho-CD32b. The CD32b mAb were then ranked according to their ability to block the CD32 phosphorylation with 1 being the most effective. FIG. 14A shows that there was evidently a close correlation between the affinity of the mAb and the ability to block CD32b phosphorylation. FIG. 14B shows there was evidently a strong correlation between the affinity of the mAb and the ability to block rituximab modulation. This data confirms the central role of CD32B in accelerating the modulation of rituximab from the target cell surface.

The rationale was that the higher affinity of mAb would better block FcγRIIb. Subsequently, the better the mAb blocked FcγRIIb the better it would block modulation/internalisation of rituximab. This is exactly what was shown in FIGS. 14A-14B. The higher the affinity, the better it blocked FcγRIIb activation (measured by the amount of phospho-FcγRIIb staining by western blotting) induced by rituximab binding and also the better they blocked modulation.

Example 14. Dose Dependent Binding to hCD32B Transfected Cells and Dose Dependent Binding and Inhibition of Immune Complex to hCD32B Transfected Cells Cells were seeded into FMAT plates. Immune complexes were prepared by coating FITC to BSA and thereafter mix this with a 10:1 molar ratio with a FITC specific hIgG1 antibody. FIGS. 15-27 show the dose dependent binding to hCD32B transfected cells and dose dependent binding and inhibition of immune complex to hCD32B transfected cells mediated by clones 1-13, respectively. Circles show dose dependent binding to hCD32A transfected CHO K1 cells and black diamonds show dependent binding to hCD32B transfected CHO K1 cells. Crosses show dose dependent inhibition of immune complex to hCD32B transfected CHO K1 cells.

The experiments are designed to 1) determine specificity of the mAb's. CD32B and CD32A are very closely related molecules. However, while CD32B transmits an inhibitory signal, CD32A transmits a positive, hence it is essential that the antibody only binds CD32B for the desired effect. 2) Furthermore, to effectively block a signal through CD32B, the antibody does not only have to bind CD32B, but also to block binding of it's natural ligand, an immune complex (IC). Hence the figure shows binding to CD32A, CD32B and inhibition of IC binding. The figures demonstrate that all mAb's are specific for CD32B and does not bind CD32A and that they all inhibit IC binding.

Example 15. Cell Specificity of the Anti-CD32B Antibodies

PBMCs isolated from peripheral blood was prepared using Ficoll density gradient. Cells were stained with cell specific markers and evaluated for binding of the CD32B specific antibodies. As shown in FIG. 28, only B cells (CD19+ cells) stained positive with clone 1-13.

In resting PBMC's, CD32B is only expressed on B cells while the closely related CD32A is expressed on monocytes and neutrophils. The previous figures show specificity on transfected CHO cells. FIG. 28 shows that the antibodies also binds B cells expressing CD32B in it's truly native form on B cells while they do not stain CD32A expressing neutrophils or monocytes. Hence this figure is a demonstration of antibody specificity when antigen is expressed in normal non-transfected PBMC's.

Example 16. Dose Dependent Staining of B Cells by Anti-FcγRIIb mAb Clone 1-13

PBMCs isolated from peripheral blood was prepared using Ficoll density gradient. Cells were stained with CD19 and thereafter with 10, 1 or 0.1 mg/ml CD32B specific antibodies as indicated. FIG. 29 shows how the cell staining of B cells by each clone is dose dependent.

In FIG. 29, B cells (known to express CD32B) have been gated out using a CD19 specific mAb. This gate is called M1. When the concentration of CD32B mAb is decreased, the number of B cells stained drops from nearly 100% down to much lower values, showing a specific and dose dependent staining of B cells, as expected from a CD32B specific mAb.

This is again a demonstration of the antibodies specificity. As already mentioned, CD32A and B are extremely closely related and obtaining specific antibodies is not trivial. Any specific antibody should show dose-dependent binding and this is what is demonstrated in FIG. 29, that lowering the antibody dose decreases the amount of B cells stained from the nearly 100% as observed in the highest dose. Hence this figure is a second demonstration of antibody specificity when antigen is expressed in normal non-transfected B cells.

Example 17. Capacity of Each mAb to Inhibit Fc-Mediated CD32B Phosphorylation Raji cells (CD32B positive) where treated with Rituximab, which caused phosphorylation of CD32B. This was done in absence or presence of CD32B specific mAb's 1-13 and FIG. 30 demonstrates each mAb's capacity to inhibit Fc mediated CD32B phosphorylation.

The hypothesis behind examples 17 and 18 is that the Fc region of rituximab binds FcγRIIb and that this causes activation of FcγRIIb. This is measured by phosphorylation of the ITIM region of the FcγRIIb. Blocking this interaction with anti-FcγRIIb mAb should block phosphorylation (FIG. 30) and modulation (FIGS. 31 and 32). The wt FcγRIIb IgG1 has the capacity to also bind the FcγRIIb through its Fc region and so we examined whether the N297Q Mutant (which has an Fc that does not bind FcγRIIb) also had similar activity. It had identical activity.

Example 18. The Effect of CD32b on the Rate of Modulation of Type I Anti-CD20 mAbs The ability of CD32b to precipitate the internalisation of other Type I anti-CD20 mAb is shown in FIG. 31. Alexa-488 labelled versions of each mAb were incubated with pCDNA3-transfected Ramos or CD32B-transfected Ramos cells for 1 or 6 hr and the extent of modulation determined as before. mAb used were rituximab (RTX), in-house produced ofatumumab (OFA) and tositumumomab (Tos). The data clearly show that the rate of internalisation of OFA is similar to that of RTX and is accelerated by the presence of CD32b.

These modulation effects were observed with rituximab (a Type I anti-CD20) but were less evident with tositumomab (a type II anti-CD20 mAb) Therefore we wanted to address whether this extended to other anti-CD20 mAb and so tested ofatumumab, another clinically relevant Type I mAb (Teeling, 2004 (52) Ofatumumab, like rituximab was rapidly internalised as expected.

Example 19. Anti-CD19 mAb Also Internalize from the Cell Surface of Malignant Human B-Cells in a Manner which is Partially Dependent Upon CD32B Ramos huCD32b transfectants. Internalisation with other surface antigens can also be effected by CD32b expression. The modulation assay was performed as before with different mAb in the presence (+) or absence (−) of CD32 BLOCKING with AT10. Ramos CD32B transfectants were used in this 6 h assay. $*p<0.05$. f3.3=MHC Class II; RFBP=CD19; RTX=rituximab. FIG. 32 clearly shows a significant reduction in surface modulation for RTX and RFB9 mAb and less for F3.3 after incubation with CD32 blocking. These data indicate that target antigens such as CD19 can also internalize from the cell surface of malignant human B-cells in a manner which is partially dependent upon CD32B and can be blocked by anti-CD32b mAb.

We wanted to determine whether target antigens other than CD20 are also affected by FcγRIIb expression. Therefore we examined mAb directed to other target antigens (CD19 and MHCII) and whether mAb blocking FcγRIIb would reduce their internalisation. The data show that the modulation of CD19 mAb is also reduced by blocking FcγRIIb.

Example 20. Internalisation with Other Surface Antigens can Also be Effected by CD32b Expression Ramos cells have no CD32b and so demonstrate the level of internalisation in the absence of CD32B. If the antigen is able to be internalised by CD32b then expressing it (on the Ramos-CD32B cells) will increase the level of internalisation.

Alexa-488 labelled versions of each mAb were incubated with pCDNA3-transfected Ramos or CD32B-transfected Ramos cells for 24 h and the extent of modulation determined as before. $*=p<0.05$. FIG. 33 shows that internalisation with other antigens is also effected by CD32b expression.

Materials and Methods
Cells

Human cell-lines (Daudi, Raji, Ramos) were obtained from ECACC and were maintained in RPMI (Invitrogen, UK) supplemented with 10% fetal calf serum (FCS) (Lonza, UK) and glutamine and pyruvate (both Invitrogen) and cultured at 37° C., 5% $CO_2$. Rx3 Ramos cells lacking BCR expression were generated previously (36). Ramos FcγRIIb transfectants and control cells transfected with empty vectors (FcγRIIb negative) were previously described (36), and were maintained in supplemented RPMI as above, with the addition of Geneticin (Invitrogen, UK). Rx3 cells transfected with FcγRIIb and empty vectors were produced and maintained in the same way. FcγRIIb surface expression was determined by flow cytometry using PE-labeled AT10 (described below). Populations of Ramos FcγRIIb transfectants expressing low, medium or high levels of FcγRIIb were sorted using a FACS Aria flow cytometer (BD Biosciences, USA).

Blood Donors

Normal human B cells were obtained from healthy volunteers with informed consent. Peripheral blood was taken in either $K_2E$ or LiH, lymphocytes separated using Lymphoprep (Axis-Shield, UK) as per the manufacturer's protocol, and B cells isolated by negative selection with the Human B-cell Isolation Kit II (Miltenyi Biotec, Germany).

Clinical Samples

CLL/SLL, FL, DLBCL and MCL samples were obtained with informed consent in accordance with the Declaration of Helsinki. Blood samples were collected in $K_2E$ or LiH with Lymphoprep and solid tissue was disaggregated through a sterile strainer and centrifuged. Cells were cryopreserved in RPMI supplemented with 50% human AB serum and 10% DMSO and stored in University of Southampton's Cancer Sciences Division Tumor Bank under Human Tissue Authority licensing. Ethical approval for the use of clinical samples was obtained by the Southampton University Hospitals NHS Trust from the Southampton and South West Hampshire Research Ethics Committee. For CLL cells, mutation status of IgVH genes (33) and CD38 positivity (44) was determined as detailed previously. Briefly, for IgVH analysis, a VH leader primer mix and a Cµ100 primer were used to amplify heavy-chain genes from cDNA. All nucleotide sequences were aligned to the V-base directory, and mutational status was determined using a 98% cutoff. For CD38 analysis, anti-CD38 PE (clone HB7; BD Biosciences) was used. Determination of ZAP-70 status was carried out as described by Crespo et al. (30). Surface Ig expression of CLL cells was determined by flow cytometry as described previously (45, 46).

Viability Assay

Cells were assessed for viability by flow cytometry following staining with FITC-labeled annexin V and PI as detailed previously (25).

Antibodies and Reagents

Rituximab was gifted by Oncology Pharmacy, Southampton General Hospital. Rit m2a (rituximab with mouse IgG2a Fc region), and WR17 (anti-CD37), all mouse IgG2a, were produced as described previously (18). Anti-FcγRII mAb (AT10) was produced in-house and has been described previously (47). Tositumomab was gifted by Prof Tim Illidge (Manchester, United Kingdom). Ofatumumab and GA101$_{gly}$ (glycosylated GA101 with unmodified Fc region) were produced in-house from patent published sequences. NB: These mAb were produced in CHO or 293F cells and so may differ (for example in their carbohydrate structures) from the mAb produced for clinical use. Alexa-488 and anti-Alexa 488 reagents were purchased from Invitrogen. Production of F(ab')$_2$ fragments has previously been described (48). Fab' fragments were generated by incubation with 20 mM 2-mercaptoethanol at 25° C., for 30 min, followed by addition of excess iodoacetamide. Western blotting antibodies used were anti-actin (AC74, Sigma, UK) and anti-phospho-FcγRIIb (Cell Signaling Technology, UK).

Flow Cytometry

Fluorochrome-labeled mAb were obtained from BD Biosciences or made in-house. mAb were conjugated with Alexa 488 (Invitrogen) as per the manufacturer's protocol. Flow cytometry has been described previously (49). Samples were assessed on either a FACScan or FACSCalibur and data analyzed with CellQuest Pro (all BD Biosciences) or FCS Express (DeNovo Software, USA). B cells were identified with APC-labeled anti-human CD19 (in-house) and FcγRIIb expression determined using PE-labeled AT10 (in-house). To control for inter-experimental variation, FcγRIIb expression was represented as the ratio of FcγRIIb: isotype control Geo mean fluorescence intensity (MFI).

Internalization Assay

The internalization assay was performed as detailed previously (28). Briefly, 2-4×10$^5$ cells per well were incubated with Alexa-488 labeled mAb at a final concentration of 5 µg/ml. Samples were harvested after 1, 2, 6 and/or 24 h, washed twice, resuspended and incubated at 4° C. for 30 min with APC-labeled anti-CD19, with or without the quenching antibody, anti-Alexa-488 (Invitrogen). Samples were then washed once and analyzed on a flow cytometer.

To investigate the interaction of the Fc region of cell-bound anti-CD20 mAb with FcγRIIb on adjacent cells, Ramos cells, which are FcγRIIb$^{-ve}$, were labeled with PKH26 (Sigma Aldrich) as per the manufacturer's instructions. The PKH26-labeled cells were then co-cultured with equal numbers (2.5×10$^5$ cells) of Ramos cells transfected with FcγRIIb. Both cell types were cultured alone as controls. The internalization assay was then performed as described above, and the modulation compared on the PKH26-labeled and -unlabeled populations. Further variations of this co-culture assay are described in figure legends.

Western Blotting

The protocol has been described previously (36). Briefly, −2×10$^6$ cells per well were incubated with mAb (5-10 µg/ml). Samples were then separated by SDS PAGE and proteins transferred immediately onto PVDF membrane. Membranes were blocked with 5% w/v non-fat dried milk, incubated with the appropriately diluted primary antibodies, washed and then incubated with horseradish peroxidase-conjugated anti-rabbit or anti-mouse IgG (Sigma Aldrich) and visualized by enhanced chemiluminescence (ECL, GE Healthcare, UK or Pierce Biotechnology, UK) and exposure to light-sensitive film (Hyperfilm ECL, GE Healthcare, UK) or Biospectrum AC Imaging System (UVP, UK).

Light and Confocal Microscopy

To determine the intracellular trafficking of anti-CD20 mAb and FcγRIIb, CLL cells were incubated with appropriate Alexa 488-labeled mAb for various times as described in the figure legends and then harvested, washed and fixed with 2% paraformaldehyde. For detection of FcγRIIb and LAMP-1, respectively, cells were then permeabilized with 0.3% saponin and incubated with Alexa-647-labeled AT10 F(ab')$_2$ (labeling performed with Alexa Fluor-647 labeling kit (Invitrogen) as per the manufacturer's protocol), and/or biotin conjugated anti-human CD107a (LAMP-1) (eBioscience, UK). Cells were then washed, streptavidin-Alexa Fluor-547 (Invitrogen) added, followed by further washing. Cells were then transferred onto slides and images captured using LAS-AF v2 software on a TCS-SP5 laser scanning confocal microscope (Leica Microsystems, UK) (10× eye piece, 100× objective lens).

To determine cell proximity at different cell dilutions, cells were seeded at 1-20×10$^5$/ml, stimulated with various mAb for 2 and/or 6 h and then their relative proximity assessed by light microscopy. Cells were viewed with an Olympus CKX21 inverted microscope (Olympus, UK) using a 10× or 20×/0.25 PH lens. Images were acquired using a CCL2 digital cooled camera (Olympus) and were processed with Cell B (Olympus Soft imaging solutions) and Adobe Photoshop version CS2 software (Adobe, San Jose, Calif.).

Statistical Analysis

Statistical analysis was performed using GraphPadPrism (GraphPad Software, USA). Paired, non-parametric data was analyzed using the Wilcoxon's paired test whilst unpaired data was analyzed using the Mann-Whitney test.

Exemplary Compositions, Formulations and Modes of Administration

The invention provides methods of treatment, prophylaxis, and amelioration of one or more symptoms associated with a disease, disorder or infection by administering to a subject or patient an effective amount of a pharmaceutical composition of the invention.

In a specific embodiment, the subject or patient is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition of the invention, e.g., encapsulation in liposomes, microparticles, microcapsules, recombinant cells capable of expressing the antibody etc.

In some embodiments, the compositions of the invention are formulated in liposomes for targeted delivery of the antibodies of the invention. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al, 1985, Proc. Natl. Acad. Sci. USA, 82: 3688; Hwang et al, 1980 Proc. Natl. Acad. Sci. USA, 77: 4030-4; U.S. Pat. Nos. 4,485,045 and 4,544,545; all of which are incorporated herein by reference in their entirety.

Methods of administering the compositions of the invention include, but are not limited to, parenteral administration (e.g., introdermal, intramuscular, introperitoneal, intravenous and subcutaneous), epidural, and mucosal (e.g., intranasal and oral routes). In a specific embodiment, the compositions of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc). and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight independently for each antibody in the combination. Preferably, the dosage of each antibody administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kh, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg to 02.5 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of each of the antibodies of the compositions of the invention administered to a patient are 0.01 mg to 1000 mg/day.

The compositions of the inventions comprise a prophylactically or therapeutically effective amount of an agent and antibody as disclosed herein and a pharmaceutically acceptable carrier.

In a specific embodiment, the term "pharmaceutically acceptable" means approved by a regulatory agency or listed in the US Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed a s liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

In various embodiments, an antibody and an agent can be administered simultaneously or less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 100 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of disease, the route of administration, as well as age, body weight, response, and the past medical history of the patient. Suitable regimens can be selected by one skilled in the art by considering such factors and by following, for example, dosages reported in the literature and recommended in the Physician's Desk Reference ($56^{th}$ ed., 2002).

Summary

Recently, we found that type I mAb like rituximab modulate from the surface of human CD20 Tg mouse B cells (in vitro and in vivo) and from certain primary tumor cells derived from patients with NHL, thereby limiting their capacity to recruit effectors and deplete target cells (28). We have considered a possible mechanism to explain the limitation of the therapeutic activity of rituximab and other type I CD20 mAb and importantly, provide an opportunity for the blocking or avoidance of this process and thereby developing more potent reagents. The present work provides a molecular rationale for CD20 modulation induced by rituximab and ofatumumab. FcγRIIb expression should provide an important prognostic marker for response to type I anti-CD20 mAb. When primary CLL/SLL cells were cultured with type I anti-CD20 mAb, significant but heterogeneous modulation of CD20 was observed, and this heterogeneity could not be linked to known prognostic factors in CLL. Analysis of other B-NHL subtypes showed that MCL displayed similar heterogeneous modulation to CLL, but that FL and notably DLBCL showed significantly less modulation. Based on these results we now report a close correlation between the level of FcγRIIb expression in these malignancies and the extent to which they modulate in a 6 hour culture. Furthermore, we suggest that this modulation could explain some of the heterogeneity in response to rituximab seen in these diseases. Rituximab is of most proven benefit in DLBCL and FL, where it is established first-line therapy, in combination with chemotherapy. By contrast it has proven harder to demonstrate an improvement in OS in CLL with rituximab (39), and its benefits in MCL are even more modest (5). Thus as a general finding, B-cell malignancies that express FcγRIIb were more likely to modulate CD20 and tend to benefit less from rituximab treatment. However, even within DLBCL and FL, some cases do not respond to rituximab. As an example, transformed FL cases are generally poorly responsive to therapy, and express FcγRIIb (21), an observation consistent with our own findings that one of the high FcγRIIb-expressing samples (FIG. 2C) was identified as an FL and demonstrated correspondingly high rates of modulation. Although on a single case, we feel this could potentially provide an important means of resistance to rituximab.

CD20 modulation showed a strong correlation with FcγRIIb expression level regardless of B-NHL disease subtype. It was previously suggested that FcγRIIb could inhibit therapeutic mAb efficacy by competing with activatory Fc receptors on effector cells, thereby inhibiting cytotoxic signaling (40). Our in vitro investigations suggests that rituximab co-crosslinks CD20 and FcγRIIb predominantly on the same cell, resulting in activation of FcγRIIb, and the rapid paired internalization of both surface antigens together with bound mAb into lysosomes for degradation. The expression of FcγRIIb appears to result in decreased effector-cell recruitment through its ability to down-regulate the surface expression of the mAb on the target cell.

We also showed that co-incubation with a blocking anti-FcγRIIb mAb was able to prevent both FcγRIIb activation and rapid internalization of rituximab. Altogether, these data confirm the direct link between activation of FcγRIIb and rapid internalization of mAb from the cell surface.

The strong correlation between CD20 modulation induced by type I anti-CD20 mAb across different B-NHL subtypes and FcγRIIb expression, along with our transfection studies suggest that FcγRIIb is a key regulator of CD20 modulation.

Other groups have investigated the role of FcγRIIb in lymphoma. Camilleri-Broet et al (20) failed to show any significant relationship between response to R-CHOP and FcγRIIb expression in DLBCL, however only 18% (42/234 cases) were deemed FcγRIIb positive by immunohistochemistry in the earlier series (21). Given the relatively low frequency of positivity, it is probable that the number of positive cases might have been insufficient to detect a difference. Rather than over-expression, Weng and Levy (24) investigated whether two alleles of FcγRIIb (the 232I allele, which is more efficient at BCR-mediated calcium regulation than the 232T allele in autoimmune disease (22, 23)), were linked with rituximab efficacy but failed to demonstrate any correlation between this polymorphism and response to single-agent rituximab therapy in FL patients. The main concern, raised by the authors themselves, was that only 17 patients possessed the 232T allele, again limiting the statistical power of the study. Additionally, the polymorphisms studied reflected efficiency of BCR inhibition in autoimmune disease, and there are no published observations indicating that these polymorphisms are relevant in lymphoma or influence Fc binding of human IgG1. FcγRIIb expression, through its ability to regulate the rate of internalization will be an important prognostic indicator on the success of immunotherapy with type I mAb (including rituximab and ofatumumab). It may have a less pronounced effect upon type II mAb therapy.

Furthermore, in two different in vivo models we have demonstrated the ability of CD32 to limit mAb efficacy and the capacity of anti-CD32b mAb to overcome this limitation and augment rituximab therapy.

REFERENCES

1. Feugier, P., Van Hoof, A., Sebban, C., Solal-Celigny, P., Bouabdallah, R., Ferme, C., Christian, B., Lepage, E., Tilly, H., Morschhauser, F., et al. 2005. Long-term results of the R-CHOP study in the treatment of elderly patients with diffuse large B-cell lymphoma: a study by the Groupe d'Etude des Lymphomes de l'Adulte. *J Clin Oncol* 23:4117-4126.
2. Sehn, L. H., Donaldson, J., Chhanabhai, M., Fitzgerald, C., Gill, K., Klasa, R., MacPherson, N., O'Reilly, S., Spinelli, J. J., Sutherland, J., et al. 2005. Introduction of combined CHOP plus rituximab therapy dramatically improved outcome of diffuse large B-cell lymphoma in British Columbia. *J Clin Oncol* 23:5027-5033.
3. Marcus, R., Imrie, K., Belch, A., Cunningham, D., Flores, E., Catalano, J., Solal-Celigny, P., Offner, F., Walewski, J., Raposo, J., et al. 2005. CVP chemotherapy plus rituximab compared with CVP as first-line treatment for advanced follicular lymphoma. *Blood* 105:1417-1423.
4. Marcus, R., Imrie, K., Solal-Celigny, P., Catalano, J. V., Dmoszynska, A., Raposo, J. C., Offner, F. C., Gomez-Codina, J., Belch, A., Cunningham, D., et al. 2008. Phase III study of R-CVP compared with cyclophosphamide, vincristine, and prednisone alone in patients with previously untreated advanced follicular lymphoma. *J Clin Oncol* 26:4579-4586.
5. Lenz, G., Dreyling, M., Hoster, E., Wormann, B., Duhrsen, U., Metzner, B., Eimermacher, H., Neubauer, A., Wandt, H., Steinhauer, H., et al. 2005. Immunochemotherapy with rituximab and cyclophosphamide, doxorubicin, vincristine, and prednisone significantly improves response and time to treatment failure, but not long-term outcome in patients with previously untreated mantle cell lymphoma: results of a prospective randomized trial of the German Low Grade Lymphoma Study Group (GLSG). *J Clin Oncol* 23:1984-1992.
6. Kharfan-Dabaja, M. A., Fahed, R., Hussein, M., and Santos, E. S. 2007. Evolving role of monoclonal antibodies in the treatment of chronic lymphocytic leukemia. *Expert Opin Investig Drugs* 16:1799-1815.
7. Stolz, C., and Schuler, M. 2009. Molecular mechanisms of resistance to Rituximab and pharmacologic strategies for its circumvention. *Leuk Lymphoma* 50:873-885.
8. Davis, T. A., Czerwinski, D. K., and Levy, R. 1999. Therapy of B-cell lymphoma with anti-CD20 antibodies can result in the loss of CD20 antigen expression. *Clin Cancer Res* 5:611-615.
9. Michel, R. B., and Mattes, M. J. 2002. Intracellular accumulation of the anti-CD20 antibody 1F5 in B-lymphoma cells. *Clin Cancer Res* 8:2701-2713.
10. Hiraga, J., Tomita, A., Sugimoto, T., Shimada, K., Ito, M., Nakamura, S., Kiyoi, H., Kinoshita, T., and Naoe, T. 2009. Down-regulation of CD20 expression in B-cell lymphoma cells after treatment with rituximab-containing combination chemotherapies: its prevalence and clinical significance. *Blood* 113:4885-4893.

11. Treon, S. P., Mitsiades, C., Mitsiades, N., Young, G., Doss, D., Schlossman, R., and Anderson, K. C. 2001. Tumor Cell Expression of CD59 Is Associated With Resistance to CD20 Serotherapy in Patients With B-Cell Malignancies. *J Immunother* (1991) 24:263-271.
12. Golay, J., Lazzari, M., Facchinetti, V., Bernasconi, S., Borleri, G., Barbui, T., Rambaldi, A., and Introna, M. 2001. CD20 levels determine the in vitro susceptibility to rituximab and complement of B-cell chronic lymphocytic leukemia: further regulation by CD55 and CD59. *Blood* 98:3383-3389.
13. Jazirehi, A. R., Vega, M. I., and Bonavida, B. 2007. Development of rituximab-resistant lymphoma clones with altered cell signaling and cross-resistance to chemotherapy. *Cancer Res* 67:1270-1281.
14. Weng, W. K., and Levy, R. 2003. Two immunoglobulin G fragment C receptor polymorphisms independently predict response to rituximab in patients with follicular lymphoma. *J Clin Oncol* 21:3940-3947.
15. Clynes, R. A., Towers, T. L., Presta, L. G., and Ravetch, J. V. 2000. Inhibitory Fc receptors modulate in vivo cytoxicity against tumor targets. *Nat Med* 6:443-446.
16. Uchida, J., Hamaguchi, Y., Oliver, J. A., Ravetch, J. V., Poe, J. C., Haas, K. M., and Tedder, T. F. 2004. The innate mononuclear phagocyte network depletes B lymphocytes through Fc receptor-dependent mechanisms during anti-CD20 antibody immunotherapy. *J Exp Med* 199:1659-1669.
17. Nimmerjahn, F., and Ravetch, J. V. 2007. Antibodies, Fc receptors and cancer. *Curr Opin Immunol* 19:239-245.
18. Beers, S. A., Chan, C. H., James, S., French, R. R., Attfield, K. E., Brennan, C. M., Ahuja, A., Shlomchik, M. J., Cragg, M. S., and Glennie, M. J. 2008. Type II (tositumomab) anti-CD20 monoclonal antibody out performs type I (rituximab-like) reagents in B-cell depletion regardless of complement activation. *Blood* 112:4170-4177.
19. Mossner, E., Brunker, P., Moser, S., Puntener, U., Schmidt, C., Herter, S., Grau, R., Gerdes, C., Nopora, A., van Puijenbroek, E., et al. Increasing the efficacy of CD20 antibody therapy through the engineering of a new type II anti-CD20 antibody with enhanced direct- and immune effector cell-mediated B-cell cytotoxicity. *Blood*.
20. Camilleri-Broet, S., Mounier, N., Delmer, A., Briere, J., Casasnovas, O., Cassard, L., Gaulard, P., Christian, B., Coiffier, B., and Sautes-Fridman, C. 2004. FcgammaRIIB expression in diffuse large B-cell lymphomas does not alter the response to CHOP+rituximab (R-CHOP). *Leukemia* 18:2038-2040.
21. Camilleri-Broet, S., Cassard, L., Broet, P., Delmer, A., Le Touneau, A., Diebold, J., Fridman, W. H., Molina, T. J., and Sautes-Fridman, C. 2004. FcgammaRIIB is differentially expressed during B cell maturation and in B-cell lymphomas. *Br J Haematol* 124:55-62.
22. Li, X., Wu, J., Carter, R. H., Edberg, J. C., Su, K., Cooper, G. S., and Kimberly, R. P. 2003. A novel polymorphism in the Fcgamma receptor IIB (CD32B) transmembrane region alters receptor signaling. *Arthritis Rheum* 48:3242-3252.
23. Kono, H., Kyogoku, C., Suzuki, T., Tsuchiya, N., Honda, H., Yamamoto, K., Tokunaga, K., and Honda, Z. 2005. FcgammaRIIB Ile232Thr transmembrane polymorphism associated with human systemic lupus erythematosus decreases affinity to lipid rafts and attenuates inhibitory effects on B cell receptor signaling. *Hum Mol Genet* 14:2881-2892.
24. Weng, W. K., and Levy, R. 2009. Genetic polymorphism of the inhibitory IgG Fc receptor FcgammaRIIb is not associated with clinical outcome in patients with follicular lymphoma treated with rituximab. *Leuk Lymphoma* 50:723-727.
25. Chan, H. T., Hughes, D., French, R. R., Tutt, A. L., Walshe, C. A., Teeling, J. L., Glennie, M. J., and Cragg, M. S. 2003. CD20-induced lymphoma cell death is independent of both caspases and its redistribution into triton X-100 insoluble membrane rafts. *Cancer Res* 63:5480-5489.
26. Cragg, M. S., and Glennie, M. J. 2004. Antibody specificity controls in vivo effector mechanisms of anti-CD20 reagents. *Blood* 103:2738-2743.
27. Ivanov, A., Beers, S. A., Walshe, C. A., Honeychurch, J., Alduaij, W., Cox, K. L., Potter, K. N., Murray, S., Chan, C. H., Klymenko, T., et al. 2009. Monoclonal antibodies directed to CD20 and HLA-DR can elicit homotypic adhesion followed by lysosome-mediated cell death in human lymphoma and leukemia cells. *J Clin Invest* 119:2143-2159.
28. Beers, S. A., French, R. R., Chan, H. T., Lim, S. H., Jarrett, J. C., Vidal, R. M., Wijayaweera, S. S., Dixon, S. V., Kim, H. J., Cox, K. L., et al. 2010. Antigenic modulation limits the efficacy of anti-CD20 antibodies. *Blood*: In press.
29. Wiestner, A., Rosenwald, A., Barry, T. S., Wright, G., Davis, R. E., Henrickson, S. E., Zhao, H., Ibbotson, R. E., Orchard, J. A., Davis, Z., et al. 2003. ZAP-70 expression identifies a chronic lymphocytic leukemia subtype with unmutated immunoglobulin genes, inferior clinical outcome, and distinct gene expression profile. *Blood* 101:4944-4951.
30. Crespo, M., Bosch, F., Villamor, N., Bellosillo, B., Colomer, D., Rozman, M., Marce, S., Lopez-Guillermo, A., Campo, E., and Montserrat, E. 2003. ZAP-70 expression as a surrogate for immunoglobulin-variable-region mutations in chronic lymphocytic leukemia. *N Engl J Med* 348:1764-1775.
31. Damle, R. N., Wasil, T., Fais, F., Ghiotto, F., Valetto, A., Allen, S. L., Buchbinder, A., Budman, D., Dittmar, K., Kolitz, J., et al. 1999. Ig V gene mutation status and CD38 expression as novel prognostic indicators in chronic lymphocytic leukemia. *Blood* 94:1840-1847.
32. Ibrahim, S., Keating, M., Do, K. A., O'Brien, S., Huh, Y. O., Jilani, I., Lerner, S., Kantarjian, H. M., and Albitar, M. 2001. CD38 expression as an important prognostic factor in B-cell chronic lymphocytic leukemia. *Blood* 98:181-186.
33. Hamblin, T. J., Davis, Z., Gardiner, A., Oscier, D. G., and Stevenson, F. K. 1999. Unmutated Ig V(H) genes are associated with a more aggressive form of chronic lymphocytic leukemia. *Blood* 94:1848-1854.
34. Krober, A., Seiler, T., Benner, A., Bullinger, L., Bruckle, E., Lichter, P., Dohner, H., and Stilgenbauer, S. 2002. V(H) mutation status, CD38 expression level, genomic aberrations, and survival in chronic lymphocytic leukemia. *Blood* 100:1410-1416.
35. Ravetch, J. V., and Bolland, S. 2001. IgG Fc receptors. *Annu Rev Immunol* 19:275-290.
36. Walshe, C. A., Beers, S. A., French, R. R., Chan, C. H., Johnson, P. W., Packham, G. K., Glennie, M. J., and Cragg, M. S. 2008. Induction of cytosolic calcium flux by CD20 is dependent upon B Cell antigen receptor signaling. *J Biol Chem* 283:16971-16984.
37. Polyak, M. J., Li, H., Shariat, N., and Deans, J. P. 2008. CD20 homo-oligomers physically associate with the B cell antigen receptor. Dissociation upon receptor engagement and recruitment of phosphoproteins and calmodulin-binding proteins. *J Biol Chem* 283:18545-18552.
38. Ternynck, T., Dighiero, G., Follezou, J., and Binet, J. L. 1974. Comparison of normal and CLL lymphocyte surface Ig determinants using peroxidase-labeled antibodies. I. Detection and quantitation of light chain determinants. *Blood* 43:789-795.
39. Robak, T., Dmoszynska, A., Solal-Celigny, P., Warzocha, K., Loscertales, J., Catalano, J., Afanasiev, B. V., Larratt, L., Geisler, C. H., Montillo, M., et al. Rituximab Plus Fludarabine and Cyclophosphamide Prolongs Progression-Free Survival Compared With Fludarabine and Cyclophosphamide Alone in Previously Treated Chronic Lymphocytic Leukemia. *J Clin Oncol.*
40. Fridman, W. H., Teillaud, J. L., Bouchard, C., Teillaud, C., Astier, A., Tartour, E., Galon, J., Mathiot, C., and Sautes, C. 1993. Soluble Fc gamma receptors. *J Leukoc Biol* 54:504-512.
41. Nimmerjahn, F., and Ravetch, J. V. 2008. Fcgamma receptors as regulators of immune responses. *Nat Rev Immunol* 8:34-47.
42. Aman, M. J., Tosello-Trampont, A. C., and Ravichandran, K. 2001. Fc gamma RIIB1/SHIP-mediated inhibitory signaling in B cells involves lipid rafts. *J Biol Chem* 276:46371-46378.
43. Cragg, M. S., Morgan, S. M., Chan, H. T., Morgan, B. P., Filatov, A. V., Johnson, P. W., French, R. R., and Glennie, M. J. 2003. Complement-mediated lysis by anti-CD20 mAb correlates with segregation into lipid rafts. *Blood* 101:1045-1052.
44. Hamblin, T. J., Orchard, J. A., Ibbotson, R. E., Davis, Z., Thomas, P. W., Stevenson, F. K., and Oscier, D. G. 2002. CD38 expression and immunoglobulin variable region mutations are independent prognostic variables in chronic lymphocytic leukemia, but CD38 expression may vary during the course of the disease. *Blood* 99:1023-1029.
45. Mockridge, C. I., Potter, K. N., Wheatley, I., Neville, L. A., Packham, G., and Stevenson, F. K. 2007. Reversible anergy of sIgM-mediated signaling in the two subsets of CLL defined by VH-gene mutational status. *Blood* 109:4424-4431.
46. Potter, K. N., Mockridge, C. I., Neville, L., Wheatley, I., Schenk, M., Orchard, J., Duncombe, A. S., Packham, G., and Stevenson, F. K. 2006. Structural and functional features of the B-cell receptor in IgG-positive chronic lymphocytic leukemia. *Clin Cancer Res* 12:1672-1679.
47. Greenman, J., Tutt, A. L., George, A. J., Pulford, K. A., Stevenson, G. T., and Glennie, M. J. 1991. Characterization of a new monoclonal anti-Fc gamma RII antibody, AT10, and its incorporation into a bispecific F(ab')2 derivative for recruitment of cytotoxic effectors. *Mol Immunol* 28:1243-1254.
48. Glennie, M. J., McBride, H. M., Worth, A. T., and Stevenson, G. T. 1987. Preparation and performance of bispecific F(ab' gamma)2 antibody containing thioether-linked Fab' gamma fragments. *J Immunol* 139:2367-2375.
49. Tutt, A. L., French, R. R., Illidge, T. M., Honeychurch, J., McBride, H. M., Penfold, C. A., Fearon, D. T., Parkhouse, R. M., Klaus, G. G., and Glennie, M. J. 1998. Monoclonal antibody therapy of B cell lymphoma: signaling activity on tumor cells appears more important than recruitment of effectors. *J Immunol* 161:3176-3185.
50. Beer, S. A. et al. 2010. Seminars in Haematology 47(2): pp 107-114
51. Niederfellner, G et al. 2011. Blood 118, 358-367.
52. Teeling, J. L. 2004. Blood 104, 1793-1800.

What is claimed is:

1. An antibody molecule that binds to human FcγRIIb, wherein the antibody molecule comprises:
   a heavy chain variable region (VH) comprising:
      a VH CDR1 consisting of the amino acid sequence of SEQ ID NO: 83;
      a VH CDR2 consisting of the amino acid sequence of SEQ ID NO: 84; and
      a VH CDR3 consisting of the amino acid sequence of SEQ ID NO: 85; and
   a light chain variable region (VL) comprising:
      a VL CDR1 consisting of the amino acid sequence of SEQ ID NO: 86;
      a VL CDR2 consisting of the amino acid sequence of SEQ ID NO: 87; and
      a VL CDR3 consisting of the amino acid sequence of SEQ ID NO: 88.

2. The antibody molecule of claim 1, wherein the VH consists of the amino acid sequence of SEQ ID NO: 12; and the VL consists of the amino acid sequence of SEQ ID NO: 25.

3. The antibody molecule of claim 1, wherein the antibody molecule further comprises a heavy chain constant region (CH) consisting of the amino acid sequence of SEQ ID NO: 1; and a light chain constant region (CL) consisting of the amino acid sequence of SEQ ID NO:2.

4. The antibody molecule of claim 1, wherein the antibody molecule is any of an antibody; a chimeric antibody; a single chain antibody; or a Fab, F(ab')$_2$, Fv, or ScFv antibody fragment.

5. The antibody molecule of claim 4, wherein the antibody molecule is a monoclonal antibody.

* * * * *